(12) United States Patent
Lanza et al.

(10) Patent No.: US 8,796,021 B2
(45) Date of Patent: Aug. 5, 2014

(54) BLASTOMERE CULTURE TO PRODUCE MAMMALIAN EMBRYONIC STEM CELLS

(75) Inventors: Robert Lanza, Clinton, MA (US); Young Chung, Shrewsbury, MA (US)

(73) Assignee: Advanced Cell Technology, Inc., Marlborough, MA (US)

( * ) Notice: Subject to any disclaimer, the term of this patent is extended or adjusted under 35 U.S.C. 154(b) by 833 days.

(21) Appl. No.: 12/528,212

(22) PCT Filed: Feb. 22, 2008

(86) PCT No.: PCT/US2008/002380
§ 371 (c)(1),
(2), (4) Date: Apr. 29, 2010

(87) PCT Pub. No.: WO2008/103462
PCT Pub. Date: Aug. 28, 2008

(65) Prior Publication Data
US 2010/0240132 A1  Sep. 23, 2010

Related U.S. Application Data

(60) Provisional application No. 60/918,543, filed on Mar. 16, 2007, provisional application No. 60/993,772, filed on Sep. 14, 2007, provisional application No. 61/009,432, filed on Dec. 28, 2007, provisional application No. 60/902,970, filed on Feb. 23, 2007.

(51) Int. Cl.
*C12N 15/00* (2006.01)
*C12N 5/0735* (2010.01)
*C12N 5/073* (2010.01)

(52) U.S. Cl.
CPC ............ *C12N 5/0606* (2013.01); *C12N 5/0603* (2013.01); *C12N 2533/52* (2013.01)
USPC .......................................... 435/377; 435/366

(58) Field of Classification Search
CPC ............... C12N 5/0606; C12N 5/0603; C12N 2533/52; C12N 2502/02; C12N 2517/04; C12N 2533/90; C12N 5/069
See application file for complete search history.

(56) References Cited

U.S. PATENT DOCUMENTS

| | | | |
|---|---|---|---|
| 5,945,577 | A | 8/1999 | Stice |
| 7,838,727 | B2 | 11/2010 | Lanza |
| 7,893,315 | B2 | 2/2011 | Chung |
| 8,642,328 | B2 | 2/2014 | Lanza et al. |
| 2002/0001842 | A1 | 1/2002 | Chapman |
| 2002/0022268 | A1 | 2/2002 | Xu et al. |
| 2002/0035735 | A1 | 3/2002 | Schatten et al. |
| 2003/0044976 | A1 | 3/2003 | Dominko et al. |
| 2003/0059939 | A1 | 3/2003 | Page et al. |
| 2003/0070186 | A1 | 4/2003 | Strelchenko et al. |
| 2003/0087859 | A1 | 5/2003 | Kochanek et al. |
| 2003/0106082 | A1 | 6/2003 | Schatten et al. |
| 2003/0213008 | A1 | 11/2003 | Perry et al. |
| 2003/0229908 | A1 | 12/2003 | Cibelli et al. |
| 2003/0232430 | A1 | 12/2003 | Cibelli et al. |
| 2004/0199935 | A1 | 10/2004 | Chapman |
| 2004/0229350 | A1 | 11/2004 | Strelchenko et al. |
| 2005/0118713 | A1 | 6/2005 | Strelchenko et al. |
| 2005/0138680 | A1 | 6/2005 | Lee et al. |
| 2005/0265976 | A1 | 12/2005 | Cibelli et al. |
| 2005/0273870 | A1 | 12/2005 | Robl et al. |
| 2006/0014278 | A1 | 1/2006 | Khillan |
| 2006/0051332 | A1 | 3/2006 | Lanza |
| 2006/0206953 | A1 | 9/2006 | Lanza et al. |
| 2007/0298496 | A1 | 12/2007 | Kuo et al. |
| 2008/0057041 | A1 | 3/2008 | Chung |
| 2009/0092588 | A1 | 4/2009 | Stice et al. |
| 2009/0271335 | A1 | 10/2009 | West et al. |
| 2011/0150842 | A1 | 6/2011 | Lanza et al. |
| 2011/0183415 | A1 | 7/2011 | Chung et al. |

FOREIGN PATENT DOCUMENTS

| | | |
|---|---|---|
| JP | 2010-518857 | 6/2010 |
| WO | 95/16770 | 6/1995 |
| WO | 95/17500 | 6/1995 |
| WO | WO 98/30683 | 7/1998 |
| WO | WO 98/39416 | 9/1998 |
| WO | WO 01/00650 | 1/2001 |
| WO | WO 01/26454 | 4/2001 |
| WO | WO 01/45500 | 6/2001 |
| WO | 01/50848 | 7/2001 |
| WO | 03/018760 | 3/2003 |
| WO | WO 03/018767 | 3/2003 |
| WO | WO 03/018780 | 3/2003 |
| WO | WO 03/046141 | 6/2003 |

(Continued)

OTHER PUBLICATIONS

Wilton et al. Biopsy of Preimplantation Mouse Embryos: Development of Micromanipulated Embryos and Proliferation of Single Blastomeres in Vitro'Biol. Reproduction, 1989, vol. 40, pp. 145-152.*
Strelchenko et al. Embryonic Stem Cells from Morula. Methods in Enzymology, 2006, vol. 418, pp. 93-108.*
Stojkovic et al. Derivation, growth and applications of human embryonic stem cells. Reproduction, 2004, vol. 128, pp. 250-267.*
Klimanskaya et al., (2006), Nature, 444(7118):481-485.
Geber et al., (1995), Human Reprod., 10(6):1492-1496.
Li et al., (1992), Theriogenology, 37(1):246.
Roudebush et al., (1990), American Journal of Obstetrics & Gynecology, 162(4):1084-1090.
Kato et al., (1999), Biol. Reprod., 61(4):1110-1114.
Finkel (Jun. 19, 2007), "Spare the embryo, Save the Stem Cell" (Online), retrieved from http://news.sciencemag.org/sciencenow/2007/06/19-03.html on Oct. 12, 2010.

(Continued)

*Primary Examiner* — Deborah Crouch
(74) *Attorney, Agent, or Firm* — Wolf, Greenfield & Sacks, P.C.

(57) ABSTRACT

The present invention relates generally to the field of somatic cell nuclear transfer (SCNT) and to the creation of cloned animals and cells. The disclosure relates to a method of cloning a mammal, obtaining pluripotent cells such as embryonic stem cells, or for reprogramming a mammalian cell using an oocyte and a fertilized embryo.

7 Claims, 15 Drawing Sheets

(56) References Cited

FOREIGN PATENT DOCUMENTS

| WO | WO 03/057836 | 7/2003 |
|---|---|---|
| WO | 03/087296 | 10/2003 |
| WO | WO 03/100011 | 12/2003 |
| WO | 2005/070011 | 8/2005 |
| WO | 2005/080551 | 9/2005 |
| WO | 2006/013519 | 2/2006 |
| WO | 2006/013573 | 2/2006 |
| WO | WO 2006/052646 | 5/2006 |
| WO | 2006/080952 | 8/2006 |
| WO | WO 2007/019398 | 2/2007 |
| WO | WO 2007/047894 | 4/2007 |
| WO | WO 2007/130664 | 11/2007 |
| WO | WO 2008/103462 | 8/2008 |

OTHER PUBLICATIONS

Klimanskaya et al., (2007), Nature Protocols, 2(8):1963-1972.

Chung et al., (2008), Cell Stem Cell, 2(2):113-117.

Chung, et al., (2008), "Supplemental Data: Human Embryonic Stem Cell Lines Generated Without Embryo Destruction," Cell Stem Cell (On-line), retrieved from http://www.sciencedirect.com/science/MiamiMultiMediaURL/B8G3V-4RJK0CG-1/B8G3V-4RJK0CG-1-5/41804/html/S193459090700330X/33dae331c629755a9ae4032774548t4/mmc1.pdf on Oct. 13 2020, and retrieved from http://download.cell.com/cell-stem-cell/mmcs/journals/1934-5909/PIIS193459090700330X.mmc1.pdf on Mar. 21, 2011.

Strelchenko, N. et at. Morula-Dervived Human Embryonic Stem Cells. RMB Online. Oct. 27, 2004, vol. 9, No. 6, pp. 623-629.

Kwon, O. et al., Production of Live Young by Serial Nuclear Transfer with Mitotic Stages of Donor Nuclei in Mice. Journal of Reproduction and Development. 1997, vol. 43, No. 1, pp. 25-31.

Lanza et al. Extension of Cell Life-Span and Telomere Length in Animals Cloned from Senescent Somatic Cells. Science. Apr. 28, 2000, vol. 288, pp. 665-669.

Strojkovic, M. et al. Derivation of a Human Blastocyst After Heterologous Nuclear Transfer to Donated Oocytes. RMB Online. Jun. 15, 2005, vol. 11, No. 2, pp. 226-231.

Polejaev A, IA. et al. Cloned Pigs Produced by Nuclear Transfer from Adult Somatic Cells. Nature. Sep. 7, 2000, vol. 407, pp. 86-90.

Chung, Y. et al. Embryonic and Extraembryonic Stem Cell Lines Derived from Single Mouse Blastomeres. Nature. Jan. 2006, vol. 439, pp. 216-219.

Tsiunoda, Y. et al. Full-Term Development After Transfer of Nuclei From 4-Cell and Compacted Morula Stage Embryos to Enucleated Oocytes in the Mouse. The Journal of Experimental Zoology. 1997, vol. 278, pp. 250-254.

Wakayama, T., et al. Full-Term Development of Mice from Enucleated Oocytes Injected with Cumulus Cell Nuclei. Nature. Jul. 23, 1998, vol. 394, pp. 369-373.

Pera, M. F. et al. Human Embryonic Stem Cells. Journal of Cell Science. 2000, vol. 113, pp. 5-10.

Gordon, J. W. et al. Use of Zona Drilling for Safe and Effective Biopsy of Murine Oocytes and Embryos. Biology of Reproduction. 1990, vol. 42, pp. 869-876.

Taranger, C. K. et al. Induction of Dedifferentiation, Genomewide Transcriptional Programming by Extracts of Carcinoma and Embryonic Stem Cells. Molecular Biology of the Cell. Dec. 2005, vol. 16, pp. 5719-5735.

Amit et al., Feeder layer- and serum-free culture of human embryonic stem cells. Biol Reprod. Mar. 2004;70(3):837-45. Epub Nov. 19, 2003.

Andrews, From teratocarcinomas to embryonic stem cells. Philos Trans R Soc Lond B Biol Sci. Apr. 29, 2002;357(1420):405-17.

Becker et al., Embryonic stem cells from single blastomeres. Methods Enzymol. 2006;418:108-16.

Bradley, Production and analysis of chimaeric mice, in Teratocarcinomas and Embryonic Stem Cells (1987), IRL Oxford Press, 113-51.

Chan et al, Clonal propagation of primate offspring by embryo splitting. Science. Jan. 14, 2000;287(5451):317-9.

Chesne et al., Nuclear transfer in cattle: birth of cloned calves and estimation of blastomere totipotency in morulae used as a source of nuclei. C R Acad Sci III. 1993;316(5):487-91.

Cowan et al., Derivation of embryonic stem-cell lines from human blastocysts. N Engl J Med. Mar. 25, 2004;350(13):1353-6. Epub Mar. 3, 2004.

De Vos et al., Impact of cleavage-stage embryo biopsy in view of PGD on human blastocyst implantation: a prospective cohort of single embryo transfers. Hum Reprod. Dec. 2009;24(12):2988-96. doi: 10.1093/humrep/dep251. Epub Sep. 21, 2009.

Delhaise et al., Establishment of an embryonic stem cell line from 8-cell stage mouse embryos. Eur J Morphol. Nov. 1996;34(4):237-43.

Department of Health and Human Services, Stem Cell: Scientific Progress and Future Research Direction, (2001), Chapter 1: The Stem Cell, pp. 1-4; available from http://stemcells.nih.gov/info/2001report.htm.

Eistetter, (1989), Dev. Growth & Differ., 31(3):275-82.

Evans et al, Establishment in culture of pluripotential cells from mouse embryos. Nature. Jul. 9, 1981;292(5819):154-6.

Fong et al., Unsuccessful derivation of human embryonic stem cell lines from pairs of human blastomeres. Reprod Biomed Online. Aug. 2006;13(2):295-300.

Fu et al., Autologous feeder cells from embryoid body outgrowth support the long-term growth of human embryonic stem cells more effectively than those from direct differentiation. Tissue Eng Part C Methods. Aug. 2010;16(4):719-33. doi: 10.1089/ten.tec.2009.0360.

Geber et al., Blastomere development after embryo biopsy: a new model to predict embryo development and to select for transfer. Hum Reprod. Mar. 1999;14(3):782-6.

Guzman-Ayala et al., Nodal protein processing and fibroblast growth factor 4 synergize to maintain a trophoblast stem cell microenvironment. Proc Natl Acad Sci U S A. Nov. 2, 2004;101(44):15656-60. Epub Oct. 25, 2004.

Harton et al., Preimplantation genetic testing for Marfan syndrome. Mol Hum Reprod. Sep. 1996;2(9):713-5.

Harvey et al., Inducible control of gene expression: prospects for gene therapy. Curr Opin Chem Biol. Aug. 1998;2(4):512-8.

Hodgson et al., Stable benefit of embryonic stem cell therapy in myocardial infarction. Am J Physiol Heart Circ Physiol. Aug. 2004;287(2):H471-9.

Jaenisch et al., Stem cells, the molecular circuitry of pluripotency and nuclear reprogramming. Cell. Feb. 22, 2008;132(4):567-82. doi:10.1016/j.cell.2008.01.015.

Kubo, (2001), Acta Obstetrica et Gynaecologica Japonica, 53(9):152-9, 315.

Mansour et al., Transfer of zona-free embryos improves outcome in poor prognosis patients: a prospective randomized controlled study. Hum Reprod. May 2000;15(5):1061-4.

Matsuda et al., Production of transgenic chimera rabbit fetuses using somatic cell nuclear transfer. Cloning Stem Cells. 2002;4(1):9-19.

Mitalipov et al., Development of shesus monkey demi-embryos created by blastomere separation at the 2-cell stage, (2000), Theriogenology, 53:397.

Mitalipova, (2001), Cloning 3(2):59-67.

Nichols, Introducing embryonic stem cells. Curr Biol. Jul. 10, 2001;11(13):R503-5.

Ogawa et al., A novel mechanism for regulating clonal propagation of mouse ES cells. Genes Cells. May 2004;9(5):471-7.

Ouhibi et al., Initial culture behaviour of rat blastocysts on selected feeder cell lines. Mol Reprod Dev. Mar. 1995;40(3):311-24.

Papioannou, (2000), Ch. 4: Production of Chimeras and genetically defined offspring from targeted ES cells, In Joyner, A L 2nd ed. Gene Targeting: A Practical Approach, Oxford University Press, pp. 107-46.

Rani et al., A simple and convenient method for preparing chimeric animals from embryonic stem (ES) cells. Transgenic Res. Dec. 2003;12(6):739-41.

(56) References Cited

OTHER PUBLICATIONS

Reubinoff et al., "Embryonic Stem Cell Lines From Human Blastocysts: Somatic Differentiation in Vitro," Nature Biotechnology, Nature Publishing Group, New York, NY, vol. 18, No. 4, Apr. 2000, pp. 399-404.
Rexroad et al., Culture of blastomeres from in vitro-matured, fertilized, and cultured bovine embryos. Mol Reprod Dev. Oct. 1997;48(2):238-45.
Robertson, Embryo-derived stem cells, in Teratocarcinomas and Embryonic Stem Cells, (1987), IRL Oxford Press, pp. 71-112.
Rosler et al., Long-term culture of human embryonic stem cells in feeder-free conditions. Dev Dyn. Feb. 2004;229(2):259-74.
Saito et al., Effects of extracellular matrices and growth factors on the development of isolated porcine blastomeres. Biol Reprod. May 1991;44(5):927-36.
Schraermeyer et al., 2001, "Subretinally Transplanted Embryonic Stem Cell Rescue Photoreceptor Cells From Degeneration in the RCS Rats," Cell Transplantation, 10:673-680.
Schuldiner et al., Selective ablation of human embryonic stem cells expressing a "suicide" gene. Stem Cells. 2003;21(3):257-65.
Senger et al., (1997), Pathways to Pregnancy and Partition, Current Concepts, Inc. Pullman, Chapter 13, pp. 221.
Sills, Identification and isolation of embryonic stem cells in reproductive endocrinology: theoretical protocols for conservation of human embryos derived from in vitro fertilization, (2005), Theoretical Biol. And Medical Modeling, 2:25, 1-8. doi:10.1186/1742-4682-2-25.
Solter et al, Immunosurgery of mouse blastocyst. Proc Natl Acad Sci U S A. Dec. 1975;72(12):5099-102.
Springer et al., Prodrug-activating systems in suicide gene therapy. J Clin Invest. May 2000;105(9):1161-7.
Tanaka et al., Promotion of trophoblast stem cell proliferation by FGF4. Science. Dec. 11, 1998;282(5396):2072-5.
Tao et al., Cellular characterization of blastocysts derived from rabbit 4-, 8- and 16-cell embryos and isolated blastomeres cultured in vitro. Hum Reprod. Apr. 2000;15(4):881-9.
Tarkowski et al., How many blastomeres of the 4-cell embryo contribute cells to the mouse body? Int J Dev Biol. Oct. 2001;45(7):811-6.
Tarkowski et al., Identical triplets and twins developed from isolated blastomeres of 8- and 16-cell mouse embryos supported with tetraploid blastomeres. Int J Dev Biol. 2005;49(7):825-32.
Tesar, Derivation of germ-line-competent embryonic stem cell lines from preblastocyst mouse embryos. Proc Natl Acad Sci U S A. Jun. 7, 2005;102(23):8239-44. Epub May 25, 2005.
Thomson et al. "Embryonic Stem Cell Lines Derived from Human Blastocysts," Science, American Association for the Advancement of Science, Washington DC, vol. 282, Nov. 1998, pp. 1145-1147.
Thomson et al., Isolation of a primate embryonic stem cell line. Proc Natl Acad Sci U S A. Aug. 15, 1995;92(17):7844-8.
Van De Velde et al., Embryo implantation after biopsy of one or two cells from cleavage-stage embryos with a view to preimplantation genetic diagnosis. Prenat Diagn. Dec. 2000;20(13):1030-7.
Van De Velde et al., The four blastomeres of a 4-cell stage human embryo are able to develop individually into blastocysts with inner cell mass and trophectoderm. Hum Reprod. Aug. 2008;23(8):1742-7. doi: 10.1093/hurnrep/den190. Epub May 24, 2008.
Wade, (Oct. 17, 2005), New York Times, Stem Cell Trest Tried on Mice Saves Embryo, http://www.nytimes.com/2005/10/17/health/17stem.html?pagewanted=all&¯r=0.
Wakayama et al., Efficient establishment of mouse embryonic stem cell lines from single blastomeres and polar bodies. Stem Cells. Apr. 2007;25(4):986-93. Epub Dec. 21, 2006.
Wang et al., Increases in phosphorylation of SAPK/JNK and p38MAPK correlate negatively with mouse embryo development after culture in different media. Fertil Steril. Apr. 2005;83 Suppl 1:1144-54.

* cited by examiner

A

B

A

B

C

BDF: B6D2F1 *in vivo* fertilized embryos.
Single: F2GFP cumulus cell cloned embryos.
Serial: F2GFP cumulus cell serial cloned embryos.
There were 2-3 replicates in each developmental stage.

BDF: B6D2F1 *in vivo* fertilized embryos.
Single: F2GFP cumulus cell cloned embryos.
Serial: F2GFP cumulus cell serial cloned embryos.
There were 2-3 replicates in each developmental stage.

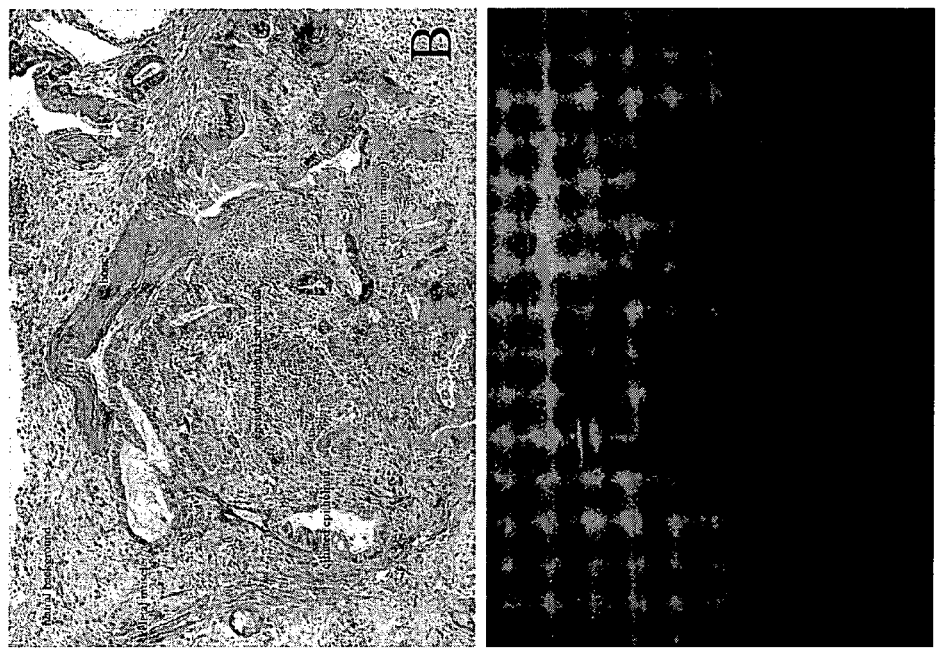
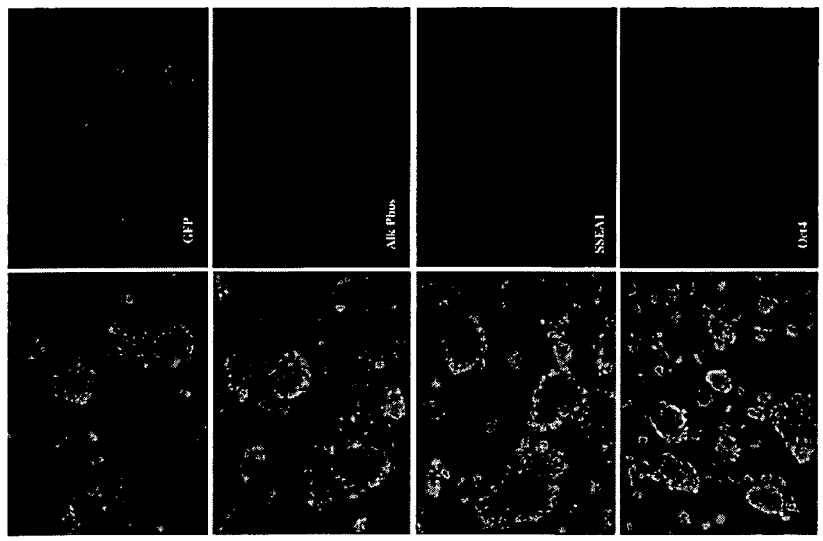
Figure 9A-9C

Figure 14

NED 1   NED 2   NED 3   NED 4   NED 5

BLASTOMERE CULTURE TO PRODUCE MAMMALIAN EMBRYONIC STEM CELLS

RELATED APPLICATIONS

This application is a U.S. National Phase Application of PCT Application PCT/US2008/002380 filed 22 Feb. 2008 and published as WO 2008/103462on 28 Aug. 2008, the contents of which is incorporated by reference in its entirety, and claims the benefit of U.S. Provisional Application Nos. 60/902,970 filed 23 Feb. 2007, 60/918,543 filed 16 Mar. 2007, 60/993,772 filed 14 Sep. 2007 and 61/009,432 filed 28 Dec. 2007, the contents of which are also incorporated by reference in their entirety.

FIELD OF THE INVENTION

The present invention relates generally to the field of somatic cell nuclear transfer (SCNT) and to the generation of animals and cells.

BACKGROUND OF THE INVENTION

Advances in stem cell technology, such as the isolation and propagation in vitro of human embryonic stem cells ("hES" cells), constitute an important new area of medical research. hES cells have a demonstrated potential to be propagated in the undifferentiated state and then to be induced subsequently to differentiate into any and all of the cell types in the human body, including complex tissues. This has led to the suggestion that many diseases resulting from the dysfunction of cells may be amenable to treatment by the administration of hES-derived cells of various differentiated types (Thomson et al., *Science* 282:1145-1147 (1998)). Nuclear transfer studies have demonstrated that it is possible to transform a somatic differentiated cell back to a totipotent state, such as that of embryonic stem cells ("ES") (Cibelli et al., *Nature Biotech* 16:642-646 (1998)) or embryo-derived ("ED") cells. The development of technologies to reprogram somatic cells back to a totipotent ES cell state, such as by the transfer of the genome of the somatic cell to an enucleated oocyte and the subsequent culture of the reconstructed embryo to yield ES cells, often referred to as somatic cell nuclear transfer ("SCNT"), offers a method to transplant ES-derived somatic cells with a nuclear genotype of the patient (Lanza et al., *Nature Medicine* 5:975-977 (1999)). It is expected that such cells and tissues would not be rejected, despite the presence of allogeneic mitochondria (Lanza et al, Nature Biotech 20:689-696, (2002)). Nuclear transfer also allows the rebuilding of telomere repeat length in cells through the reactivation of the telomerase catalytic component in the early embryo (Lanza et al, Science 288:665-669, (2000)). Nevertheless, there remains a need for improvements in methods to reprogram animal cells that increase the frequency of successful and complete reprogramming. There is also a need for reducing the dependence on the availability of human oocytes.

Animals having certain desired traits or characteristics, such as increased weight, milk content, milk production volume, length of lactation interval and disease resistance have long been desired. Traditional breeding processes are capable of producing animals with some specifically desired traits, but these traits are often accompanied by a number of undesired characteristics, and are often too time-consuming, costly and unreliable to develop. Moreover, these processes are completely incapable of allowing a specific animal line from producing gene products, such as desirable protein therapeutics that are otherwise entirely absent from the genetic complement of the species in question (i.e., human or humanized plasma protein or other molecules in bovine milk).

The development of technology capable of generating transgenic animals provides a means for exceptional precision in the production of animals that are engineered to carry specific traits or are designed to express certain proteins or other molecular compounds of therapeutic, scientific or commercial value. That is, transgenic animals are animals that carry the gene(s) of interest that has been deliberately introduced into existing somatic cells and/or germline cells at an early stage of development. As the animals develop and grow the protein product or specific developmental change engineered into the animal becomes apparent, and is present in their genetic complement and that of their offspring.

An additional problem associated with existing stem cell technologies are the ethical considerations of using advanced human embryos to obtain stem cells. Therefore it would be highly beneficial to have cloned embryos available at an early stage to limit ethical concerns.

In summary, this invention solves long outstanding problems with efficiency, ethical dilemmas, and the problem of how to clone embryos without oocytes.

SUMMARY OF THE INVENTION

This invention generally relates to methods of cloning somatic cells using a fertilized embryo as a recipient. In certain embodiments, an oocyte is the initial recipient and a fertilized embryo is a second recipient. In certain embodiments, the disclosure relates to a method for cloning a mammal, for obtaining pluripotent cells, or for reprogramming a mammalian cell.

In certain aspects, the disclosure provides a method for reprogramming a nucleus of a differentiated cell comprising the steps of providing a differentiated cell, an enucleated, MII-stage egg of an animal and an enucleated, 2-cell stage embryo of an animal, wherein said MII-stage egg and said embryo are synchronized; injecting the nucleus of said differentiated cell into said enucleated egg; activating said egg that comprises said nucleus; allowing said activated egg that comprises said nucleus to develop to the 2-cell stage; removing at least one nucleus and at least a portion of surrounding cytoplasm of said activated 2-cell stage egg from the previous step; fusing said at least one nucleus removed in the previous step into said enucleated, 2-cell stage embryo, preferably by positioning said nucleus between the 2 cells of the 2-cell stage embryo to generate a single cell containing a reprogrammed nucleus of the differentiated cell.

In certain aspects, the disclosure provides a method for producing an animal comprising providing a differentiated cell, an enucleated, MII-stage egg of an animal and an enucleated, 2-cell stage embryo of an animal, wherein said MII-stage egg and said embryo are synchronized; injecting the nucleus of said differentiated cell into said enucleated egg; activating said egg that comprises said nucleus; allowing said activated egg that comprises said nucleus to develop to the 2-cell stage; removing at least one nucleus and at least a portion of the surrounding cytoplasm of said 2-cell stage egg from the previous step; fusing said at least one nucleus removed in the previous step into said enucleated, 2-cell stage embryo to generate a single cell; and culturing said single cell from the previous step to allow development into an animal. In certain embodiments, culturing comprises implanting said cultured cells into a uterus of an animal. In certain embodiments, the implanted cells and the animal in which they are implanted are of the same species.

In certain aspects, the disclosure provides a method for producing embryonic stem cells, comprising the steps of providing a differentiated cell, an enucleated, MII-stage egg of an animal and an enucleated, 2-cell stage embryo of an animal, wherein said MII-stage egg and said embryo are synchronized; injecting the nucleus of said differentiated cell into said enucleated egg; activating said egg that comprises said nucleus; allowing said activated egg that comprises said nucleus to develop to the 2-cell stage; removing a nucleus and surrounding cytoplasm of said 2-cell stage egg from the previous step; fusing said nucleus removed in the previous step into said enucleated, 2-cell stage embryo, preferably by positioning said nucleus between the 2 cells of the 2-cell stage embryo to generate a single cell; and culturing said single cell from the previous step to a developmental stage where embryonic stem cells may be derived.

In certain embodiments, said embryonic stem cell is hemizygous or homozygous for an MHC allele, wherein either said differentiated cell is hemizygous or homozygous for an MHC allele or said embryonic stem cell is engineered to be hemizygous or homozygous for an MHC allele, by homologous recombination or by loss of heterozygocity, or both, and wherein said same species is human. In certain embodiments, said method is repeated many times to produce a bank of embryonic stem cells, each of which is hemizygous or homozygous for a different MHC allele than the other embryonic stem cells of the bank.

In certain aspects, the methods of the disclosure further comprise the steps of growing said resulting single cell from the previous methods to blastomere, morula or blastocyst stage. In certain aspects, the methods of the disclosure further comprise serial nuclear transfers into oocytes. In certain aspects, the methods of the disclosure further comprise serial nuclear transfers into embryos.

In certain embodiments, said egg is activated by cyclohexamide, $CsCl_2$, calcium ionopore, ionomycin, sperm factors, sperm portions or components, 6-DMAP, $SrCl_2$, cytochalasin B, or a combination thereof. In certain embodiments, said egg is activated by a combination of these agents. In a preferred embodiment, said egg is activated by a combination of ionomycin and 6-DMAP. In another preferred embodiment, said egg is activated by a combination of calcium ionopore and 6-DMAP. In another preferred embodiment, said egg is activated by a combination of $SrCl_2$ and cytochalasin B In certain embodiments, said fusion step is performed electrically. In certain embodiments, said electric fusion is performed in two steps: a first step in which said nucleus is lined up with the positive pole and electrically shocked and a second step in which the embryo and the nucleus are turned approximately 90 degrees and electrically shocked. In certain embodiment, the embryo and the nucleus are not turned before shocking. In certain embodiments, said fusion step is performed using a Sendai virus.

In certain embodiments, said MII-stage egg is a human egg. In certain embodiments, said enucleated, 2-cell stage embryo is a human embryo. In certain embodiments, said differentiated cell is a human cell. In certain embodiments, the cells of the disclosure may be from any mammal. In yet another embodiment, the mammal is selected from a mouse, rat, cat, dog, rabbit, goat, hamster, pig, sheep, non-human primate, or primate.

In certain embodiments, said MII-stage egg and said enucleated, 2-cell stage embryo are from any animal. In certain embodiments, said MII-stage egg and said enucleated, 2-cell stage embryo are from the same species. In certain embodiments, said differentiated cell and said MII-stage egg are from the same species. In certain embodiments, said differentiated cell and said enucleated, 2-cell stage embryo are from the same species. In certain embodiments, said differentiated cell, said MII-stage egg and said enucleated, 2-cell stage embryo are from the same species. In certain embodiments, said same species is human.

In certain aspects, the disclosure relates to a method for cloning a mammal, for obtaining pluripotent cells, or for reprogramming a mammalian cell. In certain embodiments, the method consists of the following steps: (a) obtaining a donor nucleus from a mammalian cell; (b) obtaining a fertilized embryo from a mammal; (c) transferring said donor nucleus into one cell of said fertilized embryo; (d) enucleating the original nucleus of said fertilized embryo, leaving the donor nucleus inside the fertilized embryo; and (e) culturing said fertilized embryo.

In certain embodiments, the enucleation step of the methods of the application is performed between 3 and 6 hours of the nuclear transfer step, between 4 and 6 hours of the nuclear transfer step, between 5 and 6 hours of the nuclear transfer step, between 3 and 4 hours of the nuclear transfer step, between 3 and 5 hours of the nuclear transfer step, or between 4 and 5 hours of the nuclear transfer step. In certain embodiments, the enucleation step is performed within 3 hours of the nuclear transfer step, within 2 hours of the nuclear transfer step, or within 1 hours of the nuclear transfer step. In certain embodiments, the enucleation step is performed between 1 and 2 hours of the nuclear transfer step, between 1 and 3 hours of the nuclear transfer step, between 1 and 4 hours of the nuclear transfer step, between 1 and 5 hours of the nuclear transfer step, between 1 and 6 hours of the nuclear transfer step, between 2 and 3 hours of the nuclear transfer step, between 2 and 4 hours of the nuclear transfer step, between 2 and 5 hours of the nuclear transfer step, or between 2 and 6 hours of the nuclear transfer step.

In certain embodiments of the disclosure, culturing the cloned embryo results in the development of a blastocyst or blastocyst-like collection of cells. In certain embodiments, embryonic stem cells can be derived from these blastocysts or blastocyst-like collection of cells. In certain other embodiments, culturing the cloned embryo results in the development of a 4-8 cell stage embryo or of a morula stage embryo. In certain embodiments, embryonic stem cells can be derived from all or a portion of such early cleavage stage or morula stage embryos. In certain other embodiments, culturing the cloned embryo results in the development of an embryo that continues to divide beyond the two-cell stage. In certain embodiments, an embryonic stem cell line is derived and established.

In certain aspects of the disclosure, the fertilized embryo is from a mammal of the same species as the mammalian donor cell. In certain embodiments of the disclosure, the fertilized embryo is from a mammal of a closely related species to the mammalian donor cell. In certain embodiments of the disclosure, the fertilized embryo is a pronuclear stage embryo. In certain embodiments, said fertilized embryo is a 2-cell stage embryo. In certain embodiments of the disclosure, the mammalian donor cell is an ES cell. In certain embodiments, said mammalian cell is a differentiated cell. In certain embodiments, said differentiated mammalian cell is a cumulus cell. In certain embodiments, said mammalian cell is a murine cell. In certain embodiments, said mammalian cell is a bovine cell. In certain embodiments, said mammalian cell is a human cell. In certain embodiments, cells may be from other mammalian species including, but not limited to, equine, canine, porcine, ovine sources; or rodent species such as rat may be used. In certain embodiments, the fertilized embryo underwent cryogenic preservation and was thawed prior to the nuclear transfer step.

In certain embodiments, the donor nucleus is labeled. In certain embodiments, said nucleus is labeled by expression of a fluorescent transgene.

In certain aspects, the disclosure relates to a method for cloning a mammalian cell comprising the steps of (a) obtaining a donor nucleus from a mammalian cell; (b) obtaining a first fertilized embryo from a mammal; (c) transferring said donor nucleus into said first fertilized embryo; (d) enucleating the original nucleus of said first fertilized embryo, leaving the donor nucleus inside the fertilized embryo; (e) culturing said fertilized embryo; (f) enucleating a second fertilized mammalian embryo; (g) dissociating the cells of the first fertilized embryo from step (e) and transplanting at least one cell into the enucleated second fertilized embryo; (h) fusing said transplanted cells to the cells of said enucleated second fertilized embryo to form a single-cell embryo; and (i) culturing said cloned single-cell embryo.

In certain embodiments, steps (f)-(i) are cycled through more than once with the fertilized embryo obtained in step (g) coming from the step (i) of the previous cycle. In certain embodiments, step (h) (fusing step) is accomplished by electrofusion. In certain embodiments, step (g) comprises transferring at least one nucleus of the fertilized embryo from step (e) into the enucleated second fertilized embryo.

In certain embodiments, the second fertilized embryo of the disclosure is at the same stage of development as the first fertilized embryo. In certain embodiments, the second fertilized embryo of the disclosure is at a similar stage of development as the first fertilized embryo. A similar stage may include embryos that are in the same general stage such as blastula stage or embryos of similar cell number stage developmental time. In certain embodiments, said second fertilized embryo and said first fertilized embryo are at the 2-cell stage and only one of the two cells is transplanted.

In certain aspects, the disclosure relates to a method for cloning a mammal, for obtaining pluripotent cells, or for reprogramming mammalian cells comprising the steps of: (a) obtaining desired donor nuclei from mammalian cells; (b) obtaining at least one fertilized embryo of at least the 2-cell stage from a mammal; (c) transferring donor nuclei into one or more but not all of the cells of the fertilized embryo, one donor nucleus into each cell; (d) enucleating the original nucleus of each of the cells of said embryo to which a donor nucleus was transferred, leaving the donor nucleus in said cell; and (e) culturing said fertilized embryo(es).

In certain embodiments, the fertilized embryo of the disclosure is a 2-cell stage embryo and a donor nucleus is transferred to only one of the two cells of said embryo. In various embodiments, the fertilized embryo of the disclosure may be an embryo of any stage. In certain embodiments, the activated oocyte of the disclosure is the recipient of nuclear transfer at the two cell stage. In certain embodiments, the oocyte is of any stage. In certain embodiments, the oocyte and the embryo are in synchrony.

In certain embodiments, the transferring of donor nuclei step is performed immediately before the enculeation step.

In certain aspects, the disclosure relates to a blastocyst derived from a fertilized embryo, wherein said fertilized embryo is produced by any of the methods of the disclosure. In certain embodiments, the disclosure relates to a blastula produced by any of the methods of the disclosure.

In certain embodiments of any of the foregoing, embryonic stem cells or embryonic stem cell lines can be produced using all or a portion of a cloned embryo. For example, embryonic stem cells or cell lines can be produced using all or a portion of a blastocyst stage cloned embryo or using all or a portion of an early cleavage stage or morula stage embryo.

In certain aspects, the disclosure relates to a method for producing embryonic stem cells, comprising the steps of: (a) providing a differentiated cell, an enucleated, MII-stage egg of an animal and providing an enucleated, 2-cell stage embryo of an animal, wherein said MII-stage egg and said embryo are synchronized; (b) injecting nucleus of said differentiated cell into said enucleated egg; (c) activating said egg that comprises said nucleus; (d) allowing said activated egg that comprises said nucleus to develop to the 2-cell stage; (e) removing a nucleus and surrounding cytoplasm of said 2-cell stage egg from step (d); (f) fusing said nucleus removed in step (e) into said enucleated, 2-cell stage embryo, preferably by positioning said nucleus between the 2 cells of the 2-cell stage embryo to generate a single cell; and (g) culturing said single cell from step (f) to a developmental stage where embryonic stem cells may be derived comprising: (i) culturing said single cells from (f) to the morula stage to generate a morula; (ii) isolating a blastomere from said morula; (iii) culturing said blastomere to generate a cluster of two or more blastomeres; (iv) directly or indirectly contacting the cultured cluster of two or more blastomeres with embryonic or fetal cells; and (v) culturing the cluster of two or more blastomeres of (iv) until ES cells are produced.

In certain aspects, the disclosure relates to a method of producing an embryonic stem (ES) cell, comprising: (a) culturing a blastomere removed or biopsied from a mammalian parental embryo and said mammalian parental embryo together for 12 to 18 hrs; (b) transferring the blastomere to blastocyst medium further comprising laminin and seeded with mouse embryonic fibroblasts (MEF) and (c) culturing the blastomere of (b) until ES cells are produced.

In certain aspects, the disclosure relates to a method of producing an embryonic stem (ES) cell, comprising: (a) culturing a blastomere removed or biopsied from a mammalian parental embryo and said mammalian parental embryo together; (b) transferring the blastomere to blastocyst medium further comprising laminin or fibronectin and (c) culturing the blastomere of (b) until ES cells are produced.

In certain aspects, the disclosure relates to a method for producing embryonic stem cells, comprising the steps of: (a) providing an enucleated, MII-stage egg of an animal, a differentiated cell and an enucleated, 2-cell stage embryo of an animal, wherein said MII-stage egg and said embryo are synchronized; (b) injecting nucleus of said differentiated cell into said enucleated egg; (c) activating said egg that comprises said nucleus; (d) allowing said activated egg that comprises said nucleus to develop to the 2-cell stage; (e) removing a nucleus and surrounding cytoplasm of said 2-cell stage egg from step (d); (f) fusing said nucleus removed in step (e) into said enucleated, 2-cell stage embryo, preferably by positioning said nucleus between the 2 cells of the 2-cell stage embryo to generate a single cell; (g) culturing said single cell from step (f) to generate a morula; (h) isolating a blastomere from said morula (e.g., which morula is a parental embryo); (i) culturing said blastomere and the parental embryo together for 12 to 18 hrs; (j) transferring the blastomere to blastocyst medium further comprising laminin or fibronectin and seeded with mouse embryonic fibroblasts (MEF) and (k) culturing the blastomere of (j) until ES cells are produced.

In certain embodiments, MEFs are mitotically inactivated. In certain embodiments, step (c) comprises culturing in conditions that reduce embryonic vesicle formation.

In certain embodiments, the blastocyst medium comprises 2.5 µg/ml of laminin. In certain embodiments, the blastocyst medium comprises 10 µl/ml of laminin. In certain embodiments, the blastocyst medium comprises about 2.5, 5, 7.5, 10, 15, or 20 µg/ml of laminin. In certain embodiments, the medium is supplemented with 1-5, 1-10, 5-10, 10-20 or 1-20 µg/ml of laminin. In certain embodiments, the medium is supplemented with at least 1, 2.5, 5, 7.5, 10, 15 or 20 µg/ml of laminin.

In certain embodiments, step (c) of the above methods comprises culturing in blastocyst medium seeded with MEF cells for 5 days. In certain embodiments, culturing in blastocyst medium seeded with MEF cells occurs for 1, 2, 3, 4, 5, 6, 7, 8, 9, or 10 days. In certain embodiments, step (c) of the above methods further comprises culturing until the blastomeres form cell clumps of about 20 cells and transferring the cell clumps to medium seeded with ES cells. In certain embodiments, cell clumps are about 5, 10, 15, 20, 30, 40, or 50 cells. In certain embodiments, the ES cells express a marker or are labeled. In certain embodiments, the ES cells express GFP. In certain embodiments, the parental embryos are transferred to blastocyst medium and allowed to develop into blastocysts. In certain embodiments, the blastomere is isolated from an embryo comprising: (a) immobilizing the embryo; and (b) tapping the immobilized embryo until a blastomere is isolated.

In certain embodiments, more than one blastomere is removed or biopsied from a parental embryo. For example, two blastomere may be biopsied from a parental embryo and used to derive ES cells.

In certain embodiments, embryonic stem cells are produced using methods that do not require and/or result in the destruction of an embryo. For example, when embryonic stem cells are produced from a single blastomere of a morula stage parental embryo, the remaining portion of the parental embryo can be subsequently frozen for long term or perpetual storage, or used to generate a pregnancy.

In certain embodiments, a blastomere removed or biopsied from a mammalian parental embryo and said mammalian parental embryo are cultured together for about 6 to 12, 6 to 18, 6 to 24, 12 to 18, 12 to 24, or 18 to 24 hrs.

The application contemplates using any of these aspects separately or combinations of any of the foregoing or following aspects and embodiments of the invention.

BRIEF DESCRIPTION OF THE DRAWINGS

FIG. 9A-9C show ES cell markers and teratoma formation of ES cells from serially cloned embryos. (A) ES cell markers. (B) Teratoma. (C) Chimeric pups.

FIG. 14 shows karyotypes of single blastomere-derived hES cell lines.

DETAILED DESCRIPTION OF THE INVENTION

Definitions

Figure 1A:
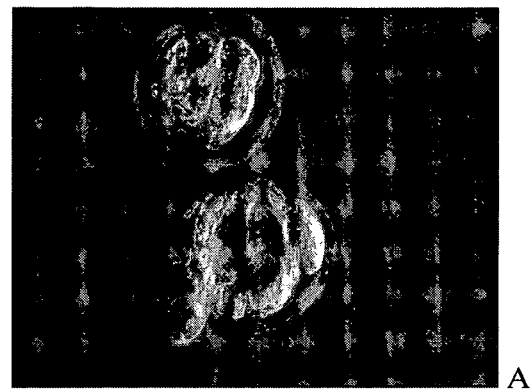
FIG. 1A-1B show mouse embryos cloned by serial cloning procedures. GFP positive ES cell nuclei were injected into recipient embryos. Embryos are shown under bright field (A) and fluorescent microscopy (B).

The term "embryonic stem cells" (ES cells) refers to cells derived from the inner cell mass of blastocysts or morulae that have been serially passaged as cell lines. The ES cells may be derived from fertilization of an egg cell with sperm or DNA, nuclear transfer, parthenogenesis, or by means to generate hES cells with homozygosity in the MHC region. The term "human embryonic stem cells" (hES cells) refers to human ES cells.

The term "pluripotent stem cells" refers to animal cells capable of differentiating into more than one differentiated cell type. Such cells include hES cells, human embryo-derived cells (hEDCs), and adult-derived cells including mesenchymal stem cells, neuronal stem cells, and bone marrow-derived stem cells. Pluripotent stem cells may be genetically modified or not genetically modified. Genetically modified cells may include markers such as fluorescent proteins to facilitate their identification within the egg.

The term "differentiated cell" as used herein refers to a any cell in the process of differentiating into a somatic cell lineage or having terminally differentiated. For example, embryonic cells can differentiate into an epithelial cell lining the intestine. Differentiated cells can be isolated from a fetus or a live born animal, for example.

The term "implanting" as used herein in reference to embryos refers to impregnating a female animal with an embryo described herein. This technique is well known to a person of ordinary skill in the art. See, e.g., Seidel and Elsden, 1997, Embryo Transfer in Dairy Cattle, W. D. Hoard & Sons, Co., Hoards Dairyman. The embryo may be allowed to develop in utero, or alternatively, the fetus may be removed from the uterine environment before parturition.

The term "synchronized" or "sychronous" as used herein in reference to estrus cycle, refers to assisted reproductive techniques well known to a person of ordinary skill in the art. These techniques are fully described in the reference cited in the previous paragraph. Typically, estrogen and progesterone hormones are utilized to synchronize the estrus cycle of the female animal with the developmental cycle of the embryo. The term "developmental cycle" as used herein refers to embryos of the invention and the time period that exists between each cell division within the embryo. This time period is predictable for embryos, and can be synchronized with the estrus cycle of a recipient animal.

The term "culturing" as used herein with respect to embryos refers to laboratory procedures that involve placing an embryo in a culture medium. The embryo can be placed in the culture medium for an appropriate amount of time to allow the embryo to remain static but functional in the medium, or to allow the embryo to grow in the medium. Culture media suitable for culturing embryos are well-known to those skilled in the art. See, e.g., U.S. Pat. No. 5,213,979, entitled "In vitro Culture of Bovine Embryos," First et al., issued May 25, 1993, and U.S. Pat. No. 5,096,822, entitled "Bovine Embryo Medium," Rosenkrans, Jr. et al., issued Mar. 17, 1992, incorporated herein by reference in their entireties including all figures, tables, and drawings.

The term "suitable medium" as used herein refers to any medium that allows cell proliferation. The suitable medium need not promote maximum proliferation, only measurable cell proliferation.

The term "cloned" as used herein refers to a cell, embryonic cell, fetal cell, and/or animal cell having a nuclear DNA sequence that is substantially similar or identical to the nuclear DNA sequence of another cell, embryonic cell, fetal cell, and/or animal cell. The terms "substantially similar" and "identical" are described herein. The cloned embryo can arise from one nuclear transfer, or alternatively, the cloned embryo can arise from a cloning process that includes at least one re-cloning step. If the cloned embryo arises from a cloning procedure that includes at least one re-cloning step, then the cloned embryo can indirectly arise from an immortalized, totipotent cell since the re-cloning step can utilize embryonic cells isolated from an embryo that arose from an immortalized, totipotent cell. The term "totipotent" as used herein in reference to embryos refers to embryos that can develop into a live born animal.

The term "substantially similar" as used herein in reference to nuclear DNA sequences refers to two nuclear DNA sequences that are nearly identical. The two sequences may differ by copy error differences that normally occur during the replication of a nuclear DNA. Substantially similar DNA sequences are preferably greater than 97% identical, more-preferably greater than 98% identical, and most preferably greater than 99% identical. Identity is measured by dividing the number of identical residues in the two sequences by the total number of residues and multiplying the product by 100. Thus, two copies of exactly the same sequence have 100% identity, while sequences that are less highly conserved and have deletions, additions, or replacements have a lower degree of identity. Those of ordinary skill in the art will recognize that several computer programs are available for performing sequence comparisons and determining sequence identity.

The term "parental embryo" is used to refer to an embryo from which a single blastomere is removed or biopsied. Following biopsy, the remaining parental embryo (the parental embryo minus the biopsied blastomere) can be cultured with the blastomere to help promote proliferation of the blastomere. The remaining, viable parental embryo may subsequently be frozen for long term or perpetual storage or for future use. Alternatively, the viable parental embryo may be used to create a pregnancy. Alternatively, the viable parental embryo may be destroyed. In certain embodiments, a parental embryo is a cloned embryo produced by the serial transplantation methods of the invention. In other embodiments, a parental embryo is an embryo produced by fertilization.

Overview

Despite its enormous potential for both basic science and therapeutic use, the efficiency of mammalian cloning by somatic cell nuclear transfer (SCNT) remains low. The birth rate of live young after SCNT is less than 10% regardless of species, donor cell type, protocols, or techniques used. Similarly the development rate of cloned embryos is lower than that of normal fertilized embryos, resulting in poor development to blastocyst and smaller cell number at blastocyst. These deficits also contribute to the relatively less successful ES cell line establishment from cloned mouse embryos, which is approximately 5% irrespective of the mouse strain or donor cell type, compared to approximate 30% success rate when normal embryos are used. The incompetence of the cloned embryos is largely due to incomplete nuclear programming, as manifested by aberrant expression of several genes during early developmental stages.

To overcome the low efficiency of SCNT, several approaches have been tried. Recently, Kishigami et al. (2006) reported an improved mouse cloning technique of treating the reconstructed mouse eggs with trichostatin A, an inhibitor of histone deacetylase, which reduces abnormal DNA hypermethylation. Another approach was serial cloning using either pronuclear (PN) stage zygotes or 2-cell stage in vivo fertilized embryos as second cytoplast recipients. When PN stage mouse somatic cell cloned embryos were recloned into enucleated in vivo fertilized PN stage zygotes, the development of cloned embryos in vitro and live pup rate were improved to some extent. In fact, a similar method was also used successfully in the first swine somatic cell cloning. Two-cell stage in vivo fertilized embryos have also been used for successful serial cloning. When 2-cell stage SCNT embryos were re-cloned into 2-cell stage in vivo embryos, their in vitro development was improved and culminated in live pups. However, none of these studies explored the molecular basis for the improvement, and the nuclear donor cells were either ES cells or pretreated somatic cells. Moreover the improvement in cloned embryo development was not significant. Pretreatment of donor cells has addressed chromatin remodeling and cell cycle synchronization between nuclear donor cells and recipient oocytes, with various methods, which again resulted in somewhat improved cloning efficiency. However, regardless of the methods applied, cloning efficiency still remained too low to be used widely for basic scientific research, practical multiplications of certain strains of mouse, therapeutic cloning, or stem cell derivation. Furthermore, we are unaware of any group employing serial cloning to successfully derive blastocysts or blastocyst-like clusters from which embryonic stem cells may be derived, or successfully deriving embryonic stem cells or stem cell lines. Similarly, we are unaware of any group employing serial cloning to successfully derive morula stage embryos (NT clusters substantially equivalent to and corresponding to morula stage of development). Such morula stage embryos can be used as parental embryos from which one or more blastomeres can be removed or biopsied and used to generate ES cells.

Another aspect of the application uses embryos from which one or more blastomeres can be removed or biopsied and used to generate ES cells.

Methods of Nuclear Transfer

An objective of the present invention is to provide a means of cloning somatic cells more efficiently and without causing ethical concerns. The methods of the disclosure may be used for cloning a mammal, for obtaining pluripotent cells, or for reprogramming a mammalian cell.

Human or animal cells, preferably mammalian cells, may be obtained and cultured by well known methods. Human and animal cells useful in the present invention include, by way of example, epithelial, neural cells, epidermal cells, keratinocytes, hematopoietic cells, melanocytes, chondrocytes, lymphocytes (B and T lymphocytes), other immune cells, erythrocytes, macrophages, melanocytes, monocytes, mononuclear cells, fibroblasts, cardiac muscle cells, cumulus cells and other muscle cells, etc. Moreover, the human cells used for nuclear transfer may be obtained from different organs, e.g., skin, lung, pancreas, liver, stomach, intestine, heart, reproductive organs, bladder, kidney, urethra and other urinary organs, etc. These are just examples of suitable donor cells. Suitable donor cells, i.e., cells useful in the subject invention, may be obtained from any cell or organ of the body. This includes all somatic or germ cells e.g., primordial germ cells, sperm cells. Preferably, the donor cells or nucleus can actively dividing, i.e., non-quiescent, cells as this has been reported to enhance cloning efficacy. Such cells include those in the G1, G2 S or M cell phase. Alternatively, quiescent cells may be used. Also preferably, such donor cells will be in the G1 cell cycle. In certain embodiments, donor and/or recipient cells of the application do not undergo a 2-cell block. In certain embodiments, donor cells or nuclei are not pretreated before nuclear transfer. In certain embodiments, donor cells or nuclei are not pretreated with spermine, protamine, or putrescine before nuclear transfer.

In certain embodiments, recipient fertilized embryos of the invention may be from any mammalian species. In certain embodiments, cryopreserved fertilized embryos are used as recipient cells. In certain embodiments, these embryos are human. Cryogenic preservation and thawing are known to those skilled in the art (see Tucker et al., Curr Opin Obstet Gynecol. 1995 June; 7(3):188-92).

In certain embodiments, donor nuclei may be labeled. Cells may be genetically modified with a transgene encoding a easily visualized protein such as the Green Fluorescent protein (Yang, M., et al., 2000, Proc. Natl. Acad. Sci. USA, 97:1206-1211), or one of its derivatives, or modified with a transgene constructed from the Firefly (*Photinus pyralis*) luciferase gene (*Fluc*) (Sweeney, T. J., et al. 1999, Proc. Natl. Acad. Sci. USA, 96: 12044-12049), or with a transgene constructed from the Sea Pansey (*Renilla reniformis*) luciferase gene (*Rluc*) (Bhaumik, S., and Ghambhir, S. S., 2002, Proc. Natl. Acad. Sci. USA, 99:377-382). The reporter transgenes may be constitutively expressed using a "house-keeping gene" promoter such that the reporter genes are expressed in many or all cells at a high level, or the reporter transgenes may be expressed using a tissue specific or developmental stage specific gene promoter such that only cells that have located into particular niches and developed into specific tissues or cell types may be visualized. Additional labeling reagents include, but are not limited to, luminescently labeled macromolecules including fluorescent protein analogs and biosensors, luminescent macromolecular chimeras including those formed with the green fluorescent protein and mutants thereof, luminescently labeled primary or secondary antibodies that react with cellular antigens involved in a physiological response, luminescent stains, dyes, and other small molecules. Labeled cells from a mosaic blastocyst can be sorted for example by flow cytometry to isolate the cloned population.

Nuclear transfer techniques or nuclear transplantation techniques are known in the literature. See, in particular, Campbell et al, Theriogenology, 43:181 (1995); Collas et al, Mol. Report Dev., 38:264-267 (1994); Keefer et al, Biol. Reprod., 50:935-939 (1994); Sims et al, Proc. Natl. Acad. Sci., USA, 90:6143-6147 (1993); WO 94/26884; WO 94/24274, and WO 90/03432, which are incorporated by reference in their entirety herein. Also, U.S. Pat. Nos. 4,944,384 and 5,057,420 describe procedures for bovine nuclear transplantation. See, also Cibelli et al, Science, Vol. 280:1256-1258 (1998).

Transferring the donor nucleus into a recipient fertilized embryo may be done with a microinjection device. In certain embodiments, minimal cytoplasm is transferred with the nucleus. Transfer of minimal cytoplasm is achievable when nuclei are transferred using microinjection, in contrast to transfer by cell fusion approaches. In one embodiment, the microinjection device includes a piezo unit. Typically, the piezo unit is operably attached to the needle to impart oscillations to the needle. However, any configuration of the piezo unit which can impart oscillations to the needle is included within the scope of the invention. In certain instances the piezo unit can assist the needle in passing into the object. In certain embodiments, the piezo unit may be used to transfer minimal cytoplasm with the nucleus. Any piezo unit suitable for the purpose may be used. In certain embodiments a piezo unit is a Piezo micromanipulator controller PMM150 (PrimeTech, Japan).

Enucleation may be effected by known methods, such as described in U.S. Pat. No. 4,994,384 which is incorporated by reference herein. For example, metaphase II oocytes are either placed in HECM, optionally containing 7.5 micrograms per milliliter cytochalasin B, for immediate enucleation, or may be placed in a suitable medium, for example CR1aa, plus 10% estrus cow serum, and then enucleated later.

Enucleation may be accomplished microsurgically using a micropipette to remove the polar body and the adjacent cytoplasm. The cells may then be screened to identify those of which have been successfully enucleated. This screening may be effected by staining the cells with 1 microgram per milliliter 33342 Hoechst dye in HECM, and then viewing the cells under ultraviolet irradiation for less than 10 seconds. Cells that have been successfully enucleated can then be placed in a suitable culture medium.

There have been very few reports of non-invasive approaches to enucleation in mammals, whereas in amphibians, irradiation with ultraviolet light is used as a routine procedure (Gurdon Q. J. Microsc. Soc. 101 299-311 (1960)). There are no detailed reports of the use of this approach in mammals, although during the use of DNA-specific fluorochrome it was noted that exposure of mouse oocytes to ultraviolet light for more than 30 seconds reduced the developmental potential of the cell (Tsunoda et al., J. Reprod. Fertil. 82 173 (1988)).

The present invention may utilize "induced enucleation" which refers to enucleation of the oocyte by disrupting the meiotic spindle apparatus through the destabilization (e.g., depolymerization) of the microtubules of the meiotic spindle (see U.S. Patent Application No. 20060015950). Destabilization of the microtubules prevents the chromatids from separating (e.g., prevents successful karyokinesis), and induces the oocyte genome (e.g., nuclear chromatin) to segregate unequally (e.g., skew) during meiotic maturation, whereby essentially all endogenous chromatin of the oocyte collects in the second polar body.

In certain embodiments, blastomeres may be dissociated using a glass pipette. In some embodiments, dissociation may occur in the presence of 0.25% trypsin (Collas and Robl, 43 BIOL. REPROD. 877-84, 1992; Stice and Robl, 39 BIOL. REPROD. 657-664, 1988; Kanka et al., 43 MOL. REPROD. DEV. 135-44, 1996).

The NT unit may be activated by known methods. Such methods include, e.g., culturing the NT unit at sub-physiological temperature, in essence by applying a cold, or actually cool temperature shock to the NT unit. This may be most conveniently done by culturing the NT unit at room temperature, which is cold relative to the physiological temperature conditions to which embryos are normally exposed.

Alternatively, activation may be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock or cycloheximide treatment may also be used to activate NT embryos after fusion. Suitable oocyte activation methods are the subject of U.S. Pat. No. 5,496,720, to Susko-Parrish et al., which is herein incorporated by reference.

For example, oocyte activation may be effected by simultaneously or sequentially:
(i) increasing levels of divalent cations in the oocyte, and
(ii) reducing phosphorylation of cellular proteins in the oocyte.

This will generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators.

Phosphorylation may be reduced by known methods, e.g., by the addition of kinase inhibitors, e.g., serine-threonine kinase inhibitors, such as 6-dimethylamino-purine, staurosporine, 2-aminopurine, and sphingosine.

Alternatively, phosphorylation of cellular proteins may be inhibited by introduction of a phosphatase into the oocyte, e.g., phosphatase 2A and phosphatase 2B.

Specific examples of activation methods are listed below.
1. Activation by Ionomycin and DMAP
   1—Place oocytes in Ionomycin (5 uM) with 2 mM of DMAP for 4 minutes;
   2—Move the oocytes into culture media with 2 mM of DMAP for 4 hours;
   3—Rinse four times and place in culture.
2. Activation by Ionomycin DMAP and Roscovitin
   1—Place oocytes in Ionomycin (5 uM) with 2 mM of DMAP for four minutes;
   2—Move the oocytes into culture media with 2 mM of DMAP and 200 microM of Roscovitin for three hours;
   3—Rinse four times and place in culture.
3. Activation by exposure to Ionomycin followed by cytochalasin and cycloheximide.
   1—Place oocytes in Ionomycin (5 microM) for four minutes;
   2—Move oocytes to culture media containing 5 ug/ml of cytochalasin B and 5 .mu.g/ml of cycloheximide for five hours;
   3—Rinse four times and place in culture.
4. Activation by electrical pulses
   1—Place eggs in mannitol media containing 100 uM $CaCl_2$;
   2—Deliver three pulses of 1.0 kVcm$^{-1}$ for 20 usec, each pulse 22 minutes apart;
   3—Move oocytes to culture media containing 5 ug/ml of cytochalasin B for three hours.
5. Activation by exposure with ethanol followed by cytochalasin and cycloheximide
   1—Place oocytes in 7% ethanol for one minute;
   2—Move oocytes to culture media containing 5 ug/ml of cytochalasin B and 5 ug/ml of cycloheximide for five hours;
   3—Rinse four times and place in culture.
6. Activation by microinjection of adenophostine
   1—Inject oocytes with 10 to 12 picoliters of a solution containing 10 uM of adenophostine;
   2—Put oocytes in culture.
7. Activation by microinjection of sperm factor
   1—Inject oocytes with 10 to 12 picoliters of sperm factor isolated, e.g., from primates, pigs, bovine, sheep, goats, horses, mice, rats, rabbits or hamsters;
   2—Put eggs in culture.
8. Activation by microinjection of recombinant sperm factor.
9. Activation by Exposure to DMAP followed by cycloheximide and cytochalasin B
10. Activation by Exposure to $SrCl_2$ and cytochalasin B.

In certain embodiments, oocytes or NT units, typically about 22 to 28 hours post maturation are placed in about 2 mM DMAP for about one hour, followed by incubation for about two to twelve hours, preferably about eight hours, in 5 pg/ml of cytochalasin B and 20 ug/ml cycloheximide.

In certain embodiments, the activation of reconstructed oocytes is carried out in $Ca^{++}$-free CZB containing 10 mM $SrCl_2$ and 5 μg/ml cytochalasin B for 6 hrs in a high humidified 5.5% $CO_2$ incubator.

As noted, activation may be effected before, simultaneous, or after nuclear transfer. In general, activation will be effected about 40 hours prior to nuclear transfer and fusion to about 40 hours after nuclear transfer and fusion, more preferably about 24 hours before to about 24 hours after nuclear transfer and fusion, and most preferably from about 4 to 9 hours before nuclear transfer and fusion to about 4 to 9 hours after nuclear transfer and fusion. Activation is preferably effected after or proximate to in vitro or in vivo maturation of the oocyte, e.g., approximately simultaneous or within about 40 hours of maturation, more preferably within about 24 hours of maturation.

In certain embodiments, a step of the present invention is to fuse the cloned nuclei with enucleated cytoplasts of germ-line cells such as blastomeres, morula cells, inner cell mass cells, ES cells, including hES cells, EG cells, EC cells as is known in the art (Do & Scholer, Stem Cells 22:941-949 (2004)). Fusion of the cytoplasts with the nuclei is performed using a number of techniques known in the art, including polyethylene glycol (see Pontecorvo "Polyethylene Glycol (PEG) in the Production of Mammalian Somatic Cell Hybrids" Cytogenet Cell Genet. 16(1-5):399-400 (1976), the direct injection of nuclei, Sendai viral-mediated fusion (see U.S. Pat. No. 4,664,097 and Graham Wistar Inst. Symp. Monogr. 9 19 (1969)), or other techniques known in the art such as electrofusion. Electrofusion of cells involves bringing cells together in close proximity and exposing them to an alternating electric field. Under appropriate conditions, the cells are pushed together and there is a fusion of cell membranes and then the formation of fusate cells or hybrid cells. Electrofusion of cells and apparatus for performing same are described in, for example, U.S. Pat. Nos. 4,441,972, 4,578,168 and 5,283,194, International Patent Application No. PCT/AU92/00473 [WO 93/05166], Pohl, "Dielectrophoresis", Cambridge University Press, 1978 and Zimmerman et al., Biochimica et Bioplzysica Acta 641: 160-165, 1981.

Fusion of the cloned nuclei with anucleate cytoplasmic blebs of germ-line cells, such as hES cells attached to a physical substrate as is well known in the art (Wright & Hayflick, Exp. Cell Res. 96:113-121, (1975); & Wright & Hayflick, Proc. Natl. Acad. Sci., USA, 72:1812-1816, (1975) may be combined with the present disclosure. Briefly, the cytoplasmic volume of the germ-line cells is increased by adding 10 μM cytochalasin B for 20 hours prior to manipulation. trypsinized and replated on sterile 18 mm coverslips, cylinders, or other physical substrate coated with material promoting attachment. The cells are plated at a density such that after an overnight incubation at 37° C. and one gentle wash with medium, the cells cover a portion, preferably about 90% of the surface area of the coverslip or other substrate. The substrates are then placed in a centrifuge tube in a position such that centrifugation will result in the removal of the nuclei from the cytoplast containing 8 mL of 10% Ficoll-400 solution and centrifuged at 20,000 g at 36° C. for 60 minutes. Cloned nuclei are then spread onto the coverslip or substrate with a density of at least that of the cytoplasts, preferable at least five times the density of the cytoplasts. Fusion of the cytoplasts with the nuclei is performed using polyethylene glycol (see Pontecorvo "Polyethylene Glycol (PEG) in the Production of Mammalian Somatic Cell Hybrids" Cytogenet Cell Genet. 16(1-5):399-400 (1976). Briefly, in 1 mL of prewarmed 50% polyethylene glycol 1500 (Roche) in culture medium is placed over the coverslip or substrate for one minute. 20 mL of culture medium is then added drip-wise over a five minute period to slowly remove the polyethylene glycol. The entire media is then aspirated and replaced with culture medium. Techniques other than centrifugation such as vibration or physical removal of the nuclei using a micropipette may also be used.

It has been suggests that embryos derived by nuclear transfer are different from normal embryos and sometimes benefit from or even require culture conditions in vivo other than those in which embryos are usually cultured (at least in vivo). The reason for this is not known. In routine multiplication of bovine embryos, reconstituted embryos (many of them at once) have been cultured in sheep oviducts for 5 to 6 days (as described by Willadsen, In Mammalian Egg Transfer (Adams, E. E., ed.) 185 CRC Press, Boca Raton, Fla. (1982)). In certain embodiments, the embryo may be embedded in a protective medium such as agar before transfer and then dissected from the agar after recovery from the temporary recipient. The function of the protective agar or other medium is twofold: first, it acts as a structural aid for the embryo by holding the zona pellucida together; and secondly it acts as barrier to cells of the recipient animal's immune system. Although this approach increases the proportion of embryos that form blastocysts, there is the disadvantage that a number of embryos may be lost.

Activated NT units may be cultured in a suitable in vitro culture medium until the generation of embryonic or stem-like cells and cell colonies. Culture media suitable for culturing and maturation of embryos are well known in the art. Examples of known media, which may be used for bovine embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media. One of the most common media used for the collection and maturation of oocytes is TCM-199, and 1 to 20% serum supplement including fetal calf serum, newborn serum, estrual cow serum, lamb serum or steer serum. A preferred maintenance medium includes TCM-199 with Earl salts, 10% fetal calf serum, 0.2 Ma pyruvate and 50 ug/ml gentamicin sulphate. Any of the above may also involve co-culture with a variety of cell types such as granulosa cells, oviduct cells, BRL cells and uterine cells and STO cells.

In particular, human epithelial cells of the endometrium secrete leukemia inhibitory factor (LIF) during the preimplantation and implantation period. Therefore, the addition of LIF to the culture medium could be of importance in enhancing the in vitro development of the reconstructed embryos. The use of LIF for embryonic or stem-like cell cultures has been described in U.S. Pat. No. 5,712,156, which is herein incorporated by reference.

Another maintenance medium is described in U.S. Pat. No. 5,096,822 to Rosenkrans, Jr. et al., which is incorporated herein by reference. This embryo medium, named CR1, contains the nutritional substances necessary to support an embryo. CR1 contains hemicalcium L-lactate in amounts ranging from 1.0 mM to 10 mM, preferably 1.0 mM to 5.0 mM. Hemicalcium L-lactate is L-lactate with a hemicalcium salt incorporated thereon.

Also, suitable culture medium for maintaining human embryonic cells in culture as discussed in Thomson et al., Science, 282:1145-1147 (1998) and Proc. Natl. Acad. Sci., USA, 92:7844-7848 (1995).

Afterward, the cultured NT unit or units are preferably washed and then placed in a suitable media, e.g., CR1aa medium, Ham's F-10, Tissue Culture Media-199 (TCM-199). Tyrodes-Albumin-Lactate-Pyruvate (TALP) Dulbecco's Phosphate Buffered Saline (PBS), Eagle's or Whitten's, preferably containing about 10% FCS. Such culturing will preferably be effected in well plates which contain a suitable confluent feeder layer. Suitable feeder layers include, by way of example, fibroblasts and epithelial cells, e.g., fibroblasts and uterine epithelial cells derived from ungulates, chicken fibroblasts, murine (e.g., mouse or rat) fibroblasts, STO and SI-m220 feeder cell lines, and BRL cells.

In a preferred embodiment, the feeder cells will comprise mouse embryonic fibroblasts. Means for preparation of a suitable fibroblast feeder layer are described in the example which follows and is well within the skill of the ordinary artisan.

Methods of deriving ES cells from blastocyst-stage embryos (or the equivalent thereof) are well known in the art. Such techniques can be used to derive ES cells from cloned embryos. Additionally or alternatively, ES cells can be derived from cloned embryos during earlier stages of development.

Applications

In certain embodiments, the resultant blastocysts, or blastocyst-like clusters, of the disclosure may be used to obtain embryonic stem cell lines. Such lines can be obtained, for example, according to the culturing methods reported by Thomson et al., Science, 282:1145-1147 (1998) and Thomson et al., Proc. Natl. Acad. Sci., USA, 92:7544-7848 (1995), incorporated by reference in their entirety herein.

Pluripotent embryonic stem cells can also be generated from a single blastomere removed from an embryo without interfering with the embryo's normal development to birth. See U.S. application Nos. 60/624,827, filed Nov. 4, 2004; 60/662,489, filed Mar. 14, 2005; 60/687,158, filed Jun. 3, 2005; 60/723,066, filed Oct. 3, 2005; 60/726,775, filed Oct. 14, 2005; 11/267,555 filed Nov. 4, 2005; PCT application no. PCT/US05/39776, filed Nov. 4, 2005, the disclosures of which are incorporated by reference in their entirety; see also Chung et al., Nature, Oct. 16, 2005 (electronically published ahead of print) and Chung et al., Nature V. 439, pp. 216-219 (2006), the entire disclosure of each of which is incorporated by reference in its entirety).

In one aspect of the invention, the method comprises the utilization of cells derived from the reprogrammed cells of the present invention in research and in therapy. Such reprogrammed pluripotent or totipotent cells may be differentiated into any of the cells in the body including, without limitation, skin, cartilage, bone, skeletal muscle, cardiac muscle, renal, hepatic, blood and blood forming, vascular precursor and vascular endothelial, pancreatic beta, neurons, glia, retinal, inner ear follicle, intestinal, lung, cells.

In particular, the reprogrammed cells may be differentiated into cells with a dermatological prenatal pattern of gene expression that is highly elastogenic or capable of regeneration without causing scar formation. Dermal fibroblasts of mammalian fetal skin, especially corresponding to areas where the integument benefits from a high level of elasticity, such as in regions surrounding the joints, are responsible for synthesizing de novo the intricate architecture of elastic fibrils that function for many years without turnover. In addition, early embryonic skin is capable of regenerating without scar formation. Cells from this point in embryonic development made from the reprogrammed cells of the present invention are useful in promoting scarless regeneration of the skin including forming normal elastin architecture. This is particularly useful in treating the symptoms of the course of normal human aging, or in actinic skin damage, where there can be a profound elastolysis of the skin resulting in an aged appearance including sagging and wrinkling of the skin.

In another embodiment of the invention, the reprogrammed cells are exposed to one or more inducers of differentiation to yield other therapeutically-useful cells such as retinal pigment epithelium, hematopoietic precursors and hemangioblastic progenitors as well as many other useful cell types of the ectoderm, mesoderm, and endoderm. Such inducers include but are not limited to: cytokines such as interleukin-alpha A, interferon-alpha A/D, interferon-beta, interferon-gamma, interferon-gamma-inducible protein-10, interleukin-1-17, keratinocyte growth factor, leptin, leukemia inhibitory factor, macrophage colony-stimulating factor, and macrophage inflammatory protein-1 alpha, 1-beta, 2, 3 alpha, 3 beta, and monocyte chemotactic protein 1-3, 6kine, activin A, amphiregulin, angiogenin, B-endothelial cell growth factor, beta cellulin, brain-derived neurotrophic factor, C10, cardiotrophin-1, ciliary neurotrophic factor, cytokine-induced neutrophil chemoattractant-1, eotaxin, epidermal growth factor, epithelial neutrophil activating peptide-78, erythropoietin, estrogen receptor-alpha, estrogen receptor-beta, fibroblast growth factor (acidic and basic), heparin, FLT-3/FLK-2 ligand, glial cell line-derived neurotrophic factor, Gly-His-Lys, granulocyte colony stimulating factor, granulocytemacrophage colony stimulating factor, GRO-alpha/MGSA, GRO-beta, GRO-gamma, HCC-1, heparin-binding epidermal growth factor, hepatocyte growth factor, heregulin-alpha, insulin, insulin growth factor binding protein-1, insulin-like growth factor binding protein-1, insulin-like growth factor, insulin-like growth factor II, nerve growth factor, neurotophin-3,4, oncostatin M, placenta growth factor, pleiotrophin, rantes, stem cell factor, stromal cell-derived factor 1B, thromopoietin, transforming growth factor—(alpha, beta 1,2, 3,4,5), tumor necrosis factor (alpha and beta), vascular endothelial growth factors, and bone morphogenic proteins, enzymes that alter the expression of hormones and hormone antagonists such as 17B-estradiol, adrenocorticotropic hormone, adrenomedullin, alpha-melanocyte stimulating hormone, chorionic gonadotropin, corticosteroid-binding globulin, corticosterone, dexamethasone, estriol, follicle stimulating hormone, gastrin 1, glucagons, gonadotropin, L-3,3',5'-triiodothyronine, leutinizing hormone, L-thyroxine, melatonin, MZ-4, oxytocin, parathyroid hormone, PEC-60, pituitary growth hormone, progesterone, prolactin, secretin, sex hormone binding globulin, thyroid stimulating hormone, thyrotropin releasing factor, thyroxin-binding globulin, and vasopressin, extracellular matrix components such as fibronectin, proteolytic fragments of fibronectin, laminin, tenascin, thrombospondin, and proteoglycans such as aggrecan, heparan sulphate proteoglycan, chontroitin sulphate proteoglycan, and syndecan. Other inducers include cells or components derived from cells from defined tissues used to provide inductive signals to the differentiating cells derived from the reprogrammed cells of the present invention. Such inducer cells may derive from human, nonhuman mammal, or avian, such as specific pathogen-free (SPF) embryonic or adult cells.

In certain embodiments of the invention, cloned cells are introduced into the tissues in which they normally reside in order to exhibit therapeutic utility. For example, the clonogenic populations of cells derived by methods of this invention may be introduced into the tissues. In certain other embodiments, cloned cells are introduced systemically or at a distance from the cite at which therapeutic utility is desired. In such embodiments, the cloned cells may act at a distance or may hone to the desired cite.

In certain embodiments of the invention, cloned cells, derived by methods of this invention, are utilized in inducing the differentiation of other pluripotent stem cells. The generation of single cell-derived populations of cells capable of being propagated in vitro while maintaining an embryonic pattern of gene expression is useful in inducing the differentiation of other pluripotent stem cells. Cell-cell induction is a common means of directing differentiation in the early embryo. Many potentially medically-useful cell types are influenced by inductive signals during normal embryonic development including spinal cord neurons, cardiac cells, pancreatic beta cells, and definitive hematopoietic cells. Single cell-derived populations of cells capable of being propagated in vitro while maintaining an embryonic pattern of gene expression can be cultured in a variety of in vitro, in ovo, or in vivo culture conditions to induce the differentiation of other pluripotent stem cells to become desired cell or tissue types.

The subject embryonic or stem-like cells may be used to obtain any desired differentiated cell type. Therapeutic usages of such differentiated human cells are unparalleled. For example, human hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by fusing adult somatic cells of a cancer or AIDS patient, e.g., epithelial cells or lymphocytes with an enucleated oocyte, e.g., bovine oocyte, obtaining embryonic or stem-like cells as described above, and culturing such cells under conditions which favor differentiation, until hematopoietic stem cells are obtained. Such hematopoietic cells may be used in the treatment of diseases including cancer and AIDS.

Alternatively, adult somatic cells from a patient with a neurological disorder may be fused with an enucleated animal oocyte, e.g., a primate or bovine oocyte, human embryonic or stem-like cells obtained therefrom, and such cells cultured under differentiation conditions to produce neural cell lines. Specific diseases treatable by transplantation of such human neural cells include, by way of example, Parkinson's disease, Alzheimers disease, ALS and cerebral palsy, among others. In the specific case of Parkinson's disease, it has been demonstrated that transplanted fetal brain neural cells make the proper connections with surrounding cells and produce dopamine. This can result in long-term reversal of Parkinson's disease symptoms.

To allow for specific selection of differentiated cells, donor cells may be transfected with selectable markers expressed via inducible promoters, thereby permitting selection or enrichment of particular cell lineages when differentiation is induced. For example, CD34-neo may be used for selection of hematopoietic cells, Pw1-neo for muscle cells, Mash-1-neo for sympathetic neurons, Mal-neo for human CNS neurons of the grey matter of the cerebral cortex, etc.

The great advantage of the subject invention is that it provides an essentially limitless supply of isogenic or synegenic human cells suitable for transplantation. Therefore, it will obviate the significant problem associated with current transplantation methods, i.e., rejection of the transplanted tissue which may occur because of host-vs-graft or graft-vs-host rejection. Conventionally, rejection is prevented or reduced by the administration of anti-rejection drugs such as cyclosporin. However, such drugs have significant adverse side-effects, e.g., immunosuppression, carcinogenic properties, as well as being very expensive. The present invention should eliminate, or at least greatly reduce, the need for anti-rejection drugs, such as cyclosporine, imulan, FK-506, glucocorticoids, and rapamycin, and derivatives thereof.

Other diseases and conditions treatable by isogenic cell therapy include, by way of example, spinal cord injuries, multiple sclerosis, muscular dystrophy, diabetes, liver diseases, i.e., hypercholesterolemia, heart diseases, cartilage replacement, burns, foot ulcers, gastrointestinal diseases, vascular diseases, kidney disease, urinary tract disease, and aging related diseases and conditions.

Methods for cloning a mammal from a cloned embryo are well known in the art The two main procedures used for cloning mammals are the Roslin method and the Honolulu method. These procedures were named after the generation of Dolly the sheep at the Roslin Institute in Scotland in 1996 (Campbell, K. H. et al. (1996) Nature 380:64-66) and of Cumulina the mouse at the University of Hawaii in Honolulu in 1998 (Wakayama, T. et al. (1998) Nature 394:369-374).

In other embodiments, the methods of the invention can be used to produce cloned cleavage stage embryos or morula stage embryos that can be used as parental embryos. Such parental embryos can be used to generate ES cells. For example, a blastomere (1, 2, 3, 4 blastomeres) can be removed or biopsied from such parental embryos and such blastomeres can be used to derive ES cells.

Blastomere Culturing

Previous attempts to induce isolated human blastomeres to proliferate into pluripotent embryonic stem cells have failed (Geber S. et al., *Hum. Reprod.* 10:1492-1496 (1995)). The present invention is based, in part, on the discovery that stem cells can be generated from embryos without affecting viability of the embryo using novel methods disclosed herein. In one embodiment, these methods utilize in vitro techniques related to those currently used in pre-implantation genetic diagnosis (PGD) to isolate single blastomeres from embryos without destroying the embryos or otherwise significantly altering their viability. As demonstrated herein, pluripotent human embryonic stem (hES) cells and cell lines can be generated from a single blastomere removed from an embryo without interfering with the embryo's normal development to birth.

The methods described herein have numerous important uses that will advance the field of stem cell research and developmental biology. ES cells, ES cell lines, TS cells and cell lines, and cells differentiated therefrom can be used to study basic developmental biology, and can be used therapeutically in the treatment of numerous diseases and conditions. Additionally, these cells can be used in screening assays to identify factors and conditions that can be used to modulate the growth, differentiation, survival, or migration of these cells. Identified agents can be used to regulate cell behavior in vitro and in vivo, and may form the basis of cellular or cell-free therapies.

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the invention or testing of the present invention, suitable methods and materials are described below. The materials, methods and examples are illustrative only, and are not intended to be limiting.

All publications, patents, patent publications and applications and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The articles "a" and "an" are used herein to refer to one or to more than one (i.e., to at least one) of the grammatical object of the article. By way of example, "an element" means one element or more than one element.

The term "blastomere" is used throughout to refer to at least one blastomere (e.g., 1, 2, 3, 4, etc) obtained from an embryo. The term "cluster of two or more blastomeres" is used interchangeably with "blastomere-derived outgrowths" to refer to the cells generated during the in vitro culture of a blastomere. For example, after a blastomere is obtained from an embryo and initially cultured, it generally divides at least once to produce a cluster of two or more blastomeres (also known as a blastomere-derived outgrowth). The cluster can be further cultured with embryonic or fetal cells. Ultimately, the blastomere-derived outgrowths will continue to divide. From these structures, ES cells, TS cells, and partially differentiated cell types will develop over the course of the culture method.

As summarized above, the present invention provides methods for deriving ES cells, ES cell lines, and differentiated cell types from single blastomeres of an early stage embryo without necessarily destroying the embryo. Various features of the method a described in detail below. All of the combinations of the various aspects and embodiments of the invention detailed above and below are contemplated.

Removal of the Blastomere

The blastomere may be removed from an embryo at various developmental stages prior to implantation including but not limited to: before compaction of the morula, during compaction of the morula, right after compaction of the morula, before formation of the blastocoel or during the blastocyst stage. In certain embodiments, a blastomere (one blastomere, two blastomeres, or more than two blastomeres) is removed from an embryo at the 4-16 cell stage, or at the 4-10 cell stage, or at the 4-8 cell stage.

In one embodiment the invention provides methods for biopsy of a blastocyst which will produce embryonic stem cells, and the remainder of the blastocyst is implanted and results in a pregnancy and later in a live birth. In an example of this: the zona pellucida is removed from the blastocyst by any means known to those of ordinary skill in the art and then the blastocyst is biopsied.

In another embodiment the controversies associated with the derivation of human ES cells are circumvented by using a technique similar to that used in preimplantation genetic diagnosis (PGD) where a single blastomere is removed from the embryo. In one embodiment, the single blastomere is removed before the compaction of the morula. The biopsied blastomere could be allowed to undergo cell division and one progeny cell is used for genetic testing and the remaining cells are used to generate human stem cells. The biopsied embryo may also be implanted at the blastocyst stage or frozen for implantation at a later time.

In certain embodiments, biopsy (e.g., removal of a blastomere from an embryo) consists of two stages. The first is to make a hole in, or in some instances fully remove, the zone pellucida that surrounds the embryo. Once the hole is made, the cells (preferably one or two) may then be removed from the human embryo. In certain preferred embodiments, the method involves removing or generating an extraction hole in the zona pellucida, and can be carried out by one or more techniques such as physical manipulation, chemical treatment and enzymatic digestion. Exemplary techniques that could be used include:

Partial zone dissection (PZD:): partial dissection of the zona pellucida, using a micro-pipette;

Zona drilling: chemical opening of the zona pellucida zone through partial digestion with Tyrode acid;

Zona drilling: enzymatic opening of the zona pellucida zone through partial digestion with pronase or other protease;

zona pellucida thinning: thinning of the zona pellucida with Tyrode acid or laser;

Point-like opening of the zona pellucida with laser;

Point-like mechanical opening of the zona pellucida with Piezo micro-manipulator.

To briefly illustrate one embodiment, the procedure is performed on 8-10 cell stage embryos. The embryo is placed in a drop of biopsy medium under mineral oil by holding it with a holding pipette. The zona pellucida is locally digested, by releasing acidified Tyrode's solution (Sigma, St. Louis, Mo. 63178) through an assistant hatching pipette. Once the hole is made, cells (blastomeres) could be aspirated through the hole.

To illustrate another embodiment, the zona pellucida of the blastocyst may be at least partially digested by treatment with one or more enzymes or mixture of enzymes such as pronase. A brief pronase (Sigma) treatment of blastocysts with an intact zona pellucida results in the removal of the zona. Other types of proteases with the same or similar protease activity as pronase may also be used.

Single blastomeres may also be obtained by disaggregating zona-denuded embryos in $Ca^{++}$/$Mg^{++}$ free PBS.

This invention also provides a novel and more efficient method of isolating single blastomeres. The embryo is immobilized and the immobilized embryo is then tapped until a single blastomere is released from the blastocyst. This method is not limited to human embryos and can be performed on embryos of other species including, without limitation, non-human embryos such as non-human mammals, mice, rabbits, pigs, cows, sheep, dogs and primates.

The embryo can be immobilized by any means known to those of skill in the art. In one embodiment, the embryo is immobilized using a micropipette and the micropipette holder is tapped to isolate the blastomere. In another embodiment, the embryo is cultured in medium that is calcium and magnesium free. The embryo may be from the 2-cell stage to the 16 cell stage. In one embodiment, the embryo is from the 4 cell stage to the 10 cell stage. In another embodiment the embryo is a 6-8 cell stage embryo. In yet another embodiment, the embryo is an 8-10 cell stage embryo. In certain embodiments, tapping involves generating an amount of force sufficient to remove at least one blastomere without substantially decreasing the viability of the remainder of the embryo. Maintenance of viability can be shown, for example, by culturing the remaining embryo for at least one day and confirming that the remaining embryo can continue to divide in culture.

Any of the foregoing methods can be used to obtain a blastomere (one blastomere or more than one blastomere) from an embryo. A particular method can be used alone or in combination with another method to facilitate removal of a blastomere.

In certain embodiments, the embryo is a mammalian embryo. In certain embodiments, the mammalian embryo is a human embryo. Exemplary mammals include, but are not limited to, mice, rats, rabbits, cows, dogs, cats, sheep, hamsters, pigs, non-human primates, and humans.

In certain embodiments of any of the foregoing, a blastomere is removed from an embryo without destroying the remainder of the embryo. The remaining embryo (the embryo minus the removed blastomere) can be cultured and/or cryopreserved. In certain embodiments, the remaining embryo is cultured for a time sufficient to confirm that the remaining embryo can continue to divide (e.g., is still viable), and then once viability is confirmed, the remaining embryo is cryopreserved. In certain other embodiments, the remaining embryo is immediately cryopreserved.

In certain other embodiments, multiple blastomeres are removed from a single embryo and the embryo is destroyed during or subsequent to the removal of multiple blastomeres. Multiple blastomeres can be used together in one experiment, for example, by aggregating multiple blastomeres during the initial blastomere culture. Alternatively, multiple blastomeres can be used in separate experiments in an effort to maximize the number of lines or cell types than can be generated from a single embryo.

Embryos from which a blastomere is obtained can be generated by sexual or asexual methods. In certain embodiments, the embryo is produced by fertilization of an egg with a sperm. In certain other embodiments, the embryo is produced by somatic cell nuclear transfer, parthenogenesis, androgenesis, or other asexual techniques. Note that embryos derived from asexual techniques may not look identical to embryos generated by fertilization. However, despite any differences in appearance, the term embryo is intended to encompass the products of asexual reproduction and the products of fertilization or other means of sexual reproduction.

Culturing the Blastomere and Production of ES cells

Once removed from the embryo, the isolated blastomere(s) can be initially cultured in any type of medium, e.g., embryo medium such as Quinn's cleavage medium (Cooper Surgical Inc. Cat #ART1529). Any medium that supports growth of an embryo can be used, including, without limitation, any commercial formulations. As used herein, the term "embryo medium" is used to refer to a medium that promotes survival of blastomeres (especially human blastomeres) in culture. In certain embodiments, the embryo medium is a medium containing less than 5 mM glucose. In certain embodiments, the embryo medium is a medium that has an osmolarity of less that 310 mosm. In certain other embodiments, the embryo medium is a medium that contains less than 5 mM glucose and has an osmolarity of less than 310 mosm. In certain embodiments, the medium used to initially culture blastomeres has an osmolarity of less than 300 mosm, less than 280 mosm, or less than 260 mosm, and optionally contains less than 5 mM glucose. In certain embodiments, the medium used to initially culture blastomeres has an osmolarity about 260-280 mosm, and optionally contains less than 5 mM glucose. Note that regardless of the osmolarity and particular concentration of glucose in the medium used to initially culture the blastomeres, the medium may also be supplemented with antibiotics, minerals, amino acids, and other factors typically found in commercial media formulations.

The blastomeres may not initially grow well in standard ES cell medium. However, as described in detail herein, once the blastomeres have been cultured in the presence of certain embryonic or fetal cells and/or allowed to divide one or more times, the cluster of blastomeres can optionally be cultured in ES cell medium, or may be slowly transferred from embryo medium to ES cell medium by gradually replacing the medium. As used herein, the term "ES cell medium" is used to refer to a medium that promotes maintenance of ES cells in culture and can be used to culture clusters of blastomeres as they continue to divide and produce ES cells, ED cells, etc. Such a medium is at least somewhat optimized for ES cells. In certain embodiments, the ES cell medium contains at least 5 mM glucose (relatively high glucose). In certain other embodiments, the ES cell medium has an osmolarity of at least 310 mosm. In certain other embodiments, the medium contains at least 5 mM glucose and has an osmolarity of at least 310 mosm. In certain embodiments, this medium has an osmolarity of at least 320 mosm, or at least 330 mosm, and optionally contains at least 5 mM glucose. In certain embodiments, this medium has an osmolarity of about 310-340 mosm, and optionally contains at least 5 mM glucose. ES cell medium may also be supplemented with factors known in the art to promote the growth of ES cells, and the medium may contain antibiotics, minerals, amino acids, and other factors typically found in commercial media formulations. In certain embodiments, pronuclear stage human embryos are cultured in Quinn's cleavage medium (Cooper Surgical).

In certain embodiments, pronuclear stage human embryos are cultured up to the 8-cell stage. In certain embodiments, the pronuclear stage embryos may be cultured up to about the 2-cell stage, 4-cell stage, or 16-cell stage. In certain embodiments, the pronuclear stage embryos may be cultured up to between the 2-cell stage and 4-cell stage, 2-cell stage and 8-cell stage, 2-cell stage and 16-cell stage, 4-cell stage and 8-cell stage, 4-cell stage and 16-cell stage, or 8-cell stage and 16-cell stage. In certain embodiments, the embryos are pre-incubated in $Ca^{++}$ and $Mg^{++}$-free phosphate buffered saline supplemented with 0.05% PVA. In certain embodiments, the embryos are pre-incubated for about 5, 10, 15, 20, 25, 30, 5-10, 5-15, 5-30, 10-15, 10-30, or 15-30 min at room temperature. In certain embodiments, the embryos are transferred to Quinn's hepes medium for the manipulation.

In certain embodiments, individual blastomeres are isolated from embryos using PIEZO. In certain embodiments, before inserting a biopsy pipette, a hole (500 μm in diameter) is made on the zona pellucida. In certain embodiments, the hole may be made using a small (20 μm) pipette by applying several pulses of PIEZO. In certain embodiments, a biopsy pipette (500 μm) is inserted through the hole to grasp a blastomere applying gentle negative pressure. In certain embodiments, the blastomeres is pulled away when ⅔ of the blastomere is inside of the pipette. In certain embodiments, ⅓, ½, or ¾ of the blastomere is inside the pipette. In certain embodiments, ⅓ to ½, ⅓ to ⅔, ⅓ to ¾, ½ to ⅔, ½ to ¾, or ⅔ to ¾ of the blastomere is inside the pipette.

In certain embodiments, after the biopsy, the parental embryos and blastomeres may be returned to the original culture drops (Quinn's cleavage medium) and cultured 12 to 18 hrs together. In certain embodiments, after the biopsy, the parental embryos and blastomeres may be returned to the original culture drops (Quinn's cleavage medium) and cultured about 6 to 12, 6 to 18, 6 to 24, 12 to 18, 12 to 24, or 18 to 24 hrs together. In certain embodiments, the parental embryos are transferred to blastocyst medium (Quinn's blastocyst medium). In certain embodiments, the blastomeres are transferred to a small culture drop (50 μl) containing MEFs. In certain embodiments, the blastomere culture medium may be supplemented with laminin, fibronectin, or Matrigel. In certain embodiments, the blastomeres are cultured for about 3, 4, 5, 6, 7 or 8 days. In certain embodiments, the blastomeres are cultured until they form cell clumps composed of approximately 20 cells in the same medium. In certain embodiments, GFP ES cell culture drops may be merged with the blastomere culture drops to allow the two media to mix together. In certain embodiments, some or all of the blastomere clumps may be removed and plated in the same culture drop about 12, 18, 24, 36 or 48 hrs later.

In certain embodiments, a blastomere is obtained from a human or other mammalian embryo and cultured in embryo medium. Preferably, a blastomere is cultured in embryo medium for at least one day or until the blastomere divides at least once. However, a blastomere may be cultured in embryo medium for more than 1 day (at least 2, 3, 4 days, etc.) and/or the blastomere may be cultured in contact with embryonic or fetal cells before dividing to produce a cluster of blastomere. When cultured in embryo medium, the blastomere may divide one or more times or produce a cluster of two or more blastomeres. Further culturing of the cluster of blastomeres includes culturing the blastomere along with its progeny. In certain embodiments, the blastomere divides and the progeny are cultured as an aggregate.

In one embodiment, the blastomere can be cultured in a microdrop. Each microdrop can contain a single blastomere or multiple blastomeres. After about at least 1 day, at least 2-3 days, or at least 4 days, the cultured blastomeres may divide and form vesicles or aggregates. The benefit of culturing the blastomere prior to direct or indirect contact with the embryonic cells is to prevent the embryonic cells from overgrowing the blastomere.

After a blastomere is initially cultured to generate a cluster of two or more blastomeres, the cultured cluster of two or more blastomeres is contacted directly or indirectly with embryonic or fetal cells, or alternatively with a medium that promotes further maturation of the blastomeres in the absence of embryonic or fetal cells. Such medium includes medium conditioned with embryonic or fetal cells (conditioned medium) or medium supplemented with growth factors or cytokines that promote maturation of the blastomeres. In certain embodiments, the medium is supplemented with ACTH (adrenocorticotropic hormone).

For embodiments in which direct or indirect culture with embryonic or fetal cells is used, the embryonic or fetal cells may be derived from, for example, a mammal. In certain embodiments, the embryonic or fetal cells are mouse or human cells. Exemplary embryonic or fetal cells include, but are not limited to, embryonic stem (ES) cells (whether derived from blastocysts, blastomeres, or by other methods, and whether derived using somatic cell nuclear transfer or other asexual reproduction), embryonic germ cells, embryonic carcinoma cells, placental cells, trophoblasts/trophectoderm cells, trophoblast stem cells, primordial germ cells embryonic germ cells, amniotic fluid cells, amniotic stem cells, placental cells, placental stem cells, and umbilical cord cells. In certain embodiments in which blastomeres are directly or indirectly contacted with embryonic or fetal cells, the medium in which the blastomeres are cultured is further supplemented with ACTH or other growth factors or cytokines that promote maturation of the blastomeres.

When used, the embryonic or fetal cells, may be grown in the presence or absence of a feeder layer of cells. Feeder cells may be used to help maintain the embryonic or fetal cells and to prevent their differentiation. The specific feeder cell may be chosen based on the particular embryonic or fetal cell used. Exemplary feeder cells include, but are not limited to, fibroblast feeder cells. Such fibroblast feeder cells may be derived from the same species as the embryonic or fetal cells or they may be derived from a different species. Similarly, the feeder cells and the embryonic or fetal cells may be derived from the same species as the blastomere or from a different species. In certain embodiments, the feeder cells are irradiated or otherwise treated to prevent overgrowth relative to the embryonic or fetal cells. Exemplary feeder cells include, but are not limited to, mouse embryonic fibroblasts (MEF cells), human embryonic fibroblasts, human foreskin fibroblasts, human skin fibroblasts, human endometrial fibroblasts, human oviductal fibroblasts, and placental cells. Similar cell types derived from other animals (mammals, chickens, etc) are also contemplated.

In one embodiment, the feeder and/or embryonic cells are human cells that are autologous cells derived from the same embryo as the blastomere.

The embryonic or fetal cells are grown in ES cell medium or any medium that supports growth of the embryonic or fetal cells, e.g., Knockout DMEM (Invitrogen Cat #10829-018). Exemplary embryonic or fetal cells include, but are not limited to, embryonic stem cells, such as from already established lines, embryo carcinoma cells, murine embryonic fibroblasts, other embryo-like cells, cells of embryonic origin or cells derived from embryos, many of which are known in the art and available from the American Type Culture Collection, Manassas, Va. 20110-2209, USA, and other sources.

The embryonic or fetal cells may be added directly to the cultured blastomeres or may be grown in close proximity to, but not in direct contact with, the cultured blastomere(s). Various direct and indirect co-culture systems are possible to facilitate providing the cultured blastomeres with factors or signals from the embryonic or fetal cells. As used herein, "contacting the cultured cluster of two or more blastomeres" refers to any method of direct or indirect contact or co-culture.

In certain embodiments, contacting the cluster of two or more blastomere comprises aggregating blastomere clusters with embryonic or fetal cells. In certain other embodiments, contacting comprises co-culturing the cluster of two or mores blastomeres so that the cells are in direct contact with the embryonic or fetal cells but are not aggregated to them. In other embodiments, contacting comprises co-culturing the cluster of two or more blastomeres with the embryonic or fetal cells so that the cells are in indirect contact, for example, maintained in the same culture vessel but without direct contact of the cells or maintained as contiguous microdrops.

In certain embodiments, the method comprises the step of directly or indirectly contacting the cultured cluster of two or more blastomere(s) with embryonic or fetal cells, with the proviso that the contacting is not carried out by aggregating the cultured blastomere with embryonic cells as described in Chung et al., *Nature* (2006) 439:216-9. Alternatively, the culture of blastomere(s) and the culture of embryonic or fetal cells are indirectly connected or merged. This can be achieved by any method known in the art including, for example, dragging a manipulation pipette between two drops under light mineral oil such as Cooper Surgical ACT#ART4008, paraffin oil or Squibb's oil. The connections can be made by using a glass capillary or similar device. Such indirect connections between the cultured blastomere and the embryonic cells allows gradual mixing of the embryo medium (in which the blastomere is cultured) and the ES cell medium (in which the human embryonic cells are grown). In another embodiment, the blastomere(s) may be co-cultured with the remaining embryo. For example, the blastomere is co-cultured with the remaining embryo in a microdroplet culture system or other culture system known in the art, which does not permit cell-cell contact but could permit cell-secreted factor and/or cell-matrix contact. The volume of the microdrop may be reduced, e.g., from 50 microliters to about 5 microliters to intensify the signal. In another embodiment the embryonic cells may be from a species other than human, e.g., non-human primate or mouse.

In certain embodiments, the particular media formulations used to culture a blastomere, a cluster of two or more blastomeres, and embryonic or fetal cells may vary slightly depending on the species. Additionally, whether initial blastomere culture benefits from a media formulation different from that used to culture the clusters of blastomeres or the embryonic cells may also vary slightly depending on the species.

In certain embodiments, the medium used to separately culture a blastomere and the medium used to culture embryonic or fetal cells is not necessarily the same. In embodiments for which the media differ, there may be a period where the blastomere or cluster of blastomeres is being initially exposed to a medium that differs from the medium in which the blastomere was initially cultured (e.g., the cells will be slowly exposed to the medium in which the embryonic or fetal cells were cultured). In such embodiments, the cluster of two or more blastomeres, which has now divided multiple times to give rise to a cluster of cells and cell outgrowths, can gradually be transferred (for example by exchanging the medium) and cultured in medium having the properties of ES cell medium.

After about 3-4 days, the blastomere(s) exhibit properties of ES cells. Specifically, as the cells continue to divide and the blastomere progeny cluster, various cell types emerge and can be identified phenotypically. Amongst the emerging cell types are trophectoderm-like cells, ES cells, and partially or terminally differentiated ED cells. As such, these methods can be used to produce ES cells, TS or other trophectoderm cells, or ED cells. While not wishing to be bound by any particular theory, it is believed that over a period of days or weeks the cultured blastomeres exhibit ES cell growth perhaps as a result of factors secreted by the embryonic or fetal cells or by the extracellular matrix. Further, the dividing cluster of blastomere progeny resemble, in some respects, the changes observed during development of the preimplantation blastocyst. As such, the cell types emerging in these cultures recapitulate to some extent the cell types observed when whole blastocysts or ICMs are plated.

In certain embodiments, the blastomere culture conditions may include contacting the cells with factors that can inhibit or otherwise potentiate the differentiation of the cells, e.g., prevent the differentiation of the cells into non-ES cells, trophectoderm or other cell types. Such conditions can include contacting the cultured cells with heparin or introducing Oct-4 into the cells (such as by including Oct-4 in the media) or activating endogenous Oct-4 in the cells. In yet another embodiment, expression of cdx-2 is prevented by any means known in the art including, without limitation, introducing CDX-2 RNAi into blastomeres, thereby inhibiting differentiation of the blastomere into TS cells.

In certain embodiments, the blastomere culture medium is supplemented with factors to inhibit differentiation into non-ES cells. In certain embodiments, laminin is added to the culture medium in order to inhibit differentiation into non-ES cells. In certain embodiments, the medium is supplemented with about 2.5, 5, 7.5, 10, 15, or 20 µg/ml of laminin. In certain embodiments, the medium is supplemented with 1-5, 1-10, 5-10, 10-20 or 1-20 µg/ml of laminin.

In certain embodiments, the medium is supplemented with factors to disrupt tight junctions. In certain embodiments, laminin is added to the medium in order to disrupt tight junctions.

In certain embodiments, the medium is supplemented with factors to inhibit the trophectoderm differentiation pathway. In certain embodiments, laminin is added to the medium in order to inhibit the trophectoderm differentiation pathway.

In certain embodiments, the medium is supplemented with factors to depolarize cells. In certain embodiments, laminin is added to the medium in order to depolarize cells. In certain embodiments, depolarization is determined by a lack of microvilli on the cell surface. In certain embodiments, depolarization is determined by a piling of cells to form multilayered structures.

As detailed above, the invention provides methodologies for producing ES cells, ED cells, and TS cells from a blastomere obtained from an embryo. This approach can be used to generate ES cells, ED cell, and TS cells, as well as cell line without necessarily destroying the embryo from which the blastomere is obtained.

Culturing the Blastomere and Production of ED Cells

In the past, long-term culture of inner cell mass cells was used to produce embryonic stem cell lines. Subsequently, the embryonic stem cells were cultured and conditionally genetically-modified, and induced to differentiate in order to produce cells for therapy. U.S. patent application Ser. No. 11/025,893 (published as US 2005/0265976A1), incorporated herein in its entirety, describes a method of producing differentiated progenitor cells from inner cell mass cells or morula-derived cells by directly inducing the differentiation of those cells without producing an embryonic stem cell line and the use of said differentiated cells, tissues, and organs in transplantation therapy. Because these cells are derived from the cells of the embryo but not from an ES cell line, we designate such cells as embryo-derived (ED) cells. Blastomere-derived ED cells have broader differentiation potential than human ES cells produced using methods known in the art because the ED cells can be readily differentiated into germ-line cells using techniques known in the art, e.g. using methods to differentiate murine ES cell lines into germ-line cells. In contrast, human ES cell lines derived from inner mass cells are not expected to be capable of differentiation into germ-line cells. This phenomenon has been observed in ES cells derived from inner mass cells in animal such as pigs, cows, chickens and rats and is likely due to the fact that germ-line is one of the first cell lineages to branch out in differentiation.

In some of the methods of the present invention, blastomeres from embryos with at least two cells, and before the embryo enters the stage of development of a compacting morula are induced to directly differentiate into differentiated progenitor cells which are then used for cell therapy and for the generation of cells, tissues, and organs for transplantation. If desired, genetic modifications can be introduced, for example, into somatic cells prior to nuclear transfer to produce a morula or blastocyst or into somatic cells prior to the reprogramming of said somatic cell into undifferentiated cells through the juxtaposition of the DNA of said somatic cell with factors capable of reprogramming said somatic cells or into ES cell lines made using these methods. See U.S. patent application Ser. No. 10/831,599 published as US 2004199935, PCT/US06/30632 filed Aug. 3, 2006, and U.S. Provisional Patent Application Nos. 60/705,625, 60/729,173 and 60/818,813, the disclosure of which are incorporated herein by reference in their entirety. Thus, the differentiated progenitor cells of the present invention do not possess the pluripotency of an embryonic stem cell, or an embryonic germ cell, and are, in essence, tissue-specific partially or fully differentiated cells. These differentiated progenitor cells may give rise to cells from any of three embryonic germ layers, i.e., endoderm, mesoderm, and ectoderm. For example, the differentiated progenitor cells may differentiate into bone, cartilage, smooth muscle, dermis with a prenatal pattern of gene expression and capable of promoting scarless wound repair, and hematopoietic or hemangioblast cells (mesoderm), definitive endoderm, liver, primitive gut, pancreatic beta cells, and respiratory epithelium (endoderm); or neurons, glial cells, hair follicles, or eye cells including retinal neurons and retinal pigment epithelium.

Furthermore, it is not necessary for the differentiated progenitor cells of the present invention to express the catalytic component of telomerase (TERT) and be immortal, or that the progenitor cells express cell surface markers found on embryonic stem cells such as the cell surface markers characteristic of primate embryonic stem cells: positive for SSEA-3, SSEA-4, TRA-1-60, TRA-1-81, alkaline phosphatase activity, and negative for SSEA-1. Moreover, the differentiated progenitor cells of the present invention are distinct from embryoid bodies, i.e., embryoid bodies are derived from embryonic stem cells whereas the differentiated stem cells of the present invention are derived from blastomeres.

Preferably, the differentiated cells of the present invention are produced by culturing blastomere-derived cells in the absence of embryonic stem cells. Growth of undifferentiated embryonic stem cells can be prevented, for example, by culturing blastomeres in the presence of differentiation-inducing agents or by introducing genetic modifications into the cells such that the growth of embryonic stem cells is prevented.

Any vertebrate embryo may be used as a source of blastomeres or cells equivalent in development to a mammalian blastomere. Human blastomeres, in particular, have important utility in the generation of human cell-based therapies. The original embryo may have been produced by in vitro-fertilization, derived by fertilization within the reproductive tract by normal sexual reproduction, artificial insemination, or gamete intrafallopian transfer (GIFT), and subsequently retrieved, derived by somatic cell nuclear transfer.

Differentiation

Methods for isolating blastomeres have already been described herein. Isolated blastomeres can be induced directly or via ES cells or cell lines to differentiate in the presence of differentiation-inducing conditions including various combinations of growth factors, sera, hormones, extracellular matrices useful in making the particular desired differentiated cell type as known in the art (see Table 1 for list of exemplary molecules), or as disclosed in the pending applications PCT/US2006/013573 filed Apr. 11, 2006, U.S. Application No. 60/835,779, filed Aug. 3, 2006, 60/792,224 filed Apr. 14, 2006, 60/801,993 filed May 19, 2006, PCT/US2006/013519 filed Apr. 11, 2006, US application Ser. No. 11/025,893 (published as US 20050265976), WO2005/070011 published Aug. 4, 2005, and WO 2006/080952 published Aug. 3, 2006, the disclosure of which are incorporated herein by reference. For example, blastomeres or ES cells may be cultured on various inducer cell types such as those isolated as single cell-derived populations of cells, or on particular extracellular matrix components and other differentiation-inducing factors such as factors or combinations of factors shown in Table 1 below.

TABLE 1

| Culture Variables |
|---|
| EGF Ligands |
| 1) Amphiregulin |
| 2) Betacellulin |
| 3) EGF |
| 4) Epigen |
| 5) Epiregulin |
| 6) HB-EGF |

TABLE 1-continued

| Culture Variables |
|---|
| 7) Neuregulin-3 |
| 8) NRG1 isoform GGF2 |
| 9) NRG1 Isoform SMDF |
| 10) NRG1-alpha/HRG1-alpha |
| 11) TGF-alpha |
| 12) TMEFF1/Tomoregulin-1 |
| 13) TMEFF2 |
| 14) EGF Ligands pooled (1-13 above) |
| EGF R/ErbB Receptor Family |
| 15) EGF Receptor |
| 16) ErbB2 |
| 17) ErbB3 |
| 18) ErbB4 |
| 19) EGF/ErbB Receptors pooled (15-18 above) |
| FGF Ligands |
| 20) FGF acidic |
| 21) FGF basic |
| 22) FGF-3 |
| 23) FGF-4 |
| 24) FGF-5 |
| 25) FGF-6 |
| 26) KGF/FGF-7 |
| 27) FGF-8 |
| 28) FGF-9 |
| 29) FGF-10 |
| 30) FGF-11 |
| 31) FGF-12 |
| 32) FGF-13 |
| 33) FGF-14 |
| 34) FGF-15 |
| 35) FGF-16 |
| 36) FGF-17 |
| 37) FGF-18 |
| 38) FGF-19 |
| 39) FGF-20 |
| 40) FGF-21 |
| 41) FGF-22 |
| 42) FGF-23 |
| 43) FGF Ligands pooled (20-38 above) |
| FGF Receptors |
| 40) FGF R1 |
| 41) FGF R2 |
| 42) FGF R3 |
| 43) FGF R4 |
| 44) FGF R5 |
| 45) FGF Receptors pooled (40-44 above) |
| FGF Regulators |
| 46) FGF-BP |
| Hedgehogs |
| 47) Desert Hedgehog |
| 48) Sonic Hedgehog |
| 49) Indian Hedgehog |
| 50) Hedgehogs pooled (47-49 above) |
| Hedgehog Regulators |
| 51) Gas1 |
| 52) Hip |
| 53) Hedgehog Regulators pooled (51-52 above) |
| IGF Ligands |
| 54) IGF-I |
| 55) IGF-II |
| 56) IGF Ligands pooled (54-55 above) |
| IGF-I Receptor (CD221) |
| 57) IGF-I R |
| GF Binding Protein (IGFBP) Family |
| 58) ALS |
| 59 IGFBP-4 |
| 60) CTGF/CCN2 |
| 61) IGFBP-5 |
| 62) Endocan |

TABLE 1-continued

Culture Variables

63) IGFBP-6
64) IGFBP-1
65) IGFBP-rp1/IGFBP-7
66) IGFBP-2
67) NOV/CCN3
68) IGFBP-3
69) GF Binding Protein Family pooled (58-68 above)

Receptor Tyrosine Kinases

70) Axl
71) C1q R1/CD93
72) DDR1
73) Flt-3
74) DDR2
75) HGF R
76) Dtk
77) IGF-II R
78) Eph
79) Insulin R/CD220
80) EphA1
81) M-CSF R
82) EphA2
83) Mer
84) EphA3
85) MSP R/Ron
86) EphA4
87) MuSK
88) EphA5
89) PDGF R alpha
90) EphA6
91) PDGF R beta
92) EphA7
93) Ret
94) EphA8
95) ROR1
96) EphB1
97) ROR2
98) EphB2
99) SCF R/c-kit
100) EphB3
101) Tie-1
102) EphB4
103) Tie-2
104) EphB6
105) TrkA
106) TrkB
107) TrkC
108) VEGF R1/Flt-1
109) VEGF R2/Flk-1
110) VEGF R3/Flt-4
111) Receptor Tyrosine Kinases pooled (70-110 above)

Proteoglycans

112) Aggrecan
113) Lumican
114) Biglycan
115) Mimecan
116) Decorin
117) NG2/MCSP
118) Endocan
119) Osteoadherin
120) Endorepellin
121) Syndecan-1/CD138
122) Glypican 2
123) Syndecan-3
124) Glypican 3
125) Testican 1/SPOCK1
126) Glypican 5
127) Testican 2/SPOCK2
128) Glypican 6
129) Testican 3/SPOCK3
130) Heparan sulfate proteoglycan
131) Heparin
132) Chondroitin sulfate proteoglycan
133) Hyaluronic acid
134) Dermatan sulfate proteoglycan TABLE 1-continued Culture Variables Proteoglycan Regulators 135) Arylsulfatase A/ARSA
136) HAPLN1
137) Exostosin-like 2
138) HS6ST2
139) Exostosin-like 3
140) IDS
141) Proteoglycan Regulators pooled (135-140 above)

SCF, Flt-3 Ligand & M-CSF

142) Flt-3
143) M-CSF R
144) Flt-3 Ligand
145) SCF
146) M-CSF
147) SCF R/c-kit
148) Pooled factors (142-147 above)

Activins

149) Activin A
150) Activin B
151) Activin AB
152) Activin C
153) Pooled Activins (149-152 above)

BMPs (Bone Morphogenetic Proteins)

154) BMP-2
155) BMP-3
156) BMP-3b/GDF-10
157) BMP-4
158) BMP-5
159) BMP-6
160) BMP-7
161) BMP-8
162) Decapentaplegic
163) Pooled BMPs (154-162 above)

GDFs (Growth Differentiation Factors)

164) GDF-1
165) GDF-2
166) GDF-3
167) GDF-4
168) GDF-5
169) GDF-6
170) GDF-7
171) GDF-8
172) GDF-9
173) GDF-10
174) GDF-11
175) GDF-12
176) GDF-13
177) GDF-14
178) GDF-15
179) GDFs pooled (164-178 above)

GDNF Family Ligands

180) Artemin
181) Neurturin
182) GDNF
183) Persephin
184) GDNF Ligands pooled (180-183 above)

TGF-beta

185) TGF-beta
186) TGF-beta 1
187) TGF-beta 1.2
188) TGF-beta 2
189) TGF-beta 3
190) TGF-beta 4
191) TGF-beta 5
192) LAP (TGF-beta 1)
193) Latent TGF-beta 1
194) TGF-beta pooled (185-193 above)

Other TGF-beta Superfamily Ligands

195) Lefty
196) Nodal

TABLE 1-continued

Culture Variables

197) MIS/AMH
198) Other TGF-beta Ligands pooled (195-197 above)

TGF-beta Superfamily Receptors

199) Activin RIA/ALK-2
200) GFR alpha-1
201) Activin RIB/ALK-4
202) GFR alpha-2
203) Activin RIIA
204) GFR alpha-3
205) Activin RIIB
206) GFR alpha-4
207) ALK-1
208) MIS RII
209) ALK-7
210) Ret
211) BMPR-IA/ALK-3
212) TGF-beta RI/ALK-5
213) BMPR-IB/ALK-6
214) TGF-beta RII
215) BMPR-II
216) TGF-beta RIIb
217) Endoglin/CD105
218) TGF-beta RIII
219) TGF-beta family receptors pooled (199-218 above)

TGF-beta Superfamily Modulators

220) Amnionless
221) GASP-2/WFIKKN
222) BAMBI/NMA
223) Gremlin
224) Caronte
225) NCAM-1/CD56
226) Cerberus 1
227) Noggin
228) Chordin
229) PRDC
230) Chordin-Like 1
231) Chordin-Like 2
232) Smad1
233) Smad4
234) Smad5
235) Smad7
236) Smad8
237) CRIM1
238) Cripto
239) Crossveinless-2
240) Cryptic
241) SOST
242) DAN
243) Latent TGF-beta bp1
244) TMEFF1/Tomoregulin-1
245) FLRG
246) TMEFF2
247) Follistatin
248) TSG
249) Follistatin-like 1
250) Vasorin
251) GASP-1/WFIKKNRP
252) TGF Modulators pooled (220-251 above)

VEGF/PDGF Family

253) Neuropilin-1
254) PlGF
255) PlGF-2
256) Neuropilin-2
257) PDGF
258) VEGF R1/Flt-1
259) PDGF R alpha
260) VEGF R2/Flk-1
261) PDGF R beta
262) VEGF R3/Flt-4
263) PDGF-A
264) VEGF
265) PDGF-B
266) VEGF-B
267) PDGF-C
268) VEGF-C TABLE 1-continued Culture Variables 269) PDGF-D
270) VEGF-D
271) PDGF-AB
272) VEGF/PDGF Family pooled (253-271 above)

Dickkopf Proteins & Wnt Inhibitors

273) Dkk-1
274) Dkk-2
275) Dkk-3
276) Dkk-4
277) Soggy-1
278) WIF-1
279) Pooled factors (273-278 above)

Frizzled & Related Proteins

280) Frizzled-1
281) Frizzled-2
282) Frizzled-3
283) Frizzled-4
284) Frizzled-5
285) Frizzled-6
286) Frizzled-7
287) Frizzled-8
288) Frizzled-9
289) sFRP-1
290) sFRP-2
291) sFRP-3
292) sFRP-4
293) MFRP
294) Factors pooled (280-293 above)

Wnt Ligands

295) Wnt-1
296) Wnt-2
297) Wnt-3
298) Wnt-3a
299) Wnt-4
300) Wnt-5
301) Wnt-5a
302) Wnt-6
303) Wnt-7
304) Wnt-8
305) Wnt-8a
306) Wnt-9
307) Wnt-10a
308) Wnt-10b
309) Wnt-11
310 Wnt Ligands pooled (295-309 above)

Other Wnt-related Molecules 311) beta-Catenin
312) LRP-6
313) GSK-3
314) ROR1
315) Kremen-1
316) ROR2
317) Kremen-2
318) WISP-1/CCN4
319) LRP-1
320) Pooled factors (311-319 above)

Other Growth Factors

321) CTGF/CCN2
322) NOV/CCN3
323) EG-VEGF/PK1
324) Osteocrin
325) Hepassocin
326) PD-ECGF
327) HGF
328) Progranulin
329) beta-NGF
330) Thrombopoietin
331) Pooled factors (321-330 above)

Steroid Hormones 332) 17beta-Estradiol
333) Testosterone

TABLE 1-continued

Culture Variables

334) Cortisone
335) Dexamethasone

Extracellular/Membrane Proteins

336) Plasma Fibronectin
337) Tissue Fibronectin
338) Fibronectin fragments
339) Collagen Type I (gelatin)
340) Collagen Type II
341) Collagen Type III
342) Tenascin
343) Matrix Metalloproteinase 1
344) Matrix Metalloproteinase 2
345) Matrix Metalloproteinase 3
346) Matrix Metalloproteinase 4
347) Matrix Metalloproteinase 5
348) Matrix Metalloproteinase 6
349) Matrix Metalloproteinase 7
350) Matrix Metalloproteinase 8
351) Matrix Metalloproteinase 9
352) Matrix Metalloproteinase 10
353) Matrix Metalloproteinase 11
354) Matrix Metalloproteinase 12
355) Matrix Metalloproteinase 13
356) ADAM-1
357) ADAM-2
358) ADAM-3
359) ADAM-4
360) ADAM-5
361) ADAM-6
362) ADAM-7
363) ADAM-8
364) ADAM-9
365) ADAM-10
366) ADAM-11
367) ADAM-12
368) ADAM-13
369) ADAM-14
370) ADAM-15
371) ADAM-16
372) ADAM-17
373) ADAM-18
374) ADAM-19
375) ADAM-20
376) ADAM-21
377) ADAM-22
378) ADAM-23
379) ADAM-24
380) ADAM-25
381) ADAM-26
382) ADAM-27
383) ADAM-28
384) ADAM-29
385) ADAM-30
386) ADAM-31
387) ADAM-32
388) ADAM-33
389) ADAMTS-1
390) ADAMTS-2
391) ADAMTS-3
392) ADAMTS-4
393) ADAMTS-5
394) ADAMTS-6
395) ADAMTS-7
396) ADAMTS-8
397) ADAMTS-9
398) ADAMTS-10
399) ADAMTS-11
400) ADAMTS-12
401) ADAMTS-13
402) ADAMTS-14
403) ADAMTS-15
404) ADAMTS-16
405) ADAMTS-17
406) ADAMTS-18
407) ADAMTS-19
408) ADAMTS-20
409) Arg-Gly-Asp
410) Arg-Gly-Asp-Ser
411) Arg-Gly-Asp-Ser-Pro-Ala-Ser-Ser-Lys-Pro
412) Arg-Gly-Glu-Ser
413) Arg-Phe-Asp-Ser
414) SPARC
415) Cys-Asp-Pro-Gly-Tyr-Ile-Gly-Ser-Arg
416) Cys-Ser-Arg-Ala-Arg-Lys-Gln-Ala-Ala-Ser-Ile-Lys-Val-Ser-Ala-Asp-Arg
417) Elastin
418) Tropelastin
419) Gly-Arg-Gly-Asp-Ser-Pro-Lys
420) Gly-Arg-Gly-Asp-Thr-Pro
421) Laminin
422) Leu-Gly-Thr-Ile-Pro-Gly
423) Ser-Asp-Gly-Arg-Gly
424) Vitronectin
425) Superfibronectin
426) Thrombospondin
427) TIMP-1
428) TIMP-2
429) TIMP-3
430) TIMP-4
431) Fibromodulin
432) Flavoridin
433) Collagen IV
434) Collagen V
435) Collagen VI
436) Collagen VII
437) Collagen VIII
438) Collagen IX
439) Collagen X
440) Collagen XI
441) Collagen XII
442) Entactin
443) Fibrillin
444) Syndecan-1
445) Keratan sulfate proteoglycan

Ambient Oxygen 446) 0.1-0.5% Oxygen
447) 0.5-1% Oxygen
448) 1-2% Oxygen
449) 2-5% Oxygen
450) 5-10% Oxygen
451) 10-20% Oxygen

Animal Serum 452) 0.1% Bovine Serum
453) 0.5% Bovine Serum
454) 1.0% Bovine Serum
455) 5.0% Bovine Serum
456) 10% Bovine Serum
457) 20% Bovine Serum
458) 10% Horse Serum

Interleukins

459) IL-1
460) IL-2
461) IL-3
462) IL-4
463) IL-5
464) IL-6
465) IL-7
466) IL-8
467) IL-9
468) IL-10
469) IL-11
470) IL-12
471) IL-13
472) IL-14
473) IL-15
474) IL-16
475) IL-17
476) IL-18

Proteases

477) MMP-1
478) MMP-2

TABLE 1-continued

Culture Variables

479) MMP-3
480) MMP-4
481) MMP-5
482) MMP-6
483) MMP-7
484) MMP-8
485) MMP-9
486) MMP-10
487) MMP-11
488) MMP-12
489) MMP-13
490) MMP-14
491) MMP-15
492) MMP-16
493) MMP-17
494) MMP-18
495) MMP-19
496) MMP-20
497) MMP-21
498) MMP-22
499) MMP-23
500) MMP-24
501) Cathepsin B
501) Cathepsin C
503) Cathepsin D
504) Cathepsin G
505) Cathepsin H
506) Cathepsin L
507) Trypsin
508) Pepsin
509) Elastase
510) Carboxypeptidase A
511) Carboxypeptidase B
512) Carboxypeptidase G
513) Carboxypeptidase P
514) Carboxypeptidase W
515) Carboxypeptidase Y
516) Chymotrypsin
517) Plasminogen
518) Plasmin
519) u-type Plasminogen activator
520) t-type Plasminogen activator
521) Plasminogen activator inhibitor-1
522) Carboxypeptidase Z

Amino Acids

522) Alanine
523) Arginine
524) Asparagine
525) Aspartic acid
526) Cysteine
527) Glutamine
528) Glutamic acid
529) Glycine
530) Histidine
531) Isoleucine
532) Leucine
533) Lysine
534) Methionine
535) Phenylalanine
536) Proline
537) Serine
538) Threonine
539) Tryptophan
540) Tyrosine
541) Valine

Prostaglandins

542) Prostaglandin A1
543) Prostaglandin A2
544) Prostaglandin B1
545) Prostaglandin B2
546) Prostaglandin D2
547) Prostaglandin E1
548) Prostaglandin E2
549) Prostaglandin F1alpha
550) Prostaglandin F2alpha
551) Prostaglandin H
552) Prostaglandin I2
553) Prostaglandin J2
554) 6-Keto-Prostaglandin F1a
555) 16,16-Dimethyl-Prostaglandin E2
556) 15d-Prostaglandin J2
557) Prostaglandins pooled (542-556 above)

Retinoid receptor agonists/Antagonists

558) Methoprene Acid
559) All trans retinoic acid
560) 9-Cis Retinoic Acid
561) 13-Cis Retinoic Acid
562) Retinoid agonsts pooled (558-561 above)
563) Retinoid antagonists
564) Retinoic acid receptor isotype RARalpha
565) Retinoic acid receptor isotype RARbeta
566) Retinoic acid receptor isotype RARgamma
567) Retinoic X receptor isotype RXRalpha
568) Retinoic X receptor isotype RXRbeta
569) Retinoic X receptor isotype RARgamma

Miscellaneous Inducers

570) Plant lectins
571) Bacterial lectins
572) forskolin
573) Phorbol myristate acetate
574) Poly-D-lysine
575) 1,25-dihydroxyvitamin D
576) Inhibin
577) Heregulin
578) Glycogen
579) Progesterone
580) IL-1
581) Serotonin
582) Fibronectin - 45 kDa Fragment
583) Fibronectin - 70 kDa Fragment
584) glucose
585) beta mercaptoethanol
586) heparinase
587) pituitary extract
588) chorionic gonadotropin
589) adrenocorticotropic hormone
590) thyroxin
591) Bombesin
592) Neuromedin B
593) Gastrin-Releasing Peptide
594) Epinephrine
595) Isoproterenol
596) Ethanol
597) DHEA
598) Nicotinic Acid
599) NADH
600) Oxytocin
601) Vasopressin
602) Vasotocin
603) Angiotensin I
604) Angiotensin II
605) Angiotensin I Converting Enzyme
606) Angiotensin I Converting Enzyme Inhibitor
607) Chondroitinase AB
608) Chondroitinase C
609) Brain natriuretic peptide
610) Calcitonin
611) Calcium ionophore I
612) Calcium ionophore II
613) Calcium ionophore III
614) Calcium ionophore IV
615) Bradykinin
616) Albumin
617) Plasmonate
618) LIF
619) PARP inhibitors
620) Lysophosphatidic acid
621) (R)-METHANANDAMIDE
622) 1,25-DIHYDROXYVITAMIN D3
623) 1,2-DIDECANOYL-GLYCEROL (10:0)
624) 1,2-DIOCTANOYL-SN-GLYCEROL
625) 1,2-DIOLEOYL-GLYCEROL (18:1)

TABLE 1-continued

Culture Variables 626) 10-hydroxycamptothecin
627) 11,12-EPOXYEICOSATRIENOIC ACID
628) 12(R)-HETE
629) 12(S)-HETE
630) 12(S)-HPETE
631) 12-METHOXYDODECANOIC ACID
632) 13(S)-HODE
633) 13(S)-HPODE
634) 13,14-DIHYDRO-PGE1
635) 13-KETOOCTADECADIENOIC ACID
636) 14,15-EPOXYEICOSATRIENOIC ACID
637) 1400W
638) 15(S)-HETE
639) 15(S)-HPETE
640) 15-KETOEICOSATETRAENOIC ACID
641) 17-Allylamino-geldanamycin
642) 17-OCTADECYNOIC ACID
643) 17-PHENYL-TRINOR-PGE2
644) 1-ACYL-PAF
645) 1-HEXADECYL-2-ARACHIDONOYL-522) 646) GLYCEROL
647) 1-HEXADECYL-2-METHYLGLYCERO-3 PC
648) 1-HEXADECYL-2-O-ACETYL-GLYCEROL
649) 1-HEXADECYL-2-O-METHYL-GLYCEROL
650) 1-OCTADECYL-2-METHYLGLYCERO-3 PC
651) 1-OLEOYL-2-ACETYL-GLYCEROL
652) 1-STEAROYL-2-LINOLEOYL-GLYCEROL
653) 1-STEAROYL-2-ARACHIDONOYL-GLYCEROL
654) 2,5-ditertbutylhydroquinone
655) 24(S)-hydroxycholesterol
656) 24,25-DIHYDROXYVITAMIN D3
657) 25-HYDROXYVITAMIN D3
658) 2-ARACHIDONOYLGLYCEROL
659) 2-FLUOROPALMITIC ACID
660) 2-HYDROXYMYRISTIC ACID
661) 2-methoxyantimycin A3
662) 3,4-dichloroisocoumarin
663) granzyme B inhibitor
664) 4-AMINOPYRIDINE
665) 4-HYDROXYPHENYLRETINAMIDE
666) 4-OXATETRADECANOIC ACID
667) 5(S)-HETE
668) 5(S)-HPETE
669) 5,6-EPOXYEICOSATRIENOIC ACID
670) 5,8,11,14-EICOSATETRAYNOIC ACID
671) 5,8,11-EICOSATRIYNOIC ACID
672) 5-HYDROXYDECANOATE
673) 5-iodotubercidin
674) 5-KETOEICOSATETRAENOIC ACID
675) 5'-N-Ethylcarboxamidoadenosine (NECA)
676) 6,7-ADTN HBr
677) 6-FORMYLINDOLO [3,2-B] CARBAZOLE
678) 7,7-DIMETHYLEICOSADIENOIC ACID
679) 8,9-EPOXYEICOSATRIENOIC ACID
680) 8-methoxymethyl-IBMX
681) 9(S)-HODE
682) 9(S)-HPODE
683) 9,10-OCTADECENOAMIDE
684) A-3
685) AA-861
686) acetyl (N)-s-farnesyl-1-cysteine
687) ACETYL-FARNESYL-CYSTEINE
688) Ac-Leu-Leu-Nle-CHO
689) ACONITINE
690) actinomycin D
691) ADRENIC ACID (22:4, n-6)
692) 1 mM
693) AG-1296
694) AG1478
695) AG213 (Tyrphostin 47)
696) AG-370
697) AG-490
698) AG-879
699) AGC
700) AGGC
701) Ala-Ala-Phe-CMK
702) alamethicin
703) Alrestatin
704) AM 92016
704) AM-251
706) AM-580
707) AMANTIDINE
708) AMILORIDE
709) Amino-1,8-naphthalimide [4-Amino-1,8-522) naphthalimide]
710) Aminobenzamide (3-ABA) [3-522) aminobenzamide (3-ABA)]
711) AMIODARONE
712) ANANDAMIDE (18:2, n-6)
713) ANANDAMIDE (20:3, n-6)
714) ANANDAMIDE (20:4, n-6)
715) ANANDAMIDE (22:4, n-6)
716) anisomycin
717) aphidicolin
718) ARACHIDONAMIDE
719) ARACHIDONIC ACID (20:4, n-6)
720) ARACHIDONOYL-PAF
721) aristolochic acid
722) Arvanil
723) ascomycin (FK-520)
724) B581
725) BADGE
726) bafilomycin A1
727) BAPTA-AM
728) BAY 11-7082
729) BAY K-8644
730) BENZAMIL
731) BEPRIDIL
732) Bestatin
733) beta-lapachone
734) Betulinic acid
735) bezafibrate
736) Blebbistatin
737) BML-190
738) Boc-GVV-CHO
739) bongkrekic acid
740) brefeldin A
741) Bromo-7-nitroindazole [3-Bromo-7-nitroindazole]
742) Bromo-cAMP [8-Bromo-cAMP]
743) Bromo-cGMP [8-Bromo-cGMP]
744) bumetanide
745) BW-B 70C
746) C16 CERAMIDE
747) C2 CERAMIDE
748) C2 DIHYDROCERAMIDE
749) C8 CERAMIDE
750) C8 CERAMINE
750) C8 DIHYDROCERAMIDE
751) CA-074-Me
753) calpeptin
754) calphostin C
755) calyculin A
756) camptothecin
757) cantharidin
758) CAPE
759) capsacin(E)
760) capsazepine
761) CARBACYCLIN
762) castanospermine
763) CDC
764) Cerulenin
765) CGP-37157
766) chelerythrine
767) CIGLITAZONE
768) CIMATEROL
769) CinnGEL 2Me
770) CIRAZOLINE
771) CITCO
772) CLOFIBRATE
773) clonidine
774) CLOPROSTENOL Na
775) clozapine
776) C-PAF
777) Curcumin
778) Cyclo [Arg-Gly-Asp-D-Phe-Val]
779) cycloheximide
780) protein synthesis inhibitor
781) cycloheximide-N-ethylethanoate
782) cyclopamine

TABLE 1-continued

Culture Variables

783) CYCLOPIAZONIC ACID
784) cyclosporin A
785) cypermethrin
786) cytochalasin B
787) cytochalasin D
788) D12-PROSTAGLANDIN J2
789) D609
790) damnacanthal
791) DANTROLENE
792) decoyinine
793) Decylubiquinone
794) deoxymannojirimycin(1)
795) deoxynorjrimycin(1)
796) Deprenyl
797) DIAZOXIDE
798) dibutyrylcyclic AMP
799) dibutyrylcyclic GMP
800) DICHLOROBENZAMIL
801) DIHOMO-GAMMA-LINOLENIC ACID
802) DIHYDROSPHINGOSINE
803) DIINDOLYLMETHANE
804) DILTIAZEM
805) diphenyleneiodonium Cl
806) dipyridamole
807) DL-DIHYDROSPHINGOSINE
808) DL-PDMP
809) DL-PPMP
810) DOCOSAHEXAENOIC ACID (22:6 n-3)
811) DOCOSAPENTAENOIC ACID
812) DOCOSATRIENOIC ACID (22:3 n-3)
813) doxorubicin
814) DRB
815) E-4031
816) E6 berbamine
817) E-64-d
818) Ebselen
819) EHNA HCl
820) EICOSA-5,8-DIENOIC ACID (20:2 n-12)
821) EICOSADIENOIC ACID (20:2 n-6)
822) EICOSAPENTAENOIC ACID (20:5 n-3)
823) EICOSATRIENOIC ACID (20:3 n-3)
824) ENANTIO-PAF C16
825) epibatidine (+/−)
826) etoposide
827) FARNESYLTHIOACETIC ACID
828) FCCP
829) FIPRONIL
830) FK-506
831) FLECAINIDE
832) FLUFENAMIC ACID
833) FLUNARIZINE
834) FLUPROSTENOL
835) FLUSPIRILINE
836) FPL-64176
837) Fumonisin B1
838) Furoxan
839) GAMMA-LINOLENIC ACID (18:3 n-6)
840) geldanamycin
841) genistein
842) GF-109203X
843) GINGEROL
844) Gliotoxin
845) GLIPIZIDE
846) GLYBURIDE
847) GM6001
848) Go6976
849) GRAYANOTOXIN III
850) GW-5074
851) GW-9662
852) H7]
853) H-89
854) H9
855) HA-1004
856) HA1077
857) HA14-1
858) HBDDE
859) Helenalin
860) Hinokitiol
861) HISTAMINE
862) HNMPA-(AM)3
863) Hoechst 33342 (cell permeable) (BisBenzimide)
864) Huperzine A [(−)-Huperzine A]
865) IAA-94
866) IB-MECA
867) IBMX
868) ICRF-193
869) Ikarugamyin
870) Indirubin
871) Indirubin-3'-monoxime
872) indomethacin
873) juglone
874) K252A
875) Kavain (+/−)
876) KN-62
877) KT-5720
878) L-744,832
879) Latrunculin B
880) Lavendustin A
881) L-cis-DILTIAZEM
882) LEUKOTOXIN A (9,10-EODE)
883) LEUKOTOXIN B (12,13-EODE)
884) LEUKOTRIENE B4
885) LEUKOTRIENE C4
886) LEUKOTRIENE D4
887) LEUKOTRIENE E4
888) Leupeptin
889) LFM-A13
890) LIDOCAINE
891) LINOLEAMIDE
892) LINOLEIC ACID
893) LINOLENIC ACID (18:3 n-3)
894) LIPOXIN A4
895) L-NAME
896) L-NASPA
897) LOPERAMIDE
898) LY-171883
899) LY-294002
900) LY-83583
901) Lycorine
902) LYSO-PAF C16
903) Manoalide
904) manumycin A
905) MAPP, D-erythro
906) MAPP, L-erythro
907) mastoparan
908) MBCQ
909) MCI-186
910) MDL-28170
911) MEAD ACID (20:3 n-9)
912) MEAD ETHANOLAMIDE
913) methotrexate
914) METHOXY VERAPAMIL
915) Mevinolin (lovastatin)
916) MG-132
917) Milrinone
918) MINOXIDIL
919) MINOXIDIL SULFATE
920) MISOPROSTOL, FREE ACID
921) mitomycin C
922) ML7
923) ML9
924) MnTBAP
925) Monastrol
926) monensin
927) MY-5445
928) Mycophenolic acid
929) N,N-DIMETHYLSPHINGOSINE
930) N9-Isopropylolomoucine
931) N-ACETYL-LEUKOTRIENE E4
932) NapSul-Ile-Trp-CHO
933) N-ARACHIDONOYLGLYCINE
934) NICARDIPINE
935) NIFEDIPINE
936) NIFLUMIC ACID
937) Nigericin
938) NIGULDIPINE TABLE 1-continued Culture Variables 939) Nimesulide
940) NIMODIPINE
941) NITRENDIPINE
942) N-LINOLEOYLGLYCINE
943) nocodazole
944) N-PHENYLANTHRANILIC (CL)
945) NPPB
946) NS-1619
947) NS-398
948) NSC-95397
949) OBAA
950) okadaic acid
951) oligomycin A
952) olomoucine
953) ouabain
954) PAF C16
955) PAF C18
956) PAF C18:1
957) PALMITYLETHANOLAMIDE
958) Parthenolide
959) PAXILLINE
960) PCA 4248
961) PCO-400
962) PD 98059
963) PENITREM A
964) pepstatin
965) PHENAMIL
966) Phenanthridinone [6(5H)-Phenanthridinone]
967) Phenoxybenzamine
968) PHENTOLAMINE
969) PHENYTOIN
970) PHOSPHATIDIC ACID, DIPALMITOYL
971) Piceatannol
972) pifithrin
973) PIMOZIDE
974) PINACIDIL
975) piroxicam
976) PP1
977) PP2
978) prazocin
979) Pregnenolone 16alpha carbonitrile
980) PRIMA-1
981) PROCAINAMIDE
982) PROPAFENONE
983) propidium iodide
984) propranolol (S—)
985) puromycin
986) quercetin
987) QUINIDINE
988) QUININE
989) QX-314
990) rapamycin
991) resveratrol
992) RETINOIC ACID, ALL TRANS
993) REV-5901
994) RG-14620
995) RHC-80267
996) RK-682
997) Ro 20-1724
998) Ro 31-8220
999) Rolipram
1000) roscovitine
1001) Rottlerin
1002) RWJ-60475-(AM)3
1003) RYANODINE
1004) SB 202190
1005) SB 203580
1006) SB-415286
1007) SB-431542
1008) SDZ-201106
1009) S-FARNESYL-L-CYSTEINE ME
1010) Shikonin
1011) siguazodan
1012) SKF-96365
1013) SP-600125
1014) SPHINGOSINE
1015) Splitomycin
1016) SQ22536
1017) SQ-29548
1018) staurosporine
1019) SU-4312
1020) Suramin
1021) swainsonine
1022) tamoxifen
1023) Tanshinone IIA
1024) taxol = paclitaxel
1025) TETRAHYDROCANNABINOL-7-OIC ACID
1026) TETRANDRINE
1027) thalidomide
1028) THAPSIGARGIN
1029) Thiocitrulline [L-Thiocitrulline HCl]
1030) Thiorphan
1031) TMB-8
1032) TOLAZAMIDE
1033) TOLBUTAMIDE
1034) Tosyl-Phe-CMK (TPCK)
1035) TPEN
1036) Trequinsin
1037) trichostatin-A
1038) trifluoperazine
1039) TRIM
1040) Triptolide
1041) TTNPB
1042) Tunicamycin
1043) tyrphostin 1
1044) tyrphostin 9
1045) tyrphostin AG-126
1046) tyrphostin AG-370
1047) tyrphostin AG-825
1048) Tyrphostin-8
1049) U-0126
1050) U-37883A
1051) U-46619
1052) U-50488
1053) U73122
1054) U-74389G
1055) U-75302
1056) valinomycin
1057) Valproic acid
1058) VERAPAMIL
1059) VERATRIDINE
1060) vinblastine
1061) vinpocetine
1062) W7
1063) WIN 55,212-2
1064) Wiskostatin
1065) Wortmannin
1066) WY-14643
1067) Xestospongin C
1068) Y-27632
1069) YC-1
1070) Yohimbine
1071) Zaprinast
1072) Zardaverine
1073) ZL3VS
1074) ZM226600
1075) ZM336372
1076) Z-prolyl-prolinal
1077) zVAD-FMK
1078) Ascorbate
1079) 5-azacytidine
1080) 5-azadeoxycytidine
1081) Hexamethylene bisacetamide (HMBA)
1082) Sodium butyrate
1083) Dimethyl sulfoxide.
1084) Goosecoid
1085) Glycogen synthase kinase-3
1086) Galectin-1
1087) Galectin-3

Cell Adhesion Molecules

1086) Cadherin 1 (E-Cadherin)
1087) Cadherin 2 (N-Cadherin)
1088) Cadherin 3 (P-Cadherin)
1089) Cadherin 4 (R-Cadherin)
1090) Cadherin 5 (VE-Cadherin)

TABLE 1-continued

Culture Variables

1091) Cadherin 6 (K-Cadherin)
1092) Cadherin 7
1093) Cadherin 8
1094) Cadherin 9
1095) Cadherin 10
1096) Cadherin 11 (OB-Cadherin)
1097) Cadherin 12 (BR-Cadherin)
1098) Cadherin 13 (H-Cadherin)
1099) Cadherin 14 (same as Cadherin 18)
1100) Cadherin 15 (M-Cadherin)
1101) Cadherin 16 (KSP-Cadherin)
1102) LI Cadherin The foregoing is exemplary of the factors and conditions that can be used to promote differentiation of ES cells or ED cells along particular developmental lineages. Partially or terminally differentiated endodermal, mesodermal, or ectodermal cell types can be used in screening assays, to study developmental and stem cell biology, or to produce therapeutics. Partially or terminally differentiated cell types can optionally be substantially purified, formulated as pharmaceutical preparations, and/or cryopreserved.

Pluripotency of ES Cells

Pluripotency of the human ES cells or cell lines produced by any of the methods of this invention can be determined by detecting expression of human ES cell marker proteins. Examples of such proteins include but are not limited to octamer binding protein 4 (Oct-4), stage-specific embryonic antigen (SSEA)-3, SSEA-4, TRA-1-60, TRA-1-81 and alkaline phosphatase. In some embodiments, the putative ES cell lines maintain pluripotency after more than 13, 20, 30, 40, 50, 60, 70, 80, 90 or 100 passages. The ES cells may also be assayed for maintenance of normal karyotype. Pluripotency may also be confirmed by differentiating the ES cell produced by the methods of this invention into cells of ectoderm, endoderm and mesoderm lineage using methods known in the art. Pluripotency may also be tested by transplanting ES cells in vivo, for example into an immunodeficient mouse (such as a SCID mouse), and evaluating teratoma formation.

In certain embodiments, the ES cells or cell lines produced from a blastomere express one or more ES cell marker protein. Additionally or alternatively, in certain embodiments, the cells maintain a normal karyotype. Additionally or alternatively, in certain embodiments, the cells maintain pluripotency after more than 13, 20, 30, 40, 50, 60, 70, 80, 90 or 100 passages.

For any of the foregoing, the ES cell or cell line produced from a blastomere can be generated without destroying the embryo from which the blastomere used to generate the cell or line is obtained. This characteristic of the cells distinguishes these cells from currently available ES cells and lines which were generated using methods that necessarily destroyed the underlying embryo.

Production of TS Cells

This invention also provides methods of directly differentiating cell types from isolated blastomeres before and without generating ES cell lines. In one example, human trophoblast stem ("TS") cells are produced by contacting blastomere outgrowths, which morphologically resemble trophoblast and/or extraembryonic endoderm, but which do not resemble ES cells, with FGF-4. For example, FGF-4 is added to the culture media of the outgrowths. TS cells can be detected by assaying expression of proteins such as cdx-2, fgfr2, PL-1 and human chorionic gonadotropin (hCG) using procedures standard in the art. TS cell identification can also be evidenced by absence of the expression of proteins such as, but not limited to, Oct-4 and α-feto protein.

Production of Purified Preparations and Cell Lines

In certain embodiments, cell lines can be produced. By way of example, once a particular cell type is identified in a culture comprising a cluster of two or more blastomeres (blastomere-derived outgrowths), that cell can be separated from the remainder of the culture for further use. Once separated, the desired cell can be propagated as a purified or substantially purified population, or it can be maintained as a cell line.

In certain embodiments, an ES cell produced from culturing a blastomere obtained from an embryo is separated from the culture of blastomere-derived outgrowths, and an ES cell line is established using standard techniques developed when establishing ES cell lines from blastocyst stage embryos. In other embodiments, a partially differentiated ED cell of interest can be select based on, for example, morphology and that cell can be separated from the culture and purified or otherwise further analyzed.

Exemplary cell lines include stable cell lines. ES cell lines established in this way may have the properties of existing ES cell lines, for example, differentiation potential, protein expression, karyotype, and the like. Alternatively, ES cell lines established in this way may differ from existing ES cell lines in one or more ways.

Therapeutic Uses of ES and ED Cells

The ES or ED cells of this invention are suitable for any use for which ES cells are useful. The present invention provides a method of treating a disorder amenable to cell therapy comprising administering to the affected subject a therapeutically effective amount of the ES cells of the invention.

In one embodiment the methods of the invention are used to remove a blastomere preceding implantation of a human embryo after which the blastomere would be cultured as described above in order to derive and store human ES cells for therapeutic uses using cell therapy should the child resulting from the human embryo require, for example, disease therapy, tissue repair, transplantation, treatment of a cellular debilitation, or treatment of cellular dysfunctions in the future.

In another embodiment of the invention, cells derived from a blastomere, precompaction morula, compacting morula, or sectioned blastocyst are directly differentiated in vitro or in vivo to generate differentiating or differentiated cells without generating an embryonic stem cell line. See U.S. patent publication no. 20050265976, published Dec. 1, 2005, and international patent publication no. WO0129206, published Apr. 26, 2001, the disclosures of which are hereby incorporated by reference herein for methods of direct differentiation. The cells of the invention are useful in medical, veterinary and biological research and in the treatment of disease by providing cells for use in cell therapy, e.g., allogeneic cell therapy.

In another embodiment, an ES cell or cell line is derived from a blastomere and the ES cell or cell line is induced to differentiate to produce one or more mesodermal, endodermal, or ectodermal cell types. Exemplary cell types include, but are not limited to, RPE cells, hematopoietic stem cells, hematopoietic cell types (e.g., RBCs, platelets, etc.), pancreatic beta cells, skin cells, cardiomyocytes, smooth muscle cells, endothelial cells, hepatocytes, neurons, glia, skeletal muscle cells, vascular cells, and the like. Although ES cells may themselves be used in the treatment of diseases or disorders, the invention also contemplates the productions of differentiated cell types that can be used therapeutically.

The methods of the present invention may be used to generate stem cells from blastomeres wherein the stem cells are hemizygous or homozygous for MHC antigens. These cells are useful for reduced immunogenicity during transplantation and cell therapy. The stem cells so produced may be assembled into a bank with reduced complexity in the MHC genes. The blastomeres of this invention could be derived from embryos that are hemizygous or homozygous for MHC antigens. These embryos may be either selected to be hemizygous or homozygous for MHC antigens or made, by any methods known in the art, to be hemizygous or homozygous for MHC antigens. Alternatively stem cells derived from blastomeres may be made hemizygous or homozygous for MHC antigens, e.g., by gene targeting. See, e.g., WO 03/018760 published Mar. 6, 2003 and U.S. provisional patent application No. 60/729,173 the disclosures of which are incorporated herein in their entirety.

The ES cells and human embryo-derived cells generated by the above-mentioned novel techniques are utilized in research relating to cell biology, drug discovery, and in cell therapy, including but not limited to, production of hematopoietic and hemangioblastic cells for the treatment of blood disorders, vascular disorders, heart disease, cancer, and wound healing, pancreatic beta cells useful in the treatment of diabetes, retinal cells such as neural cells and retinal pigment epithelial cells useful in the treatment of retinal disease such as retinitis pigmentosa and macular degeneration, neurons useful in treating Parkinson's disease, Alzheimer's disease, chronic pain, stroke, psychiatric disorders, and spinal cord injury, heart muscle cells useful in treating heart disease such as heart failure, skin cells useful in treating wounds for scarless wound repair, burns, promoting wound repair, and in treating skin aging, liver cells for the treatment of liver disease such as cirrhotic liver disease, kidney cells for the treatment of kidney disease such as renal failure, cartilage for the treatment of arthritis, lung cells for the treatment of lung disease and bone cells useful in the treatment of bone disorders such as osteoporosis.

Such cell therapy methods may involve use of the ES cells of this invention in combination with proliferation factors, lineage-commitment factors, or gene or proteins of interest. Treatment methods may include providing stem or appropriate precursor cells directly for transplantation where the tissue is regenerated in vivo or recreating the desired tissue in vitro and then providing the tissue to the affected subject.

Pharmaceutical Preparations

The invention provides methods of generating ES cells, ES cell lines, TS cells, and various partially and terminally differentiated cells and cell lines. Cells and cell lines so produced can be studied in vitro and in vivo. In certain embodiments, the study of these cells provides information about basic developmental biology and stem cell biology. In certain other embodiments, the study of these cells and/or the factors that can be used to manipulate the proliferation, differentiation, and survival of these cells can be used to develop stem-cell based therapies to treat or ameliorate any of a variety of diseases or conditions. In other embodiments, cells and cell lines produced by these methods can be used in screening assays to identify agents and conditions that can be used therapeutically. Identified therapeutics may be used to develop cellular therapies or may themselves be useful when delivered to patients.

In certain embodiments, ES cells, ES cell lines, TS cells, TS cell lines, or partially or terminally differentiated cells may be formulated as pharmaceutical preparations by combining the cells with a pharmaceutically acceptable carrier or excipient. In certain embodiments, the pharmaceutical preparation contains a certain number of cells per unit volume of carrier so that cellular therapies can be administered to deliver a particular dosage of cells. For example, pharmaceutical preparations can be formulated to permit delivery of, for example, $1\times10^5$, $1\times10^6$, $2\times10^6$, $3\times10^6$, $4\times10^6$, $5\times10^6$, $1\times10^7$, or greater than $1\times10^7$ cells in a volume of carrier appropriate for the condition being treated and the route of administration.

Methods of Conducting Research

As detailed above, embryonic stem cell research has been partially hindered by political and ethical opposition to the destruction of embryos. The present invention not only provides an alternative method for efficiently generating cells and cell lines, including ES cells and cell lines, the present invention also provides a method that does not require that new embryos be destroyed as part of the process of ES cell derivation. Remaining embryos can be cryopreserved and perpetually preserved or reserved for additional, future research use.

For some, the ability to derive ES cells and cell lines (or partially or terminally differentiated cell types differentiated from ES cells or directly differentiated from embryos) without necessarily destroying new embryos will provide substantial benefits beyond the significant technical advanced reflected in these methods. As such, the invention provides novel methods of conducting embryonic stem cell research without destroying a human embryo. The method entails obtaining a human ES cell or ES cell line derived from a human embryo but without destroying that human embryo. The ES cell or cell line can be generated from a blastomere obtained from a human embryo using any of the methodologies disclosed herein. Once an ES cell or cell line is derived, the method further entails conducting embryonic stem cell research using the human ES cell or ES cell line. The method provides an avenue for conducting ES cell research without the need to destroy new embryos.

In certain embodiments, the embryonic stem cell research involves research examining the differentiation potential of ES cells or cell lines. For example, the research may involve contacting the human ES cell or ES cell line with one or more factors, and identifying factors that promote differentiation of the ES cell or ES cell line to one or more mesodermal, endodermal, or ectodermal cell types. In other embodiments, the embryonic stem cell research involves the study of possible therapeutic uses of ES cells or cell differentiated there from.

Regardless of the particular research use, this method may expand the opportunities for collaboration with researchers around the world, particularly researchers working in countries with laws regulating embryo destruction.

Unless otherwise defined, all technical and scientific terms used herein have the same meaning as commonly understood by one of ordinary skill in the art. In case of conflict, the present specification, including definitions, will control.

Further, unless otherwise required by context, singular terms shall include pluralities and plural terms shall include the singular.

Generally, nomenclatures used in connection with, and techniques of, cell and tissue culture, molecular biology, immunology, microbiology, genetics, developmental biology, cell biology described herein are those well-known and commonly used in the art.

Exemplary methods and materials are described below, although methods and materials similar or equivalent to those described herein can also be used in the practice or testing of the present invention.

All publications, patents, patent publications and other references mentioned herein are incorporated by reference in their entirety.

Throughout this specification and claims, the word "comprise," or variations such as "comprises" or "comprising" will be understood to imply the inclusion of a stated integer or group of integers but not the exclusion of any other integer or group of integers.

The following examples are intended to be illustrative and not limiting in any way.

EXEMPLIFICATION

Example 1

The Effect of Lagging Time Between Nuclear Injection and Enucleation on Pronuclear (PN) Stage Zygotes Nuclear injection was performed on sixty-four PN stage embryos. GFP positive mouse ES cell nuclei were transferred into PN stage zygotes. Embryos were then cultured 3, 6, 9, or 12 hours before enucleating the original pronucleus. The cloned embryos were next cultured and their development was observed. A high percentage of embryos at all time points reached the two-cell stage, but only embryos enucleated 3 hours after nuclear transfer reached the four-cell stage (see Table 2).

TABLE 2

The effect of lagging time between nuclear injection and enucleation on PN stage mouse zygotes.

| Time after injection (hours) | Total # of zygotes | 2C | 4C | <8C |
|---|---|---|---|---|
| 3 | 19 | 11 | 2 | 0 |
| 6 | 19 | 11 | 0 | 0 |
| 9 | 14 | 9 | 0 | 0 |
| 12 | 9 | 6 | 0 | 0 |

Example 2

Serial Cloning Using PN Stage Zygotes and 2-cell Stage Embryos

In an effort to attain further development of cloned embryos, serial cloning was performed. Nuclear injection was performed as described in Example 1. Embryos were then cultured 3 hours before enucleating the original pronucleus. The cloned embryos were next cultured until the 2-cell stage.

A transplantation of dissociated individual cloned embryo cells into normal fertilized 2-cell stage mouse embryos was done at 18 hrs after the first cloning. The recipient embryos were enucleated prior to the nuclear transfer. Individual cloned blastomere cells were transplanted into the perivitellin space of the enucleated 2-cell stage embryos. Electrofusion of the transplanted blastomere and the enucleated embryo was performed by giving a single pulse of 150V DC for 15 microseconds.

Figure 1B:
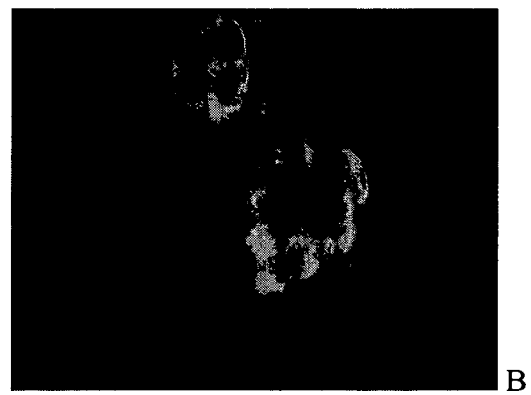

The serially cloned embryos were cultured in KSOM medium and monitored for further development. Two of six embryos developed into blastocysts (FIG. 1A-B). As a control, PN stage zygotes were injected with mouse ES cell nuclei (GFP positive), and their nuclei were enucleated 3 hrs later and cultured in 5% CO2. None of these embryos went on to develop into blastocysts.

TABLE 3

The effect of serial cloning on cloned embryo development.

| Treatments | Total # of zygotes | 2C | 4C | 8C-M | Blastocysts |
|---|---|---|---|---|---|
| Serial cloning | 6 | 5 | 4 | 2 | 2 |
| Control | 6 | 4 | 0 | 0 | 0 |

Example 3

Somatic Cell Cloning Using Two Cell Stage Mouse Embryos

It was hypothesized that cloned blastomeres in a mosaic embryo might be stimulated to develop further by non-cloned cells. One of the two blastomeres of a 2-cell stage mouse embryo was enucleated, and immediately after enucleation, an ES cell nuclei was injected into the enucleated blastomere. Embryos were cultured without any further manipulation in KSOM.

Figure 2A:
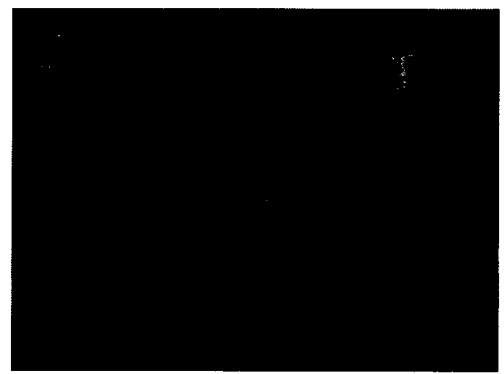
FIG. 2A-2C show the development of 2 cell cloned embryos in the presence of helper cells. Injected GFP positive ES cell nuclei formed mosaic embryos capable of development to the 4-cell stage (A), 8-cell stage (B), and blastocyst stage (C).
Figure 2B:
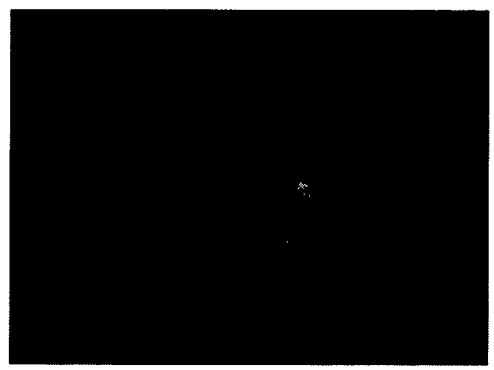
Figure 2C:
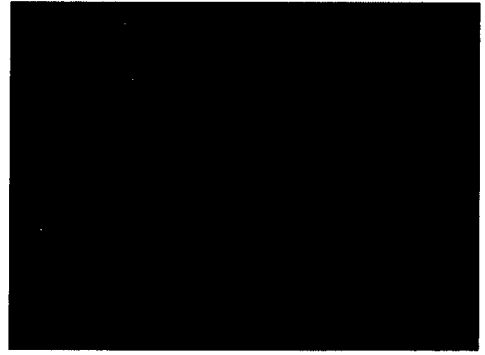

The cloned blastomeres divided the next day and contributed to GFP positive cells forming mosaic embryos (FIG. 2A-C). When these embryos developed to the 8-cell stage at least 3 blastomeres originated from the cloned blastomeres (FIG. 2B). Four of these cloned embryos developed into blastocyts (see Table 4). GFP positive blastomeres integrated into part of the blastocysts.

TABLE 4

The effect of helper cells inside of the same zona pellucida with cloned blastomeres in 2-cell stage cloned embryos.

| Total # of 2 cells | # survived injection | 4C | 8C-M Blastocyst |
|---|---|---|---|
| 14 | 8 | 4 | 4 |

Example 4

Materials & Methods for Examples 1-3

All experiments were done using the mouse strain CD-1. The handling media used was CZB. The culture media used was KSOM. All nuclear donor cells were GFP positive mouse ES cells (CD-1 X Sv129 F1). Nuclear injection was done using a PIEZO drill. Blastomeres were dissociated using a glass pipette. Enucleation was performed microsurgically using a micropipette to remove the polar body and the adjacent cytoplasm in PN stage embryos or the visible nuclei in 2-cell stage embryos.

Example 5

Cloned Blastocyst Development

Developmental rate was significantly affected by the cloning methods. Tables 5 and 6 document the preimplantation development of F2GFP NT embryos derived from single cloning versus serial nuclear transfer using in vivo 2-cell stage embryos. The most significant difference in development was found at the 2-cell to 4-cell transition: 59% versus 97% development in single versus serial cloning, respectively. The attrition was observed in inbred stains as well. Moreover almost all the F2GFP cleaved serial clone embryos developed to expanded or hatched blastocyst stage within 4 days after initial cloning. This rate of development was the same as the in vivo fertilized B6D2 F1 embryos (95%) cultured in KSOM. Clones derived from inbred strains, DBA2 and C57BL/6, showed less effective development compared to F2 GFP; however, blastocyst rate was significantly increased compared to single NT groups (P<0.001).

TABLE 5

Development of F2GFP serial cloned embryos.

| Groups | Total No. 1 cell | Embryo Development (percentage from 1 cell) | | | | | |
|---|---|---|---|---|---|---|---|
| | | Cleaved | 4C | 8C | M | EB | B/HB |
| In vivo fert* | 186 | 98.8 | 98.6 | 95.5 | 95.5 | 95.5 | 95.5 |
| Single clones | 181 | 91.7 | 59.1 | 49.2 | 43.7 | 36.5 | 33.2 |
| Serial clones | 133 | 98.5 | 97.7 | 97.7 | 97.7 | 95.5 | 95.5 |

Different superscripts in same columns represent significant difference (P < 0.01).
*In vivo fertilized B6D2F1 embryos.

TABLE 6

Development of inbred mouse cloned embryos after serial cloning.

| Groups | Total No. 1 cell | Embryo Development (percentage from 1 cell) | | | | | |
|---|---|---|---|---|---|---|---|
| | | Cleaved | 4C | 8C | M | EB | B/HB |
| In vivo fert* | 130 | 98.6 | 98.5 | 98.5 | 98.5 | 96.2 | 96.2 |
| DBA2 single** | 89 | 92.2 | 45.5 | 35.5 | 32.3 | 12.5 | 9.8 |
| DBA2 serial | 90 | 94.4 | 88.2 | 86.4 | 84.7 | 76.5 | 73.1 |
| B6 single*** | 102 | 93.2 | 37.6 | 29.3 | 27.6 | 11.4 | 7.8 |
| B6 serial | 98 | 94.3 | 87.3 | 85.2 | 85.4 | 72.3 | 69.5 |

Different superscripts in same columns represent significant difference (P < 0.01).
*In vivo fertilized B6D2F1 embryos.
**DBA2 inbred strain.
***C57BL/7 inbred strain.

Example 6

Live Pup Development

Figure 3:
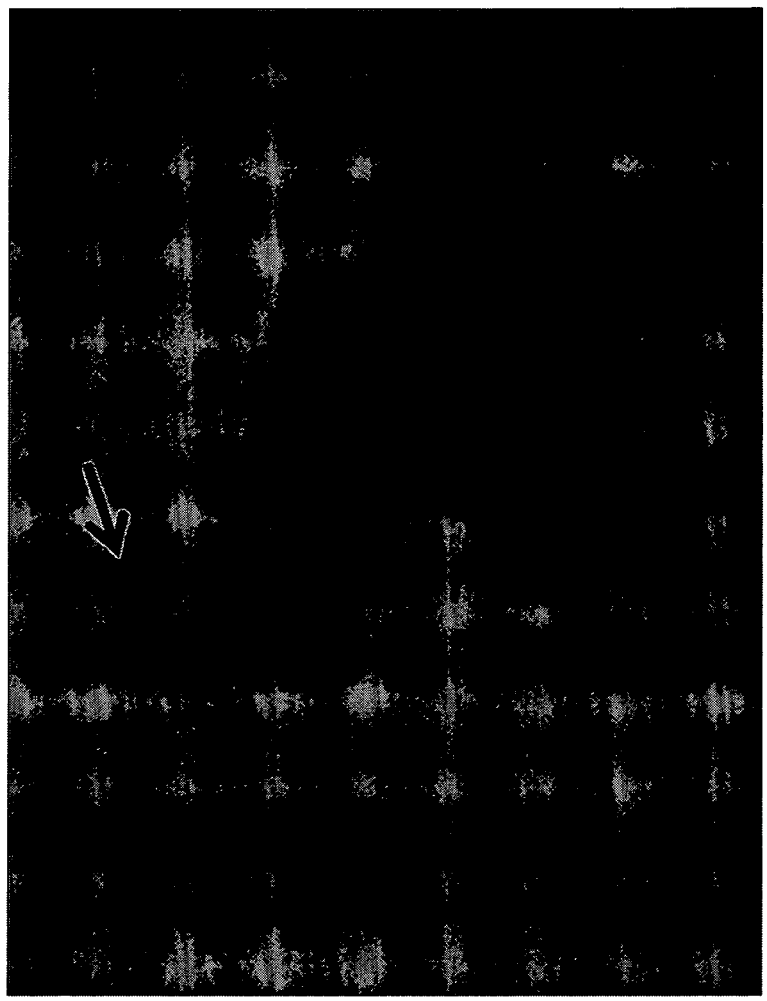
FIG. 3 shows cloned F2GFP mice. 10 week old F2GFP mice emitting green fluorescence under UV light (arrow).

To assess the ability to develop to term, a total of 35 two-cell stage embryos constructed by serial nuclear transfer using F2 GFP cumulus cell nuclei were transferred into 4 pseudo pregnant females (0.5 d.p.c). A total of 6 live pups were recovered by caesarean section at 19.5 days of gestation. All the 6 pups were successfully fostered to surrogate mothers and grew up normally and matured (FIG. 3). In contrast, the production of clones from the single transfer technique using same F2 GFP cumulus cell nuclei yielded only 1 pup out of 98 embryos transferred (Table 7).

To investigate whether the same technique can be applied to generate inbred strains of mice we used DBA2 and C57BL/6 inbred mice. A total of 2 pups (1.6%) were recovered by caesarean section at 19.5 days of gestation from DBA2 serial clones, but no viable pups were found in C57BL/6 clones regardless of cloning methods used. Of the two DBA2 pups, one pup died from respiratory deficiency within few minutes after recovery. The remaining pup did not show any sign of breathing difficulty but was deserted and partially eaten few hours after introduction to the foster mother (Table 7).

Figure 4:
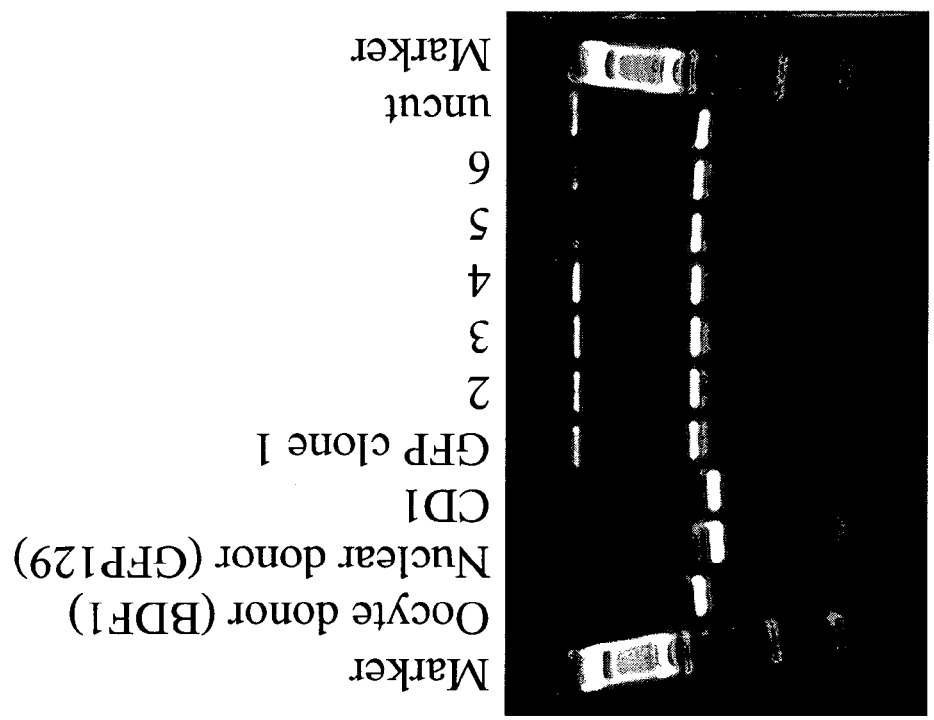
FIG. 4 shows confirmation of GFP cloned mice genetic makeup.
Figure 4:
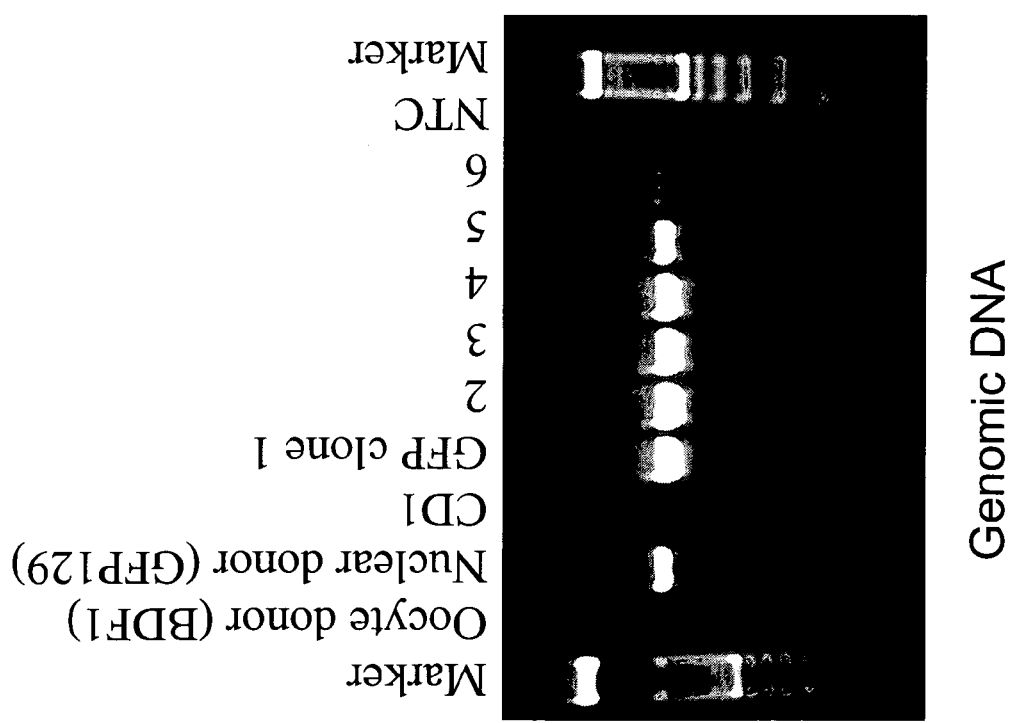
Figure 5:
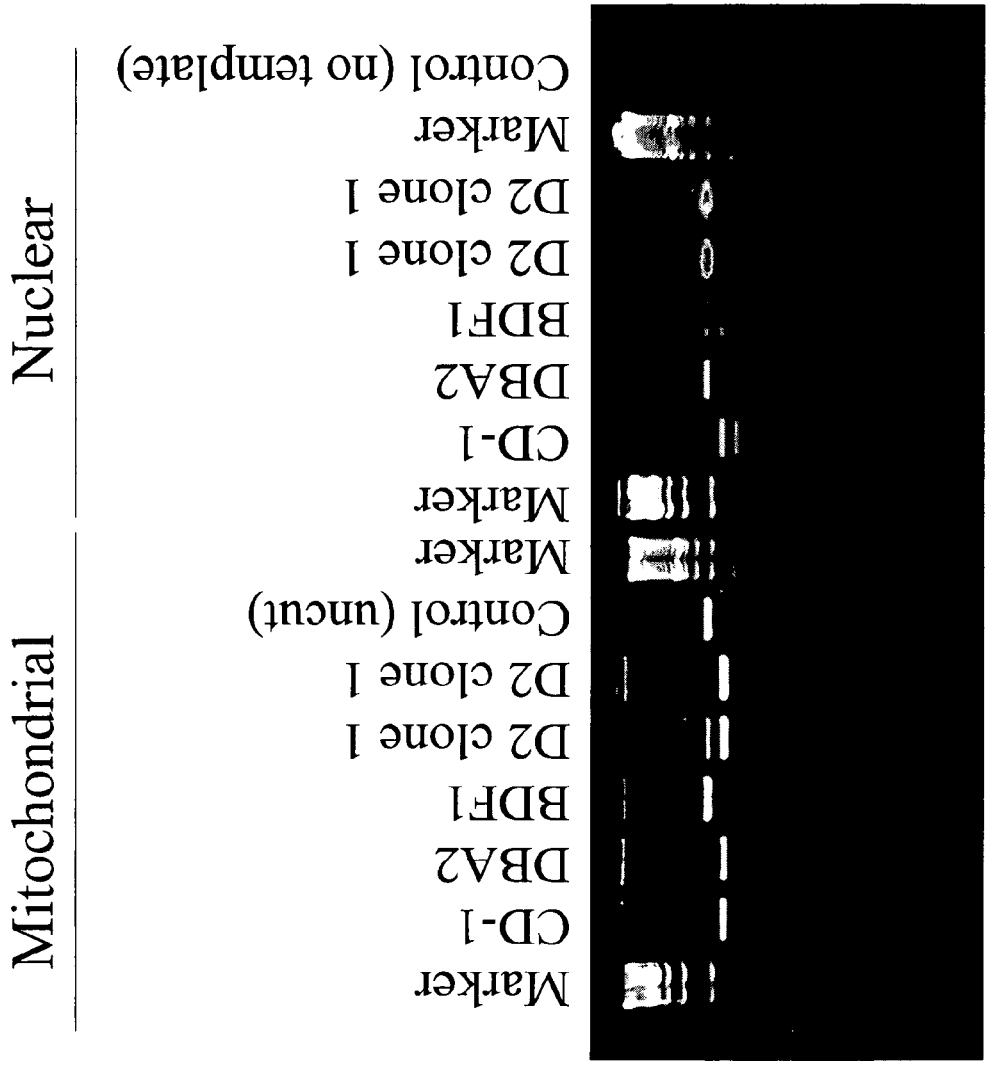
FIG. 5 shows DBA2 clone 1 fingerprinting.

To confirm that the cloned mice were derived from the cumulus cells of F1GFP and DBA2 mice, we demonstrated the presence two mouse microsatellite markers D1MIT46 as described previously, and the Nd3 C9461T polymorphism was analyzed by restriction fragment length polymorphism (RFLP) for mitochondrial DNA(19) (FIGS. 4 & 5.). These studies demonstrated that the cloned mice were genetically identical to the donor mice from which the cumulus cells were prepared. The mitochondria RFLP of cloned mice was matched to that of cytoplasm donor B6D2F1 strain (FIGS. 4 & 5) providing direct evidence for the origin of the cytoplasm (recipient). The F2GFP clones emitted green fluorescence under UV light, providing further evidence for the genetic origin of the clones (FIG. 3).

TABLE 7

The results of cloned embryo transfer.

| | Mouse strains | | | | | |
|---|---|---|---|---|---|---|
| | GFP CD-1/129 | | DBA2 | | C57BL/6 | |
| | single | serial | single | serial | single | serial |
| Total No. Transferred | 98 | 35 | 102 | 120 | 107 | 115 |
| No. of Implantation | 35 | 18 | 9 | 28 | 7 | 17 |
| No. of Live pups | 1 | 6 | 0 | 2 | 0 | 0 |
| Percentage of live pups | 1 | 17 | 0 | 4 | 0 | 0 |

No gross abnormalities in the postnatal growth and behavioral development of the cloned animals were observed. Interestingly, the animals cloned using nuclear retransplantation did not express the obese phenotype that has been documented in adult cloned mice. The obesity of adult cloned mice has been attributed to gene expression abnormalities and epigenetic modifications during NT and embryo culture, and reflects an increase of adipose tissue in addition to larger body size beginning at 8-10 weeks of age. Mean weight (±SD) of mice cloned using nuclear retransplantation were 34.9±0.8 grams at six months, which did not differ (P>0.1) from normal control animals (33.6±1.9). By contrast, animals cloned using traditional SCNT weighed 54.8±2.6 grams at three to six months of age (Table 8).

TABLE 8

Weight of mice cloned using traditional SCNT versus nuclear retransplantation

| Mouse months | Number of animals | weight (gm) at 3-6 | | |
|---|---|---|---|---|
| | | Mean | ± | SD |
| BDF1 Traditional SCNT | 5 | 54.8$^a$ | | 2.6 |
| BDF1 retransplantation | 2** | 26.3$^b$ | | 2.9 |
| BDF1 normal controls | 7 | 24.9$^b$ | | 0.3 |

*Means with different superscripts differ (P < 0.01).
**1 clone is 3 months old, and the other one is 6 months old. Single cloned mice and normal mice were at least 6 months old.

Example 7

Gene Expression Profile of Cloned Blastocyst Stage Embryos

Figure 6:
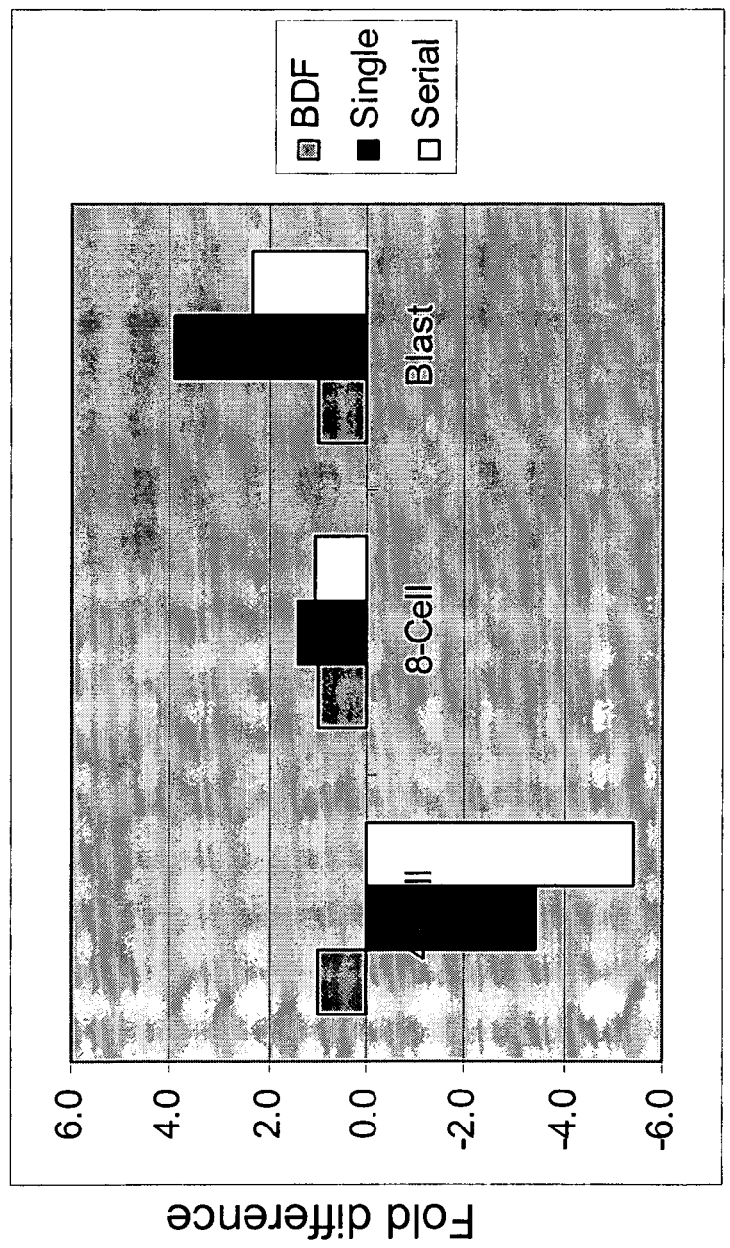
FIG. 6 shows H19 gene expression in F2GFP cumulus cell cloned embryos.
Figure 7:
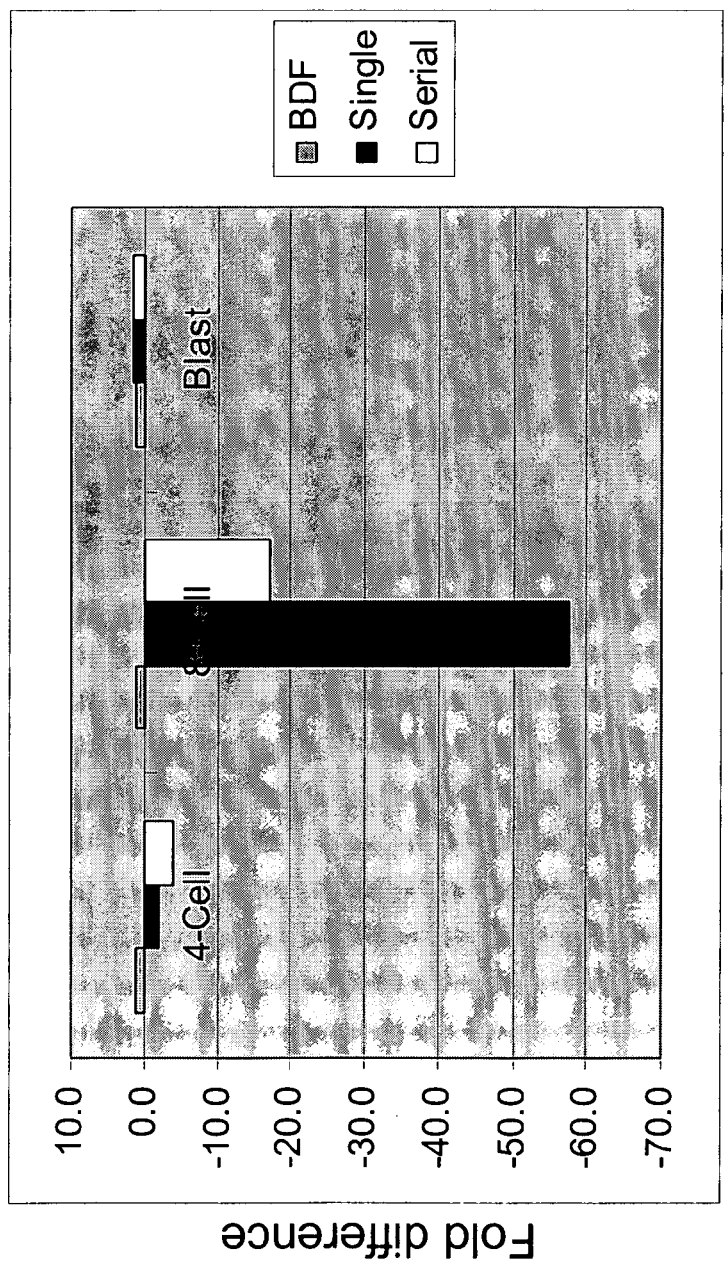
FIG. 7 shows IGF-2 gene expression in F2GFP cumulus cell cloned embryos.
Figure 8:
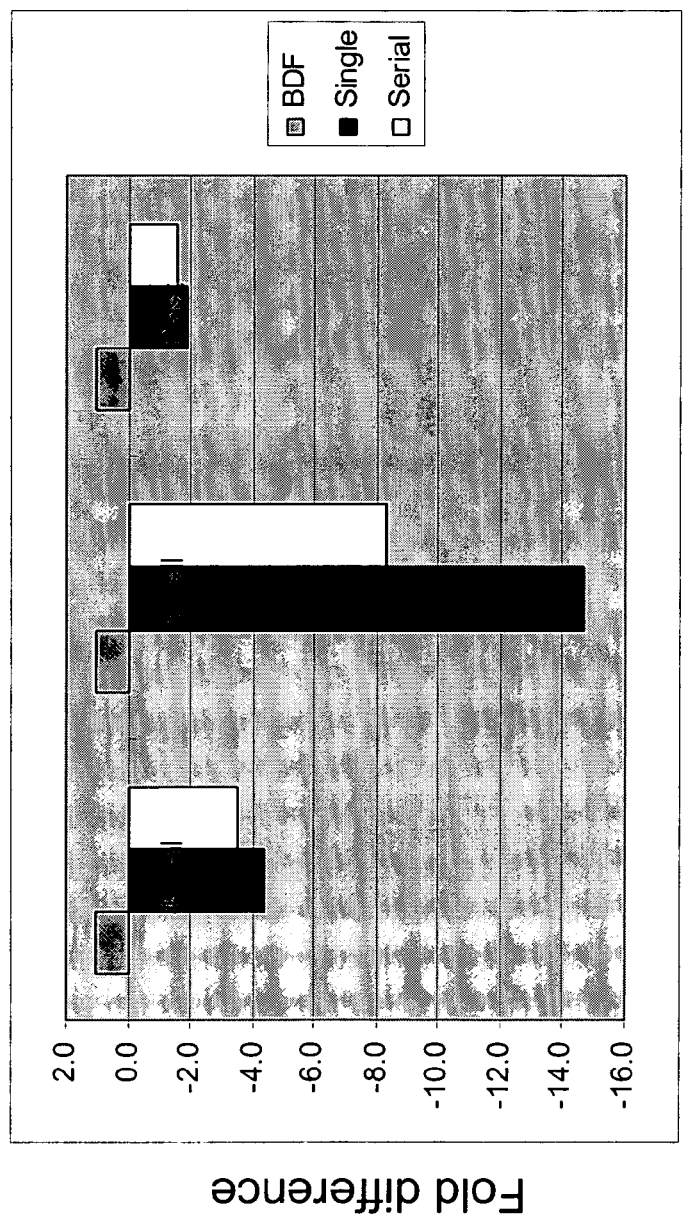
FIG. 8 shows Oct-4 gene expression in F2GFP cumulus cell cloned embryos.
Figure 10:
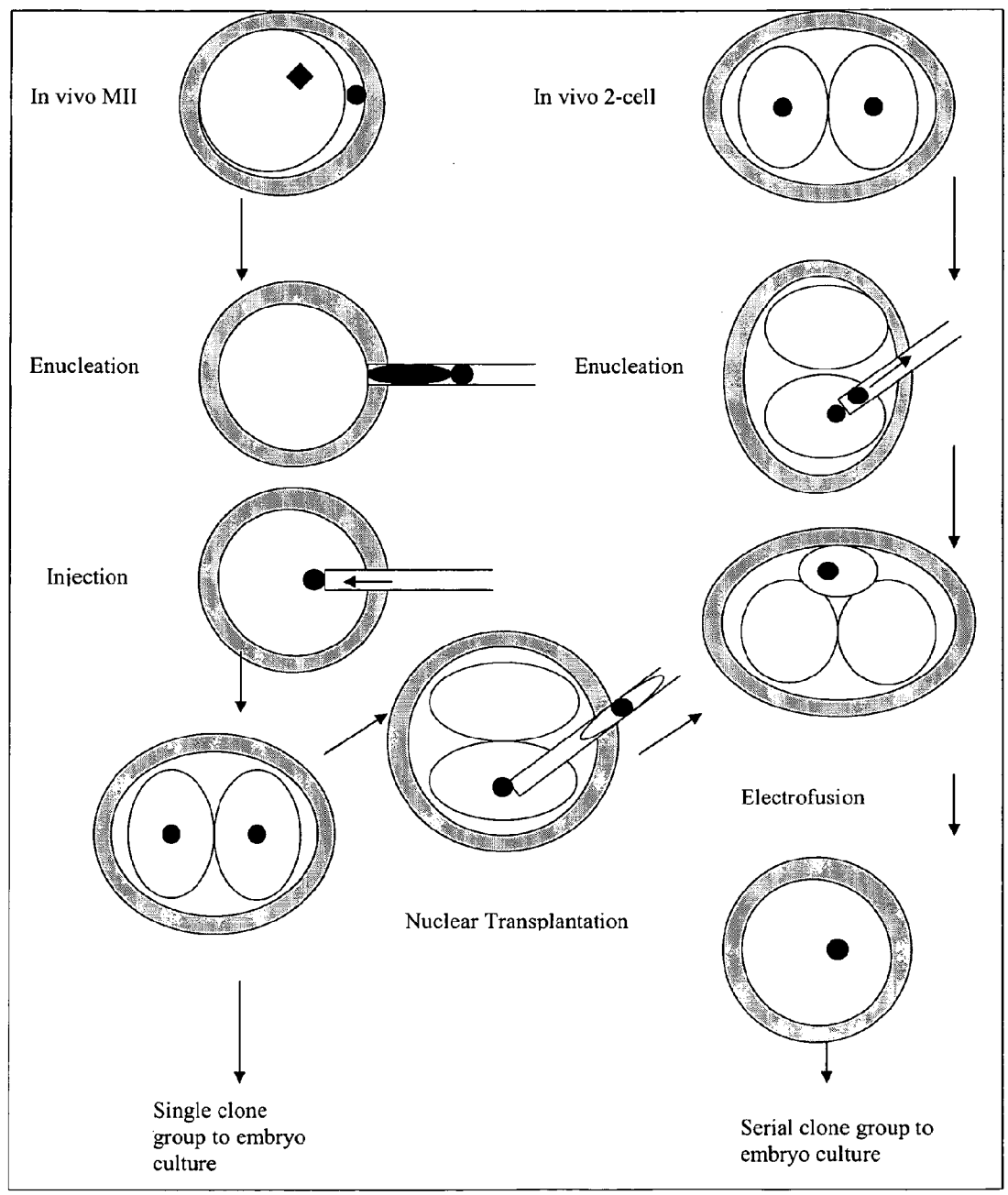
FIG. 10 shows a schematic of the nuclear transfer and serial nuclear transfer methods.

Numerous studies strongly indicate faulty epigenetic reprogramming in reconstructed embryos, which may account for their poor performance in both in vitro cultures and in vivo development after transfer. Since our serial cloning resulted in a dramatic increase in cloned embryo development up to hatched blastocyst stage, we hypothesized that the gene expression pattern of several genes may be similar to that of normal in vivo fertilized embryos. To examine our hypothesis we analyzed the expression of two imprinted genes, H19 and IGF2, and one pluripotency-associated gene, OCT-4, at 4-cell, 8-cell, and blastocyst stages. As presented in FIGS. 6 through 8, expression of all three genes in serial cloned embryos, compared to single cloned embryos, was more similar to that of in vivo B6D2F1 control embryos. In particular, H19 gene expression in serial cloned blastocysts was notably different from the single cloned counterpart and much closer to that of the B6D2F1 control (FIG. 6). Serial cloned 8 cell stage embryos significantly up-regulated IGF2 expression compared to single cloned embryos, closer to levels in the B6D2 F1 control (FIG. 7). The same trend was found in OCT-4 expression in all developmental stages studied (FIG. 8).

Example 8

Cell Number Counts of Blastocyst-stage Embryos

Abnormal gene expression patterns in blastocyst-stage clones is coincident with less than half the normal number of cells and higher cell number correlates with improved cloning efficiency and correct expression of OCT-4. Nuclear retransplantation significantly increased both the total cell number as well as the number of inner cell mass (ICM) cells of cloned blastocysts (Table 9). Traditional SCNT (n=14 embryos) yielded 32.3±4.6 cells (8.3±5.9 ICM cells)/blastocyst versus 67.4±6.5 cells (28.7±4.8 ICM cells) for normal in vivo fertilized embryos (n=15, P<0.001). Blastocysts generated via nuclear retransplantation (n=15) contained a total of 49.8±6.9 cells and 16.2±7.1 ICM cells, representing an approximately 1.5- and two-fold improvement, respectively. The mean ICM/trophectoderm (TE) cell ratio also increased from 0.33 to 0.48 (45%) (P<0.01) (Table 9). The higher ICM/TE ratio and cell numbers may account, at least in part, for the marked improvement in postimplantation development and survive to birth after transfer into surrogate mothers.

TABLE 9

Blastocyst quality analysis by differential staining of inner cell mass (ICM) and trophectoderm (TE) cells of blastocysts after single or serial nuclear transfer.

|  | No. Blastocysts | Total cell No. Mean ± SD) | ICM (Mean ± SD) | TE (Mean ± SD) | Ratio ICM/TE (Mean ± SD) |
| --- | --- | --- | --- | --- | --- |
| Single | 14 | 32.3  4.6 | 8.3  5.9 | 24.3  9.7 | 0.33 |
| Serial | 15 | 49.8  6.9 | 16.2  7.1 | 33.5  8.6 | 0.48 |
| BDF1 | 15 | 67.4  6.5 | 28.7  4.8 | 39.6  5.7 | 0.71 |

Example 9

Embryonic Stem Cell Derivation from Cloned Embryos and Their Characterization

A total of 35 single cloned F2GFP blastocysts and 30 serial cloned blastocysts were subjected to ES cell isolation. Of these, 1 ES cell line (3%) from a single cloned embryo and 5 ES cell lines (17%) from serial cloned embryos were established (Table 10). All established cell lines were positive for alkaline phosphatase, OCT-4, and SSEA1 (FIG. 9A). In addition, all these nuclear transfer ES cell lines formed embryoid bodies in vitro, and teratomas when injected intramuscularly into the hind limb (FIG. 9B). Both samples showed differentiated tissues originating from all three germ layers. Furthermore, when these ntES cells were injected into 8-cell stage CD-1 embryos and transferred to surrogate females (2.5 d.p.c.), several chimeric mice were produced with definite spotted agouti coat and emission of green fluorescence when irradiated with UV light, indicating F2GFP genotype (FIG. 9C).

TABLE 10

The efficiency of embryonic stem cell derivation from cloned embryos.

|  | No. of blastocysts plated | No. of initial outgrowths | No. of established ES cell lines (%) |
| --- | --- | --- | --- |
| Single | 35 | 35 | 1 (3%) |
| Serial | 30 | 27 | 5 (17%) |
| SV129 | 24 | 22 | 7 (29%) |

Example 10

Materials and Methods for Examples 5-9

Animals

Female DBA2, C57BL/6, and F2 GFP hybrid mice were used as nuclear donors. To generate F2 GFP mice, female 129/SV mice were crossed with a 129/ CD F1 male (129/Sv x CD-1) carrying and expressing the gene for green fluorescent protein (GFP). For the initial and serial cloning, enucleated BDF1 (C57BL/6 x DBA/2) oocytes and enucleated 2 cell stage BDF1 embryos, respectively, were used as recipients. CD-1 females were used as surrogate mothers to gestate the cloned embryos.

Media

Oocytes and embryos were cultured in KSOM (Specialty Media, USA) containing amino acids, glucose, and 1 mg/ml bovine serum albumin (BSA) at 37° C. in a high humidity incubator with 5% $CO_2$ in air. Oocyte enucleation was performed in M2 medium (Specialty Media, USA), and cell injections were performed in Hepes-buffered CZB medium at room temperature for initial cloning. The activation of reconstructed oocytes was carried out in $Ca^{2+}$-free CZB containing 10 mM $SrCl_2$ and 5 ug/ml cytochalasin B to prevent polar body extrusion. Nuclear retransplantation was performed at 37° C. in M2 medium (Specialty Media, USA) supplemented with 7.5 ug/ml cytochalasin B and 0.4 ug/ml Nocodazole, a microtubule polymerase inhibitor, to facilitate micromanipulation. The reconstructed embryos were pulsed in manitol-based fusion medium composed of 0.27 mM manitol, 100 μm $MgSO_4$ and 50 μm $CaCl_2$, supplemented with 0.3% bovine serum albumin.

Isolation of Cumulus Cells, Oocytes, and 2-cell Stage Embryos

Superovulation was performed using mature BDF1, DBA2, C57BL/6, and F2 GFP female mice 8-10 weeks old. Mice were injected with equine chorionic gonadotrophin (eCG) (5 IU) and human chorionic gonadotrophin (hCG) (5 IU) 48 h apart. Thirteen hours after hCG injection, cumulus-oocyte complexes were collected from oviducts, and cumulus cells were dispersed by a 5 min treatment with 0.1% (w/v) bovine testicular hyaluronidase (150 USP units/ml) in M2 at 37° C. The dispersed cumulus cells were washed in fresh M2 and resuspended in 3% polyvinylpyrrolidone (PVP; Mr 360, 000, ICN Biochemicals, USA) and kept in a refrigerator (4° C.) until use. The 2-cell stage embryos were collected 36 h after hCG injection from plugged females in M2 medium by washing the oviduct with a 1 ml syringe attached to a 27G blunt needle.

Cloning and Serial Cloning

Nuclear transfer was performed according to the method reported by Chung et al.(29). The enucleation was performed using a Nikon inverted microscope (TE300, Japan) equipped with a Narshige injector (Narshige, Japan). The metaphase II spindle of B2DF 1 oocytes was removed in a drop of M2 medium containing 5 ug/ml of cytochalasin B using a 10-12 um pipette by aspiration using a Piezo micromanipulator controller PMM150 (PrimeTech, Japan). The enucleated oocytes were washed thoroughly in CZB medium and kept in an incubator until use. The nuclei of cumulus cells were injected individually after cytoplasm was removed in 3% PVP using a small bore injector pipette (inner diameter 7 um). The removal of cytoplasm was performed such that only small amount of cytoplasm remained around the denuded nucleus. Activation of reconstructed oocytes were carried out in $Ca^{2+}$-free CZB containing 10 mM $SrCl_2$ and 5 µg/ml cytochalasin B for 6 hrs in a high humidified 5.5% $CO_2$ incubator. After activation, reconstructed oocytes were cultured in KSOM medium.

Procedures for serial cloning are depicted in FIG. 4. For the second cloning, one nucleus of a 2 cell stage cloned embryo was removed with minimal cytoplasm and transferred to an enucleated 2-cell stage in vivo fertilized B6D2F1 embryo in M2 medium supplemented with 7.5 ug /ml cytochalasin B and 0.4 µg/ml Nocodazole. The nucleus was placed between the two 2-cell stage cytoplasts. Fusion of the 2-cell stage cytoplasts and the cloned nucleus was performed using a BTX 2001 electro-fusion machine with 2 DC pulses of 2.4 kV/cm for 15 usec in mannitol-based fusion medium described above. The $1^{st}$ pulse was given after alignment of the reconstructed eggs such that the transferred nucleus faced the negative wire and both of the two blastomeres faced the positive wire. After the first pulse, the reconstructed eggs were turned 90 degrees by alignment pulse of 5 volts AC so that the two blastomeres faced the opposite poles, and a second pulse was administered. The pulsed reconstructed embryos were cultured in KSOM after thorough washing, and their fusion was checked 30 min after the $2^{nd}$ pulse. We typically observed over 98% fusion after the first pulse. Only fused embryos were cultured for another three days.

Production of Cloned Offspring

When some cloned embryos had developed to the 2-cell stage, they were transferred to the oviducts of pseudopregnant CD-1 foster mothers (0.5 day post copulation), which had been mated with vasectomized CD-1 males one day earlier. The recipient females were euthanized at 19.5 days post copulation (d.p.c), and their uteri were examined for the presence of fetuses and implantation sites. The live pups were fostered by foster mothers (CD-1) who had delivered pups the same day.

Cell Number Counting in Blastocysts

The total cell number, and TE and ICM cell numbers of blastocysts were counted after differential staining with polynucleotide-specific fluorochromes as described previously. Briefly, embryos that had developed to expanded blastocysts 4.5 days after the initial cloning were exposed to acidic Tyrode's solution (pH 2.1) to remove the zona pellucida. The denuded blastocysts were washed in M2 medium and then labeled with trinitrobenzene sulfonic acid (TNBS; Sigma P-2297) in M2 at 4° C. for 10 min. After removal of excess TNBS, the blastocysts were exposed to anti-dinitrophenol in M2 at 37° C. for 10 min. Then excess antibodies were removed by thorough washing before exposure to guinea pig complement diluted 1:4 in M2 with 2 ug/ml propidium iodide (PI) for 10 min at 37° C. Then the blastocysts were quickly washed in protein free Hepes CZB medium supplemented with 5 ug/ml propidium iodide and then fixed in ice-cold absolute ethanol for 5 min. The blastocysts were then moved to 10 ug/ml Hoechst 33258 in ethanol for at least 10 min at 4° C. The stained blastocysts were mounted in 100% glycerol and evaluated by fluorescence microscopy (Nikon TE200, Japan). Blue nuclei were counted as inner cell mass (ICM) while red nuclei were considered trophoblast (TE) cells.

Establishment of ntES Cell Lines

When F2 GFP cloned embryos had developed to the blastocyst stage, they were used to establish ntES cell lines as described previously with minor modifications. Briefly, zonae pellucidae were removed before plating by brief exposure to acidic Tyrode's solution and vigorous washings. A group of 3 or 4 denuded blastocysts were placed on the monolayer of mitomycin-C treated mouse embryonic fibroblasts (MEF) grown in one well of a 4-well dish (Nunclon, USA) with 500 ul mouse ES cell culture medium supplemented with 2000 units/ml leukemia inhibiting factor (Chemicon. USA) and 50 µM MEK-1 inhibitor (Cell Signaling Tech, USA). When the inner cell mass formed initial outgrowth (generally within three days), this clump of cells was dissected to smaller pieces by treating them with 0.05% trypsin/EDTA and pipetting with a small bore pipette. The dissected cell clumps and dispersed cells originating from same embryo were transferred to fresh MEFs grown in 50 ul drops of mouse ES cell culture medium covered with tissue culture mineral oil. The culture drops were observed daily for the presence of ES cell outgrowth. The outgrowths were then passed to wells of a 4-well dish containing fresh MEFs.

DNA Isolation

DNA was isolated using the DNeasy Tissue Kit as recommended by the manufacturer (QIAgen, USA), from tail tips of the foster mother strain CD-1, the oocyte donor strain B6D2F1, the nuclear donor strains (F2GFP and DBA2), and the somatic cell nuclear transfer-derived animals (clones 1-6 for F2GFP and clone 1 for DBA2). DNA was quantified using a Nanodrop spectrophotometer (NanoDrop, USA)

Mitochondrial DNA RFLP Analysis

The Nd3 C9461T polymorphism was confirmed by restriction fragment length polymorphism (RFLP) analysis as previously described (19). Briefly, a 204 by fragment containing the 9461 site was amplifed by PCR. The primer-generated mutation together with the C9461 wild-type version produces a recognition site for BclI. As a result, the presence of the T9461 polymorphism disrupts the restriction site. Fragments were analyzed by electrophoresis in a 4% agarose gel.

Nuclear GFP DNA PCR Analysis

Genomic DNA from F2 GFP clones was isolated from tail tips as described above, and 100 ng per reaction was used for GFP gene amplification by PCR. We used forward (5'-ttgaat-tcgccaccatggtgagc-3') and reverse (5'-ttgaattcttacttgta-cagctcgtcc-3') primers for GFP gene with reaction parameters of 95° C. for 9 min (1 cycle) and 94° C. for 45 s, 59° C. for 1 min, 72° C. for 1.5 min for 37 cycles. PCR products were separated on 1.5% agarose gel and visualized by ethidium bromide staining.

DNA Typing

The D1Mit46 simple sequence repeat (SSR) polymorphism was used to genotype nuclear DNA from tail tip DNA by using MapPairs assay B219 forward and reverse unlabelled primers (Invitrogen, USA). The reaction parameters included 20 ng of template, 1× FailSafe Premix K (EpiCentre, USA), 0.2 µM of each primer, 0.5 units of FailSafe PCR Enzyme mix (EpiCentre, USA), and cycling conditions of 96° C. for 2 min (1 cycle), 94° C. for 45 s, 55° C. for 45 s, 72° C. for 1 min for 30 cylces, and 72° C. for 7 min. PCR products were separated on a 4% agarose gel and visualized by ethidium bromide staining. The PCR was carried out for 30 cycles, and the product was separated by 3% agrose gels and visualized by ethidium bromide staing.

Imprinted Gene Expression Analysis

Total RNA was isolated using TRIzol extraction and PureLink purification columns (Invitrogen, USA), from 20 to 30 4-cell, 8-cell and hatching blastocyst stage embryos. Total RNA was reverse-transcribed using the cDNA archive kit as recommended by the supplier (Applied Biosystems. USA) and used as template for quantitative real-time PCR using TaqMan chemistry, the predesigned gene expression assays for H 19, IGF2, OCT-4 and the endogenous housekeeping gene GAPDH, and the ABI SDS 7900HT Instrument as recommended by the supplier (Applied Biosystems. USA). Relative quantitation of gene expression was performed using the comparative threshold cycle method as previously described and using RQ Manager and Excel as recommended by the manufacturer (Applied Biosystems.USA).

Statistical Analysis

The outcomes were evaluated using Chi-square tests corrected for continuity.

Example 11

Human Embryonic Stem Cell Lines Generated without Embryo Destruction

A series of nine experiments was carried out using leftover embryos produced by IVF for clinical purposes. The embryos were obtained with full informed consent and used in compliance with Advanced Cell Technology's Ethics Advisory Board (EAB) and Institutional Review Board (IRB). Pronuclear stage embryos were thawed and cultured in Quinn's cleavage medium in 6% CO2 to the 8-cell stage. Embryos were scored using a standard system and a total of forty-one Grade I or II embryos used in two groups of experiments (Table 11). As in PGD, only one (or in a few [7/41] cases, two) blastomeres was removed from each embryo using a biopsy procedure previously described (Klimanskaya et al. Nature 2006; 444(7118):481-485). In the first set of experiments both parental embryos and blastomeres were cultured together in the original microdrop for 12 hours and then transferred to Quinn's blastocyst medium for an additional 48 hours. Twenty-two of the 26 biopsied embryos (85%) continued development to the blastocyst stage, and most (21/31) of the single blastomeres divided, forming either cell clumps or "embryonic vesicles" comprising 4-8 cells. They were transferred to microdrops of blastocyst medium supplemented with laminin and fibronectin and seeded with mitotically inactivated mouse embryonic fibroblasts (MEF). The following day, the microdrops were merged with microdrops containing green fluoresecent protein (GFP)-expressing hES cells as previously described. Most single-blastomere-derived cell aggregates formed cavitated embryonic vesicles, which were forced to attach by poking them with a 26 G needle if they did not attach spontaneously within 28 hours after plating.

In the second set of experiments the parental embryos and blastomeres were co-cultured together for less than 12 hours after the biopsy procedure. The parental embryos were moved to Quinn's blastocyst medium where they were allowed to continue development to the blastocyst stage. The biopsied blastomeres, regardless of cell division, were transferred to blastomere microdrops as described above and cultured for approximately 5 days without merging with the other GFP ES cell containing drops. Importantly, "embryonic vesicles" did not form under these conditions, but almost all (9/11) blastomere-derived cell aggregates produced outgrowths (Table 11).

In both sets of experiments, the parental embryos were allowed to develop to the blastocyst stage and frozen. Eighty to 85% of the biopsied embryos formed healthy blastocysts (Table 11 and FIG. 11C), a rate consistent or higher than previously reported for both biopsied and non-biopsied embryos (Geber and Sampaio. Hum Reprod 1999; 14(3):782-786; Palmer et al. Hum Reprod 2002; 17(1):25-31).

Figures 11A, 11B, 11C:
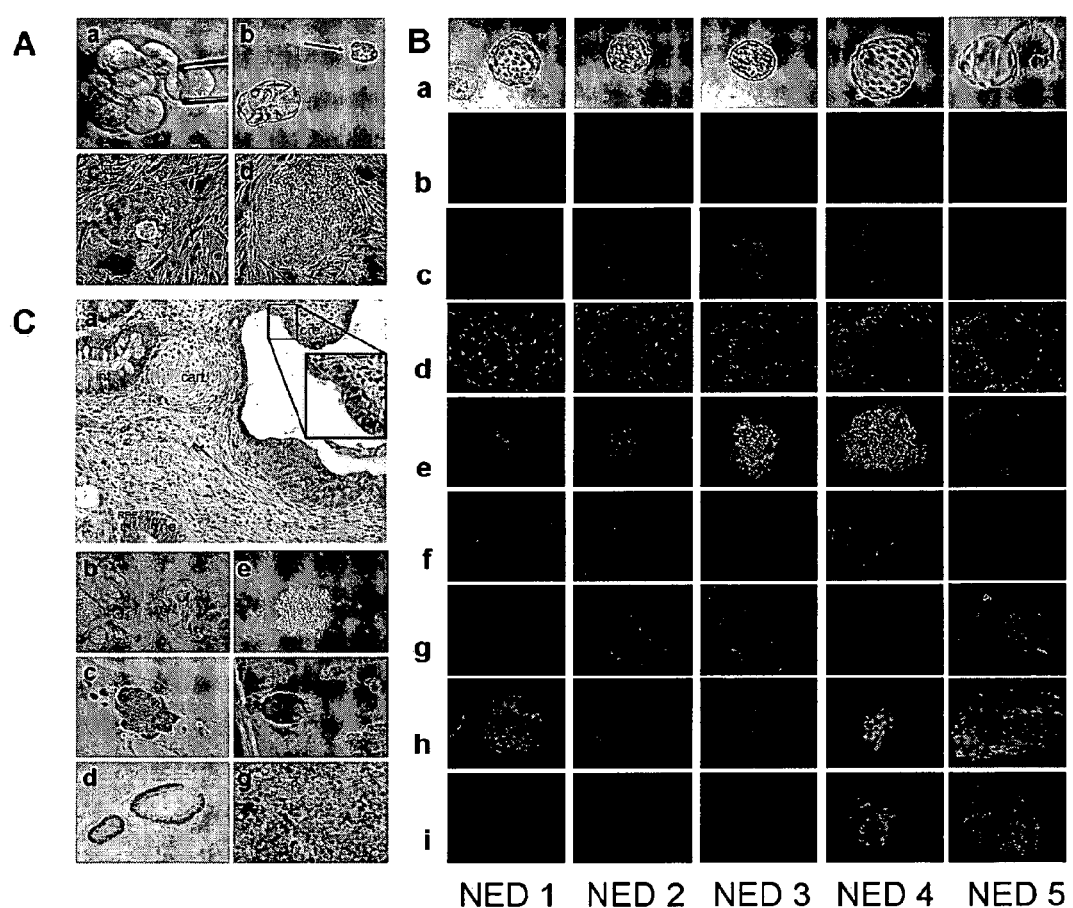
FIG. 11A-C show the derivation and characterization of hESC lines from single blastomeres without embryo destruction. Panel A: Stages of derivation of hES cells from single blastomere. (a)—blastomere biopsy, (b)—biopsied blastomere (arrow) and parent embryo are developing next to each other, (c)—initial outgrowth of single blastomere on MEF, 6 days, magnification ×200, (d)—colony of single blastomere-derived hES cells, magnification ×200. Panel B: Blastocysts formed by the biopsied parental embryos (a) and markers of pluripotency in single blastomere-derived hES cell lines (b-i); (b) alkaline phosphatase, (c)—Oct-4, (d)—DAPI corresponding to Oct4 and Nanog, (e)—Nanog, (f)—SSEA-3, (g)—SSEA-4, (h)—TRA-1-60, (i)—TRA-1-81; original magnification: Panel A(a), 400×, panels A(b-d) and B, 200×, except NED5 g & h, 100×. Panel C: differentiation of single-blastomere-derived hESCs into three germ layers in vivo (a-d) and in vitro (e-g). (a)—teratoma showing derivatives of all three germ layers. cre, ciliated respiratory epithelium, including inset at higher magnification showing cilia; int, intestinal epithelium; cart, cartilage; ne, columnar neuroepithelium with associated retinal pigmented epithelium (rpe). (b-d), examples from other teratomas. (b) bronchiolar nests; (c) muscle stained for smooth muscle actin; (d) intestinal epithelium stained for cdx2. (e-g)—examples of in vitro differentiated derivatives: (e) hemangioblast colony with both hematopoetic and endothelial potential. (f) an embryoid body with beating heart cells (g), retinal pigment epithelium. Magnification: a-f 200×, g 100×.

Twenty-nine of the 33 (88%) blastomere-derived aggregates generated cellular outgrowths, whereas 4/20 (20%) and 4/9 (44%) of the outgrowths from the first and second set of experiments morphologically resembled hES cells (Table 11 and FIG. 11a). In the first set of experiments, only one of the 26 embryos (3.8%) generated a stable hES cell line, which is consistent with the low efficiency previously reported (Klimanskaya et al. Nature 2006; 444(7118):481-485). However, in the second set of experiments, when the biopsied blastomeres were placed in hES cell-growth-favoring conditions, three out of 15 embryos (20%) generated stable hES cell lines, a derivation rate comparable with that obtained using blastocysts.

Figures 12A, 12B, 12C, 12D, 12E, 12F, 12G, 12H, 12I:
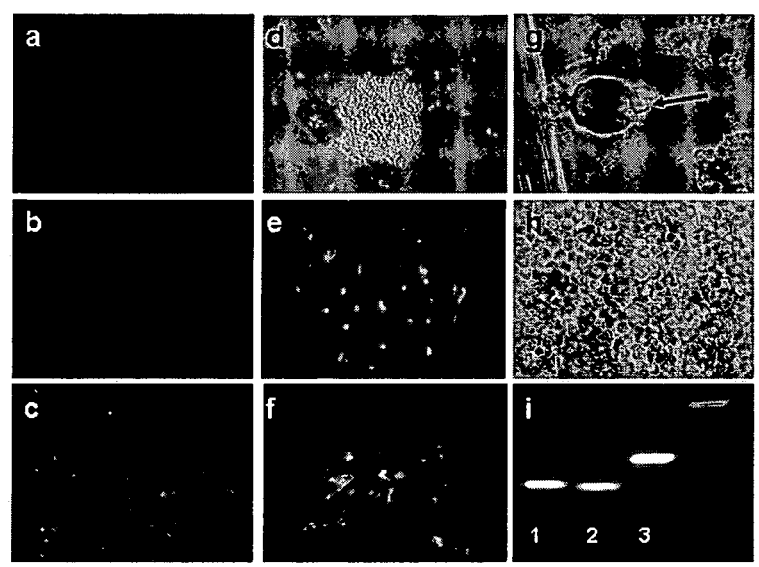
FIG. 12A-12I show examples of differentiation of single-blastomere-derived hES cells into three germ layers (a-c) and cell types of therapeutic value (d-i). Immunostaining with antibodies to the markers of three germ layers: tubulin β III (a), smooth muscle actin (b), a-feto protein (c). Examples of differentiated derivatives: hemangioblast colony (d) with both hematopoetic and endothelial potential. Immunostaining of endothelial cells with antibodies to KDR (e) and CD31 (f); an embryoid body with beating heart cells (g), retinal pigment epithelium (h,i). RT-PCR shows RPE markers PEDF (lane one, 300 bp) and RPE65 (lane 2, 285 bp), positive control GAPDH (lane 3, 465 bp). Magnification: a-c, e,f—20×; d,g—10×, h—40×.

When the blastomere-derived (hES cell-like) colonies reached approximately 50 cells or more, they were mechanically dispersed and the pieces plated next to the initial outgrowths. Secondary colonies were also allowed to grow to a similar size, and mechanically passaged onto fresh MEF every 3-5 days until they adapted to routine passaging with trypsin and could be frozen (usually after 7-10 passages) as previously described (Klimanskaya and McMahon. Handbook of Stem Cells. San Diego: Elsevier Academic Press; 2004 p. 437-449). At each passage, the colonies were screened under a fluorescent microscope for the absence of GFP-positive cells. All four hES cell lines were positive for Oct-4, nanog, SSEA-3, SSEA-4, TRA-1-60, TRA-1-81, and alkaline phosphatase (FIG. 11b). In vitro differentiation confirmed the presence of derivatives from all three germ layers, hematopoietic and endothelial cells, neurons, retinal pigment epithelium (RPE), beating cardiomyocytes, and other cell types of therapeutic importance (FIG. 12). To assess the in vivo differentiation potential, the cells were injected under the kidney capsules of NOD-SCID mice, where they formed teratomas in approximately 6 to 8 weeks, differentiating into structures of all three germ layers.

Figures 13A, 13B:
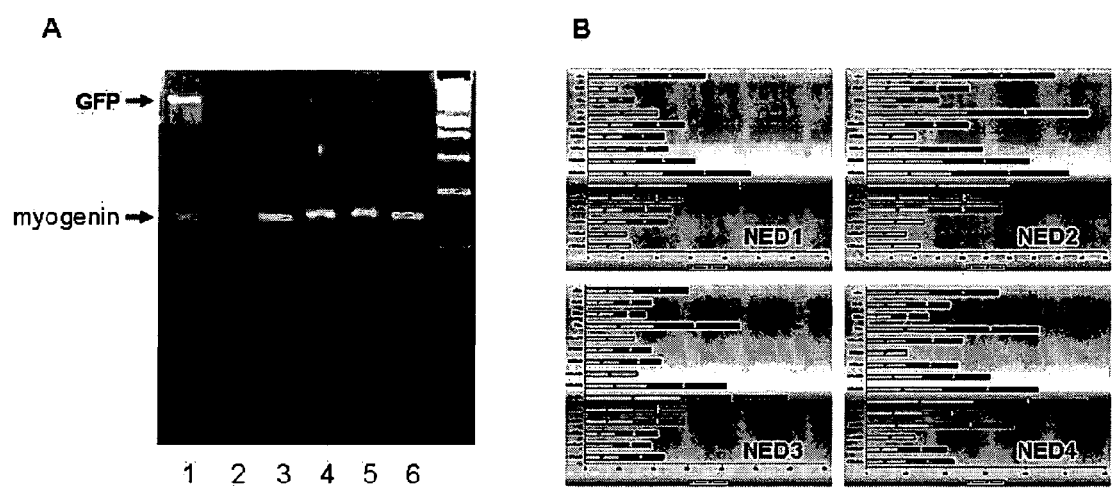
FIG. 13A-13B show microsatellite and PCR analysis of single-blastomere-derived hES cells. A—DNA PCR confirming the absence of GFP in single blastomere-derived hES cells. Lane 1, positive control WA01(H1) hES cell line, lane 2, negative control (no template), lane 3, NED1, lane 4, NED 2, lane 5, NED 3, lane 6, NED4. B—Microsatellite analysis of the single blastomere-derived hES cell lines.
Figure 14:
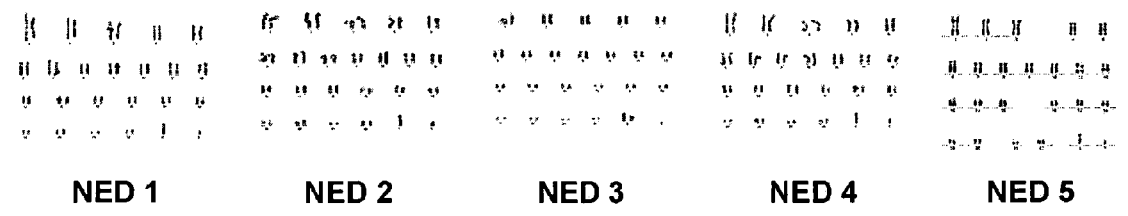

All four of the newly established hES cell lines had normal karyotypes (No Embryo Destruction [NED]1, 46 XY; NED2, 46 XY; NED3, 46 XX; and NED4 46 XY (FIG. 14). PCR analysis confirmed the absence of GFP DNA, which eliminated the possibility of cross-contamination or fusion with the GFP+hES cells used for co-culture (FIG. 13a) Further genotyping analysis showed the unique identity of the new hES cell lines, ruling out any potential cross-contamination with other hES cell lines currently maintained in our laboratory (FIG. 13b). In the first series of experiments, 21 of the embryos had one blastomere biopsied, whereas 5 (from exps no 1 & 3) had two single blastomeres removed. In the second series of experiments 13 of the embryos had one blastomere biopsied, whereas 2 embryos (from exps 8 & 9) had two single blastomeres removed.

TABLE 11

Derivation of hES cells from single blastomeres without embryo destruction

| Exp. No. | No. embryos biopsied | No. developingng to blastocysts | No. blastomeres that divided | No. outgrowths | No. hES cell outgrowths | No. hES cell Lines established |
|---|---|---|---|---|---|---|
| Original method | | | | | | |
| 1 | 6 | 5 | 5/9 | 5 | 1 | 0 |
| 2 | 6 | 6 | 6/6 | 5 | 1 | 1* |
| 3 | 4 | 4 | 4/6 | 4 | 0 | 0 |
| 4 | 4 | 3 | 3/4 | 3 | 0 | 0 |
| 5 | 6 | 4 | 3/6 | 3 | 2 | 0 |
| Total | 26 | 22 (85%) | 21/31 67%) | 20 | 4 | 1 (4%) |
| New method | | | | | | |
| 6 | 4 | 3 | 3/4 | 2 | 2 | 1* |
| 7 | 3 | 3 | 2/3 | 2 | 0 | 0 |
| 8 | 4 | 3 | 3/5 | 3 | 1 | 1** |
| 9 | 4 | 3 | 3/5 | 2 | 1 | 1* |
| Total | 15 | 12 (80%) | 11/17 65%) | 9 | 4 | 3 (20%) |

*hES cell lines derived from single blastomere-biopsied embryos
**hES cell line derived from one of the two biopsied blastomeres Example 12

Blastomere Biopsy and Culture

In an additional set of experiments a double dose of laminin was used, and the blastomeres were grown in the blastocyst medium with MEF cells for an extended period of time (5 days) to prevent embryonic vesicle formation.

Pronuclear stage human embryos were cultured in Quinn's cleavage medium (Cooper Surgical) up to the 8-cell stage in an incubator with 5% $CO_2$. Individual blastomeres were isolated from embryos as described previously using PIEZO. Briefly, the 8-cell embryos were pre-incubated in $Ca^{++}$ and $Mg^{++}$-free phosphate buffered saline supplemented with 0.05% PVA for 15 min at room temperature to facilitate individual blastomere isolation. The embryos were then, transferred to Quinn's hepes medium for the manipulation. Before inserting a biopsy pipette, a hole (500 µm in diameter) was made on the zona pellucida using a small (20 µm) pipette by applying several pulses of PIEZO. To isolate individual blastomeres, a biopsy pipette (500 µm) was inserted through the hole and grasped a blasomere applying gentle negative pressure. When ⅔ of the blastomere was inside of the pipette, the blasomeres were pulled away. After the biopsy, the parental embryos and blastomeres were returned to the original culture drops (Quinn's cleavage medium) and cultured 12 to 18 hrs together. Then the blastomeres and parental embryos were separated: the parental embryos were transferred to blastocyst medium (Quinn's blastocyst medium) to allow them to develop into blastocysts, meanwhile the blastomeres were transferred to a small culture drop (50 µl) containing MEFs. The blastomere culture medium was supplemented with laminin (10 µl/ml), fibronectin (10 µl/ml), or Matrigel (10 µl/ml). They were cultured for 5 days or until they formed cell clumps composed of approximately 20 cells in the same medium. Then the adjacent GFP ES cell culture drops were merged with the blastomere culture drops to allow the two media to mix together. Approximately 24 hrs later, ½ of blastomere clumps were removed and plated in the same culture drop. ES colony formation was checked daily and ½ of culture medium was changed with fresh medium daily. The ES colonies then were split and transferred mechanically to fresh ES cell culture dishes up to passage 4, then the ES cells were gradually adopted to the trypsinization for large scale culture.

Once the blastomeres have developed to embryonic vesicle, almost all of them became trophoblast like cells which have no potential to become ES cells. By preventing the vesicle formation and adding higher laminin, which interferes with cell polarity, most 8-cell blastomeres were directed to become ES cells (Table 12).

TABLE 12

Derivation of ES cell lines from single blastomeres

| Treatment | No. blastomere | No. blastomere Divided | No. initial outgrowth | No. ES cell lines |
|---|---|---|---|---|
| Laminin | 6 | 5 | 4 | 4 |
| Fibronectin | 6 | 5 | 3 | 1 |
| Matrigel | 6 | 4 | 0 | 0 |

Example 13 hESC Co Culture is Not Necessary for hESC Line Derivation

In an additional group of experiments, GFP-hESC co-culture was examined to determine if co-culture is necessary for successful derivation. An experiment was carried out using 2 frozen cleavage-stage embryos that were thawed and cultured in blastocyst medium for two hours prior to blastomere biopsy. A single blastomere was removed from one embryo, and two blastomeres were removed from the second embryo. The remaining biopsied embryos were allowed to continue development and were frozen at the blastocyst stage. Extracted blastomeres were cultured under the same conditions as described for the second set of experiments of example 11 except that no GFP-hESCs were present. Both blastomere-derived aggregates generated cellular outgrowths, whereas one of the two embryos (50%) generated a stable hESC line. Immunostaining of the stable hESC line established from this colony (NED5) confirmed the expression of markers of pluripotency, including Oct-4, Nanog, SSEA-3, SSEA-4, TRA-1-60, TRA-1-81, and alkaline phosphatase (FIG. 11C). The newly established hESC line had a normal male (46 XY) karyotype (FIG. 14) and differentiated into derivatives from all three germ layers, including immunostaining with antibodies to tubulin β III (ectoderm), smooth muscle actin (mesoderm), a fetoprotein (primitive endoderm).

Example 14

Laminin Directs Blastomere Differentiation Toward ICM

Figures 15A, 15B, 15C, 15D, 15E, 15F, 15G, 15H, 15I:
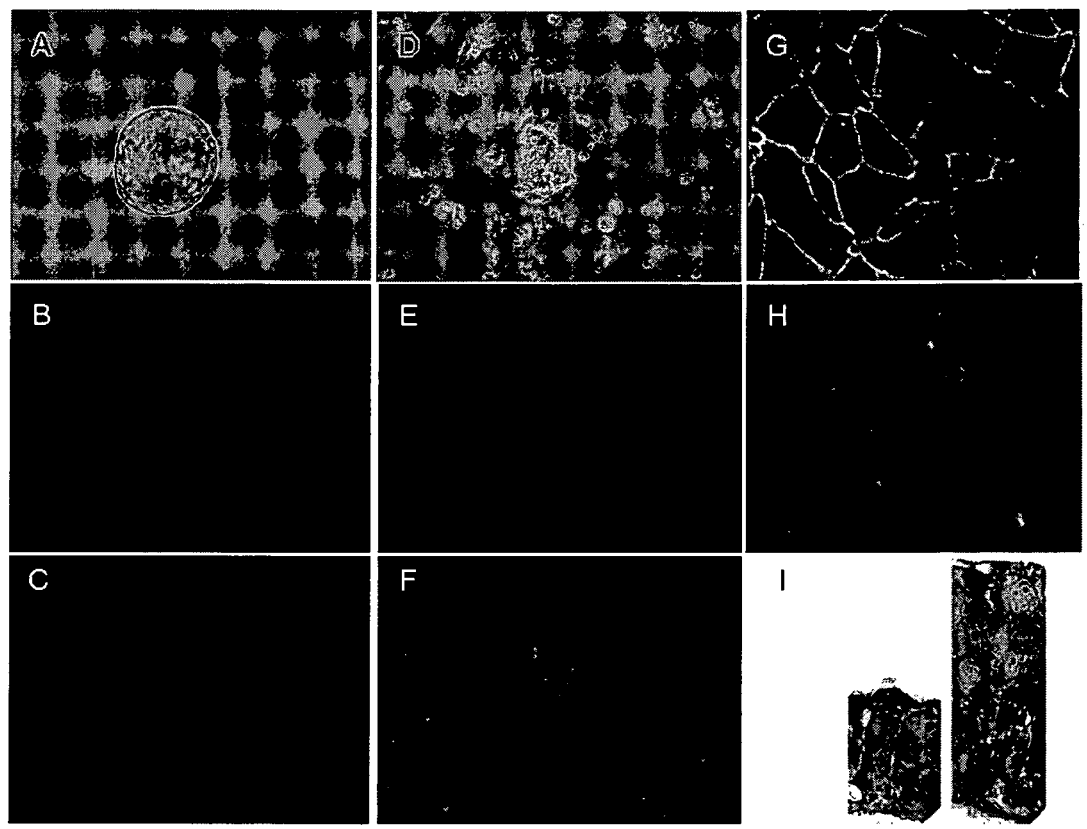
FIG. 15A-15H show effects of laminin on single blastomere development and hES cells. (A-C) formation of trophectoerm-like vesicles in the absence of laminin. (A) Hoffman modulation contrast, (B) immunostaining for cdx2, (C) immunostaining for cytokeratin 8. (D-F) formation of ICM-like outgrowth in the presence of laminin. (D) phase contrast, (E) immunostaining for Oct-4, (F) corresponding DAPI image. (G-I) depolarization effects of laminin on hESC. (G,H) Confocal microscopy of the control (G) and laminin (H) overlaid hESC (WA07) costained with tight junction marker ZO-1(green) and pluripotency marker Oct-4 (red). Ultrastructural analysis (semithin sections) of the cross section of the control (left) and laminin overlaid (right) hESC colony (WA09). The control colony is organized into a semi-stratified epithelium. Presence of apical microvilli (my) and tight junctions (data not shown) indicate structural specialization typical for epithelial-like polarization. Laminin overlay induced cell depolarization as shown by lack of microvilli on the cell surface and piling of cells to form multilayered structures. Magnification: (A-F) 200×, (G,H) 630×, (I)400×

Separate studies were carried out to investigate the mechanism of enhanced blastomere differentiation into ICM. In the absence of laminin and fibronectin, dissociated single blastomeres uniformly differentiated into trophectoderm (16/16 [100%] of blastomere outgrowths contained trophectodermal cells vs. 0/16 [0%] ICM-like cells). In contrast, when laminin was added to the medium, only 1/14 (7%) of blastomere-derived aggregates gave rise to trophectoderm-like vesicles and 13/14 (93%) yielded ICM-like cells. The addition of fibronectin alone had little or no effect on lineage specification (5/6 [83%] of outgrowths contained trophectodermal cells vs. 1/6 [17%] ICM-like cells). This suggests that laminin may play a key role in directing blastomere differentiation toward ICM. To test this hypothesis we immunostained blastomere-derived vesicles formed in the absence of laminin (FIG. 15A) and ICM-like cells (FIG. 15D) derived in the presence of laminin for the markers of trophectoderm and ICM/ESC, respectively. As expected, blastomere-derived vesicles that formed without laminin expressed key trophectoderm markers including cytokeratin 8 and cdx2 (FIGS. 15B,C) while ICM-like outgrowths formed in the presence of laminin, expressed Oct-4 (FIG. 15E). Interestingly, immunostaining for tight junction marker ZO-1 and ultrastructural analysis by transmission electron microscopy and semithin sections (FIG. 15G-I) revealed that the addition of laminin to the culture medium of established hESC lines disrupts tight junctions and depolarizes ESCs inducing them to assume ICM-like phenotype. Furthermore, staining with ZO-1 confirmed that the addition of laminin to the culture medium of the blastomeres disrupted tight junctions and inhibited the trophectoderm differentiation pathway.

Example 15

Materials and Methods for Examples 11-14

Single Blastomere Biopsy

Leftover embryos produced by IVF for clinical purposes were obtained with full informed consent and used in compliance with Advanced Cell Technology's Ethics Advisory Board (EAB) and Institutional Review Board (IRB). Donated pronuclear stage embryos were thawed using an embryo thawing kit (Cooper Surgical, CAT #ART-8016) according to manufacturer's direction. All procedures were performed at room temperature. Briefly, the embryos were thawed in air for 2 min. followed by 37° C. for 3 min. before being unloaded to 0.5M sucrose thawing medium, where they were held for 10 min. The embryos then were moved to 0.3M sucrose thawing medium and incubated for 10 min. followed by several washes in embryo thaw diluents before being removed to pre-equilibrated embryo culture medium. The thawed embryos were cultured in Quinn's cleavage medium in 20 ul drops in a highly humidified incubator with 6% CO2 in air at 37° C. Only embryos which developed to the 8-cell stage by 48 hrs. post thawing were subjected to single blastomere biopsy. Before the biopsy, a small hole (50 uM in diameter) in the zona pellucida was made on all embryos using a PIEZO drill followed by incubation in Ca++ and Mg++ free PBS supplemented with 0.05% PVA (poly vinyl alcohol) for 15 min. The blastomere biopsy was performed at 37° C. in Quinn's Hepes medium supplemented with 5% SPS (serum protein substitute, Cooper Surgical) using a PIEZO drill as described previously. Only a single blastomere (or in a small number of case, two blastomeres) was removed from each embryo. In Experimental Group 1 the parental embryos and biopsied blastomeres were cocultured for 12-24 h and then transferred to Quinn's blastocyst medium and cocultured for another 48 hrs. After the coculture parental embryos were frozen, the blastomere clumps were moved to MEF drops for further outgrowth as described below. In Experimental Group 2, the parental embryos and blastomeres were cocultured for less than 12 hrs. Then they were separated and the embryos were cultured in Quinn's blastocyst medium for another 48 hrs before freezing. The blastomeres in Experiment 2 were cultured in Quinn's blastocyst medium supplemented with laminin from human placenta (Sigma) and fibronectin (from human plasma, Sigma) on MEF cells for 5 days.

Blastocyst Freezing

After confirming blastocoel formation, the parental embryos were frozen using a Blastocyst Freezing kit (Cooper Surgical, Cat #ART-8015) according to manufacturer's directions. All the procedures were performed at room temperature.

Briefly, the embryos were rinsed and cultured in diluent medium for 5 min, then transferred to 5% glycerol freezing medium for 10 min before being moved to the final 9% glycerol plus 0.2 M sucrose freezing solution. Then each embryo was loaded in a 0.25 ml embryo freezing straw (IMV-ZA475, France) before freezing. The embryo freezing was performed using an embryo freezer (Freeze Control CL-869, Australia). The embryos were taken from a starting temperature of 25° C. to −6.5° C. at 2° C./min. Then they were seeded manually and held at −6.5° C. for 10 min before being cooled at 0.3° C./min to −45° C. and transferred to a liquid nitrogen storage tank.

ESC Derivation hESC culture was performed as previously described (Klimanskaya et al., 2006; Klimanskaya et al., 2007; Klimanskaya and McMahon, 2004). In Experimental Group 1, two days before embryonic vesicle plating, MEF cells were plated on gelatin-treated 60 mm cell culture dishes in rows of 50 ul drops. The MEF cell drops were arranged as 2 or 3 drops ("auxiliary drops") surrounded one "blastomere drop"—the drop) designated for the blastomere outgrowth On the second day, small clumps of GFP+hES cells were transferred into the "auxiliary drops" and cultured overnight, and the MEF plating medium in these drops was replaced with hESC medium. On the third day, the medium in "blastomere drops" was replaced with freshly prepared Quinn's blastocyst culture medium supplemented with 5 ug/ml fibronectin and 2.5 ug/ml laminin. Then the culture dishes were pre-incubated for at least 3 hrs in a 6% CO2 incubator before the embryonic vesicles were transferred. The day after vesicle transfer, each vesicle culture drop was connected to 2 or 3 surrounding GFP-hESC drops by dragging medium with a small glass pipette between two drops. The following day, the connecting channels were widened with a pipette, and the blastocyst medium was replaced with derivation medium as described above two days later. Once the initial outgrowth formed a colony large enough for dispersion (usually 3-5 days after plating), it was dissected into 2 pieces and re-plated into the same drop.

In Experimental Group 2, the blastomeres were cultured in 50 ul drops of Quinn's blastocyst medium supplemented with 5 ug/ml fibronectin and 5 ug/ml laminin containing MEF cells (as prepared in Experimental Group 1) after the first 12 hours of coculture with the parental embryos. The blastomere culture drops and the surrounding GFP ESC culture drops were not connected for 5 days. During this time most blastomeres formed clumps of cells comprising 20-30 cells resembling inner cell mass. At day 6 after plating, the blastomere culture drops and surrounding GFP ESC culture drops were connected as in Experimental Group 1, and the blastocyst medium was replaced with derivation medium on day 7. The initial outgrowths were checked daily and propagation of the outgrowth was performed as in Experimental Group 1. Half of the original volume of the culture medium was replaced every other day. As soon as stable growth of hESCs was observed, serum was removed from the culture medium. The detailed procedures are described in Klimanskaya et al., 2007 (Klimanskaya et al., 2007)

Experimental Group 3 followed the same procedures as Group 2 but without hESC-GFP coculture.

Immunostaining

Immunostaining was performed using standard protocols. Briefly, the samples were fixed with 2% paraformaldehyde for 10 minutes (cells) or 40 minutes (vesicles), permeabilized with 0.1% NP-40, blocked for 1 h with PBS containing 10% each goat and donkey serum, and incubated with the primary antibodies overnight at 4° C. Three washes of 10 minutes each were performed after each antibody incubation. Fluorescently labeled or biotinilated secondary antibodies (Jackson Immunoresearch or Molecular Probes) were added for 1 h, and fluorescently labeled Streptavidin (Molecular Probes) was added for 15 minutes to visualize biotinylated secondary antibodies. The samples were mounted in Vectashield with DAPI (Vector Laboratories, Burlingame, Calif.) and photographed using an inverted fluorescent microscope (Nikon). Peroxidase staining of teratoma sections was performed using standard protocols. Briefly, slides were dewaxed in xylenes three times. The xylenes were removed with 100% ethanol, endogenous peroxidase activity was blocked with 3% H2O2, and slides were incubated in blocker as above containing 0.1% Triton X-100 for one hour, followed by incubation in primary antibody diluted in the same blocker at 4 deg overnight. Primary antibodies against the following antigens were used: Oct-4 (Santa Cruz Biotechnology, Santa Cruz, Calif.), SSEA-3, SSEA-4, TRA-1-60, TRA-1-81 (Chemicon, Temecula, Calif.), Nanog (Kamiya), βIIItubulin (Covance), α-feto protein, smooth muscle actin (Dako), cdx2 (Abeam), ZO-1 (Zymed), cytokeratin 8 (Developmental Studies Hybridoma Bank)

Teratoma Formation

NOD-SCID male mice 6-8 weeks of age were used (Jackson Laboratories, Bar Harbor, Me.). Small clumps of 50-100 cells were injected under the kidney capsule, and 7-12 weeks after transplantation the mice were sacrificed, the kidneys fixed in 4% paraformaldehyde overnight, embedded in paraffin, sectioned, immunostained or stained with hematoxylin-eosin and analyzed for the presence of the derivatives of all three germ layers.

PCR Analysis of GFP Sequence

Genomic DNA from WA01-GFP (H1-GFP), NED1, NED2, NED3 and NED4 cells was isolated using a MicroDNA kit (Qiagen), and GFP-specific PCR reactions were performed as described previously (Klimanskaya et al., 2006) As an internal control for the PCR reactions, myogenin primers were included in all PCR reactions, which generate a fragment of 245 by as described (Klimanskaya et al., 2006). PCR products were separated on a 3% agarose gel and visualized by ethidium bromide staining.

Generation of Blast Cells from NED hES Cells

The generation of blast cells from NED hESCs with both hematopoietic and endothelial potentials was carried out as reported previously (Lu et al., 2007). Briefly, 3.5 day-old embryoid bodies (EBs) were generated from hESCs cultured in StemLine II serum-free media supplemented with a combination of morphogens and early hematopoietic cytokines, and the early-stage EBs were then dissociated and individual cells plated in serum-free semi-solid blast-colony growth medium for 7 days. The grape-like blast colonies were picked up and plated for both hematopoietic and endothelial cell differentiation.

Endothelial Progenitor Assay

For the endothelial progenitor assay, blast cells were plated on fibronectin-coated plates (BD Bioscience) in EGM-2 complete media (Lonza) for 3-5 days. For Ac-LDL uptake, hES-BC cells were cultured for 3-5 days on fibronectin-coated wells and incubated for 6-8 h with 10 µg/ml of Alexa Fluor 594-labeled Ac-LDL (Invitrogen). Then cells were washed 3 times with 1× PBS and fixed with 4% paraformaldehyde for 30 min. The uptake of Ac-LDL was visualized under a fluorescent microscope. For the expression of vWF (Dako), PECAM-1 (CD31) (Cell Signalling Technologies), VE-cadherin (R&D Systems), and KDR (Cell Signalling Systems), cells were permeabilized and then incubated with primary antibodies overnight at 4° C., and then incubated with corresponding secondary antibodies labeled with FITC (Jackson Laboratory) for 30-60 min. After final wash, cells were checked under a fluorescent microscope.

Karyotyping

The cells were plated on gelatin at 1:6 ratio. When the cells were approximately 50% confluent, 0.12 ug/ml colcemid (Invitrogen) was added to the culture for 40 min. The cells were harvested by trypsin, incubated in 0.075M KCl for 12 minutes at 37° C., fixed with 3:1 Methanol and acetic acid. The spread analysis was performed by Cell Line Genetics, Inc. (for the hESC lines NED1-NED4) and by the Cytogenetics Laboratory at the Children's Hospital, Oakland (NED5) using G-banding technique.

Genotyping

Identification of the newly derived hESC lines was performed by SeqWright, Inc. using the AmpF1STR Identifiler kit (Applied Biosystems)

RNA Isolation and Gene Expression Analysis by PCR

Total RNA was isolated from approximately 100 hESCs and eluted in 80 ul of DEPC-H2O using an RNAeasy Micro Kit (Qiagen, Valencia, Calif.) following the procedure recommended by the supplier. RNA was subjected to first-strand cDNA synthesis with SMART IIA and SMART CDS primer IIA (Clontech), using Superscript II reverse transcriptase (Clontech), and cDNA pool was constructed using the Super SMART cDNA synthesis kit (Clontech) as suggested by the supplier. Five ul of cDNA pool were used for the analysis of OCT-4 and Nanog expression, with the hypoxanthine phosphoribosyltransferase (HPRT) gene as a positive control. Total RNA isolated from H1 ES cells was used as a positive control and H2O was used as negative control. Ten µl of PCR products were separated on a 1.5% agarose gel and visualized by ethidium bromide staining.

References

Ioue K, et al (2003). Effects of donor cell type and genotype on the efficiency of mouse somatic cell cloning. Biol Reprod 69:1394-4000.

Rybouchkin A, et al (2002). Developmental potential of cloned mouse embryos reconstructed by a conventional technique of nuclear injection. Reproduction 124:197-207.

Wakayama S, et al (2005). Establishment of male and female nuclear transfer embryonic stem cell lines from different mouse strains and tissues. Biol Reprod 72:932-936.

Tong G, et al (2006). Aberrant profile of gene expression in cloned mouse embryos derived from donor cumulus nuclei. Cell Tissue Res 325: 231-243. Sebastiano V, et al (2005). Cloned pre-implantation mouse embryos show correct timing but altered levels of gene expression. Mol Reprod Dev70:146-154.

Chung Y, et al(2003). Abnormal regulation of DNA methyltransferase expression in cloned mouse embryos. Biol Reprod 69:146-153.

Kishigami S, et al (2006). Significant improvement of mouse cloning technique by treatment with trichostatin A after somatic nuclear transfer. Biochem Biophys Res Commun 340:183-189.

Heindryckx B, et al (2002). Serial nuclear transfer increases the developmental potential of in vitro-matured oocytes in mouse cloning. Biolo Reprod 67:1790-1795.

Ono Y, et al (2001). Cloned mice from fetal fibroblast cells arrested at metaphase by a serial nuclear transfer. Biol Reprod 64:44-50.

Polejeva I, et al (2000). Cloned pigs produced by nuclear transfer from adult somatic cells. Nature 407:86-90.

Amano T, et al(2001). Mouse cloned from embryonic stem cells synchronized in metaphase with Nocodazole. J Exp Zoology 287:139-145.

Yabuchi A, et al (2001). Nuclear transfer of mouse follicular epithelial cells pretreated with spermine, protamine, or putrescine. J Exp Zoology 289:208-212.

Sullivan E, et al (2004). Cloned calved from chromtin remodeled in vitro. Biol Reprod 70:146-153.

Enright B, et al (2003). Epigenetic characteristics and development of embryos cloned from donor cells treated by trichostatin A or 5-aza-2'-deoxycytidine. Biol Reprod 69:896-901.

Campbell K, et al (1996). Cell cycle co-ordination in embryo cloning by nuclear transfer. Reviews Reprod 1:40-46.

Chartot C, et al (1989). An improved culture medium supports development of random-bred 1-cell mouse embryos in vitro. J Reprod Fertil 86:679-688.

Chung, et al(2006). Optimization of procedure for cloning by somatic cell nuclear transfer in mice. Method Mol Biol 348:111-124.

Chung Y and Becker S (2006). Embryonic stem cells using nuclear transfer. Method Enz 418: 135-147.

Bayona-Bafaluy M P, et al (2003). Revisiting the mouse mitochondrial DNA sequence. Nucleic Acids Res. 31:5349- 5355.

Wakayama T, et al (1998). Full-term development of mice from enucleated oocytes injected with cumulus cell nuclei. Nature 394:369-374.

Livak K and Schmittgen T (2001). Analysis of relative gene expression data using real-time quantitive PCR and the $2^{-\Delta\Delta C_T}$ Method. Methods 25:402-408.

Shi W, et al (2004). Methylation reprogramming and chromosomal aneuploidy in in vitro fertilized and cloned rabbit preimplantation embryos. Biol Reprod 71:340-347.

Mann M, et al (2003). Disruption of imprinted gene methylation and expression in cloned preimplantation stage mouse embryos. Biol Reprod 69:902-914.

Dean W, et al (2001). Conservation of methylation reprogramming in mammalian development: aberrant reprogramming in cloned embryos. PNAS 98:13734-13738.

Rideout III W, et al (2001). Nuclear cloning and epigenetic reprogramming of the geneome. Science 293:1093-1098.

Wakayama T, et al (1998). Full term development of mice from enucleated oocytes injected with cumulus cell nuclei. Nature 394:369-374.

Chung Y, et al (2002). Nuclear-cytoplasmic "tug of war"during cloning: effects of somatic cell nuclei on culture medium preferences of preimplantation cloned mouse embryos. Biol Reprod 66:1178-84.

Heindryckx B, et al (2001). Effects of culture media on invitro deveopelment of cloned mouse embryos. Cloning 3:41-50.

Kishikawa H, et al (1999). Comparison of oocyte activating agents for mouse cloning. Cloning 1:153-159.

Miyoshi K, et al (2003). Improvements in cloning efficiencies may be possible by increasing uniformity in recipeient oocytes and donor cells. Biol Reprod 68:1079-1086.

Boiani M, et al (2003). Pluripotency deficit in clones overcome by clone-clone aggregation: epigenetic complementation? EMBO J 22:5304-5312.

Gibbons J, et al (2002). Enhanced survivability of cloned calves derived from roscovitine-treated adult somatic cells. Biol Reprod 66:895-900.

Eggan K, et al (2001). Hybrid vigor, fetal overgrowth, and viability of mice derived by nuclear cloning and tetraploid embryo complementation.

Van Thuan N, et al (2006). Injection of somatic cell cytoplasm into oocytes before intracytoplasmic sperm injection impaires full-term development and increases placental weight in mice. Biol Reprod Ono Y, et al (2001). Cloned mice from fetal fibroblast cells arrested at metaphase by a serial nuclear transfer. Biol Reprod. 64:44-50.

Latham K, et al (1992). Acquisition of transcriptionally permissive state during the 1-cell stage of mouse embryogenesis. Dev Biol 149:457-462.

Gao S, et al (2003). Somatic cell-like features of cloned mouse embryos prepared with cultured myoblast nuclei. Biol Reprod 69:48-56.

Simerly C, et al (2003). Molecular correlates of primate nuclear transfer failures. Science 300:297.

Kim J, et al (2002). Analysis of the mechanism for chromatin remodeling in embryos reconstructed by somatic cell nuclear transfer. Biol Reprod 67:760-766.

Boiani M, et al (2002). Oct4 distribution and level in mouse clones: consequences for pluripotency. Genes Dev 16:1209-1219.

Klimanskaya I, Chung Y, Becker S, Lu S J, Lanza R. Human embryonic stem cell lines derived from single blastomeres. Nature 2006; 444(7118):481-485.

Lanza R, Thomas E D, Thomson J A, Pedersen R. Essentials of Stem Cell Biology. San Diego: Elsevier Academic Press; 2006.

Thomson J A, Itskovitz-Eldor J, Shapiro S S et al. Embryonic stem cell lines derived from human blastocysts. Science 1998; 282(5391):1145-1147.

Cowan C A, Klimanskaya I, McMahon J et al. Derivation of embryonic stem-cell lines from human blastocysts. N Engl J Med 2004; 350(13):1353-1356.

Reubinoff B E, Pera M F, Fong C Y, Trounson A, Bongso A. Embryonic stem cell lines from human blastocysts: somatic differentiation in vitro. Nat Biotechnol 2000; 18(4):399-404.

Lanzendorf S E, Boyd C A, Wright D L, Muasher S, Oehninger S, Hodgen G D. Use of human gametes obtained from anonymous donors for the production of human embryonic stem cell lines. Fertil Steril 2001; 76(1):132-137.

Hovatta O, Mikkola M, Gertow K et al. A culture system using human foreskin fibroblasts as feeder cells allows production of human embryonic stem cells. Hum Reprod 2003; 18(7):1404-1409.

Klimanskaya I, Chung Y, Meisner L, Johnson J, West M D, Lanza R. Human embryonic stem cells derived without feeder cells. Lancet 2005; 365(9471):1636-1641.

Strelchenko N, Verlinsky O, Kukharenko V, Verlinsky Y. Morula-derived human embryonic stem cells. Reprod Biomed Online 2004; 9(6):623-629.

Dickey-Wicker Amendment. Publication L No.104-99, paragraph 128,110 Statute 34. 1996.

Neuber E, Rinaudo P, Trimarchi JR, Sakkas D. Sequential assessment of individually cultured human embryos as an indicator of subsequent good quality blastocyst development. Hum Reprod 2003; 18(6):1307-1312.

Veeck L L. An Atlas of Human Gametes and Conceptuses. New York, N.Y.: Parthenon Publishing Group; 1999.

Klimanskaya I, Chung Y, Becker S, Lu S J, Lanza R. Human embryonic stem cell lines derived from single blastomeres. Nature Protocols. In press. Geber S, Sampaio M. Blastomere development after embryo biopsy: a new model to predict embryo development and to select for transfer. Hum Reprod 1999; 14(3):782-786.

Palmer G A, Traeger-Synodinos J, Davies S et al. Pregnancies following blastocyst stage transfer in PGD cycles at risk for beta-thalassaemic haemoglobinopathies. Hum Reprod 2002; 17(1):25-31.

Simon C, Escobedo C, Valbuena D et al. First derivation in Spain of human embryonic stem cell lines: use of long-term cryopreserved embryos and animal-free conditions. Fertil Steril 2005; 83(1):246-249.

Klimanskaya I, McMahon J. Approaches for Derivation and Maintenance of human ES cells: detailed procedures and alternatives. In: Lanza R, Gearhart J, Hogan B, editors. Handbook of Stem Cells. San Diego: Elsevier Academic Press; 2004 p. 437-449.

Krtolica A, Genbacev O, Escobedo C et al. Disruption of Apical-Basal Polarity of Human Embryonic Stem Cells Enhances Hematoendothelial Differentiation. Stem Cells 2007.

Weber D J. Manufacturing considerations for clinical uses of therapies derived from stem cells. Methods Enzymol 2006; 420:410-430.

Klimanskaya I, McMahon J. Approaches for Derivation and Maintenance of human ES cells: detailed procedures and alternatives. In: Lanza R, Gearhart J, Hogan B, editors. Handbook of Stem Cells. San Diego: Elsevier Academic Press; 2004 p. 437-449.

Klimanskaya I, Chung Y, Becker S, Lu S J, Lanza R. Human embryonic stem cell lines derived from single blastomeres. Nature 2006; 444(7118):481-485.

Klimanskaya I, Chung Y, Becker S, Lu S J, Lanza R. Human embryonic stem cell lines derived from single blastomeres. Nature Protocols. In press. Lu S J, Feng Q, Caballero S et al. Generation of functional hemangioblasts from human embryonic stem cells. Nat Methods 2007; 4(6):501-509.

The invention claimed is:

1. A method of producing an mammalian embryonic stem (ES) cell, comprising
   (a) culturing a mammalian blastomere for 12 to 18 hours;
   (b) transferring the blastomere to blastocyst medium further comprising laminin and seeded with fibroblasts; and
   (c) culturing the blastomere of (b) until ES cells are produced.

2. The method of claim 1, wherein the fibroblasts are mitotically inactivated, wherein step (c) comprises culturing in conditions that reduce embryonic vesicle formation, wherein the blastocyst medium comprises 2.5 μg/ml of laminin, and wherein step (c) comprises culturing in blastocyst medium seeded with fibroblasts for 5 days.

3. The method of claim 1, wherein step (c) further comprises culturing until the blastomeres form cell clumps of about 20 cells and transferring the cell clumps to medium seeded with ES cells that express a marker or are labeled.

4. The method of claim 1, wherein step (a) comprises culturing said blastomere with a mammalian parental embryo from which said blastomere was obtained.

5. The method of claim 1, wherein said blastomere is human.

6. The method of claim 1, wherein step (b) comprises culturing said blastomere in indirect contact with pluripotent cells.

7. The method of claim 1, wherein said fibroblasts are mouse embryonic fibroblasts.

\* \* \* \* \*

UNITED STATES PATENT AND TRADEMARK OFFICE
CERTIFICATE OF CORRECTION

| | | |
|---|---|---|
| PATENT NO. | : 8,796,021 B2 | Page 1 of 1 |
| APPLICATION NO. | : 12/528212 | |
| DATED | : August 5, 2014 | |
| INVENTOR(S) | : Robert P. Lanza et al. | |

It is certified that error appears in the above-identified patent and that said Letters Patent is hereby corrected as shown below:

In the Claims:

Column 68, claim 1, line 21, delete "an", and insert --a--.

Signed and Sealed this
Twenty-first Day of October, 2014

Michelle K. Lee
*Deputy Director of the United States Patent and Trademark Office*